United States Patent
Majeti et al.

(10) Patent No.: US 9,850,297 B2
(45) Date of Patent: Dec. 26, 2017

(54) SECRETED FRIZZLE-RELATED PROTEIN 5 (SFRP5) BINDING PROTEINS

(71) Applicant: AMGEN INC., Thousand Oaks, CA (US)

(72) Inventors: Jiangwen Majeti, Palo Alto, CA (US); YuMei Xiong, Palo Alto, CA (US); Wen-Chen Yeh, Belmont, CA (US); Alykhan S. Motani, San Francisco, CA (US); Yang Li, Mountain View, CA (US)

(73) Assignee: Amgen Inc., Thousand Oaks, CA (US)

( * ) Notice: Subject to any disclaimer, the term of this patent is extended or adjusted under 35 U.S.C. 154(b) by 105 days.

(21) Appl. No.: 14/776,012

(22) PCT Filed: Mar. 14, 2014

(86) PCT No.: PCT/US2014/029015
§ 371 (c)(1),
(2) Date: Sep. 14, 2015

(87) PCT Pub. No.: WO2014/144553
PCT Pub. Date: Sep. 18, 2014

(65) Prior Publication Data
US 2016/0024196 A1 Jan. 28, 2016

Related U.S. Application Data

(60) Provisional application No. 61/799,619, filed on Mar. 15, 2013.

(51) Int. Cl.
*C07K 16/18* (2006.01)
*C12N 5/10* (2006.01)
*C12N 15/10* (2006.01)
*C12N 15/11* (2006.01)
*A61K 39/00* (2006.01)

(52) U.S. Cl.
CPC ........ *C07K 16/18* (2013.01); *A61K 2039/505* (2013.01); *C07K 2317/14* (2013.01); *C07K 2317/51* (2013.01); *C07K 2317/515* (2013.01); *C07K 2317/565* (2013.01); *C07K 2317/76* (2013.01); *C07K 2317/92* (2013.01)

(58) Field of Classification Search
None
See application file for complete search history.

(56) References Cited

PUBLICATIONS

MacCallum et al., Antibody-antigen interactions: contact analysis and binding site topography, J. Mol. Biol. 262:732-745, 1996.*
Lamminmaki et al., Chrystal structure of a recombinant anti-estradiol Fab fragment in complex with the 17beta-estradiol, J. Blol. Chem. 276:36687-94, 2001.*
Chen et al., Enahncement and destruction of antibody function by somatic mutation: unequal occurrence is controlled by V gene combinatorial associations, EMBO J., 14 (12): 2784-2794, 1995.*
Blumenthal et al.; Blood, American society of Hematology; 2006; 108:3; 965-973.

(Continued)

Primary Examiner — Claire Kaufman

(57) ABSTRACT

Methods of treating metabolic diseases and disorders using an antigen binding protein specific for the SFRP5 polypeptide are provided. In various embodiments the metabolic disease or disorder is type 2 diabetes, obesity, dyslipidemia elevated glucose levels, elevated insulin levels and diabetic nephropathy.

11 Claims, 16 Drawing Sheets

(56) References Cited

PUBLICATIONS

He, et al., Science; A member of the Frizzled protein family mediating axis induction by Wnt-5A; 1997; 275:1652-1654.
International Search Report for International application No. PCT/US2014/029015, dated Aug. 5, 2014.
Li et al.; Genes & Development; 2008; Sfrp5 coordinates foregut specification and morphogenesis by antagonizing both canonical and non-canonical Wnt11 signaling; 22:21; 3050-3063.
Maury et al.; Molecular and Cellular Endocrinology; Elsevier Ireland; 2010; 314: 1-16.
Mori et al. ; J Clinical Investigation; Secreted frizzled-related protein 5 suppresses adipocyte mitochondrial metabolism through WNT inhibition; 2012; 122:7; 2405-2415.
Oh et al.; WNT fans the flames in obesity; Science; 2010; 329: 397-398.
Ouchi et al.; Science; Supporting online material for Sfrp5 is an anti-inflammatory adipokine that modulates metabolic dysfunction in obesity; 2010; 329: 1-18.
Rauch et al.; J Clinical Invest.; Lighting the fat furnace without SFRP5; 2012; 122:7; 2349-2352.

* cited by examiner

Figure 1
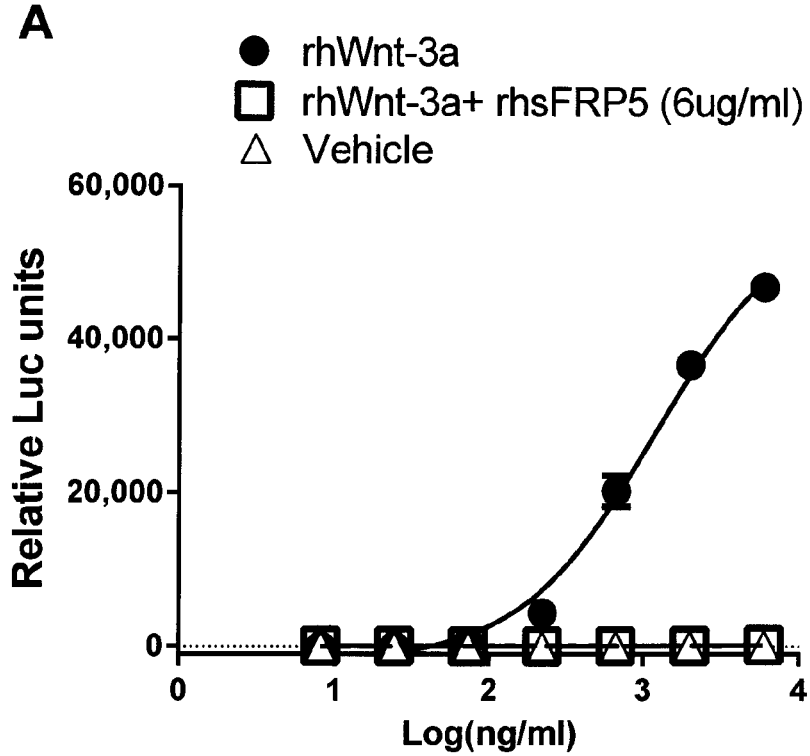
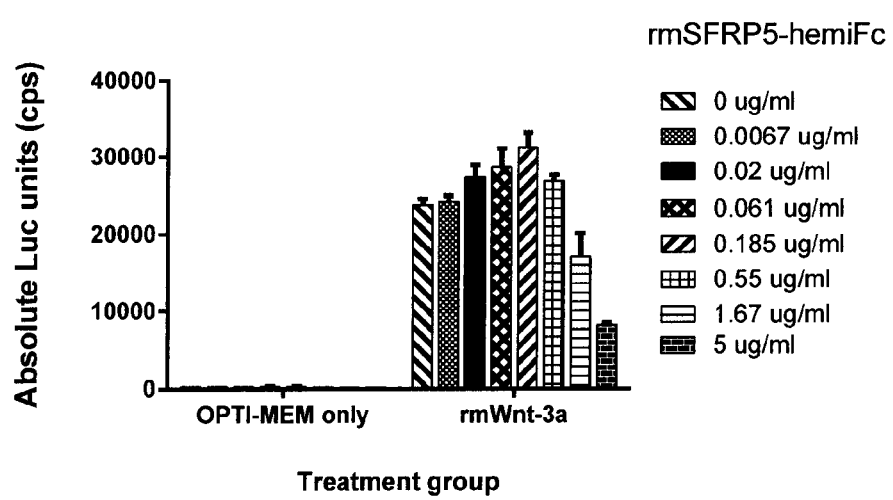

Figure 5
A
B
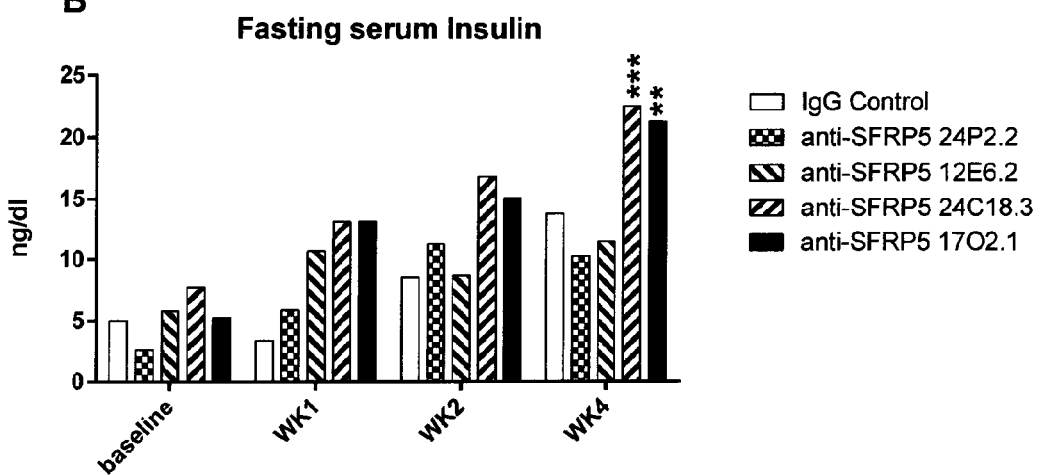

Figure 5 (continued)
C
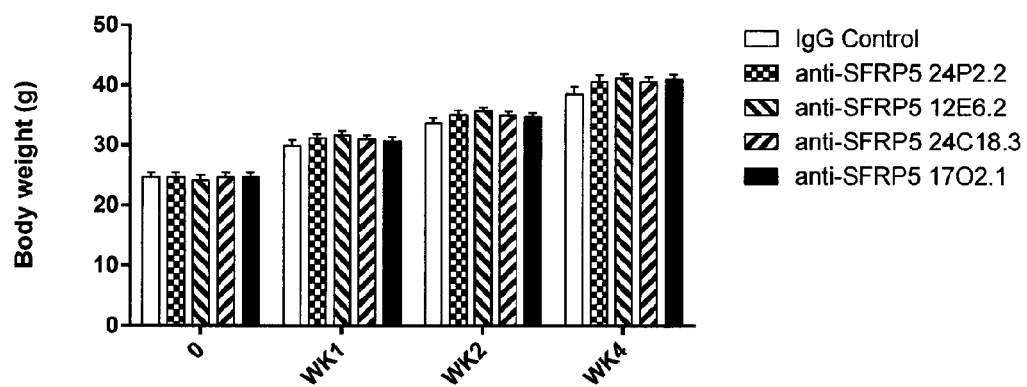
D
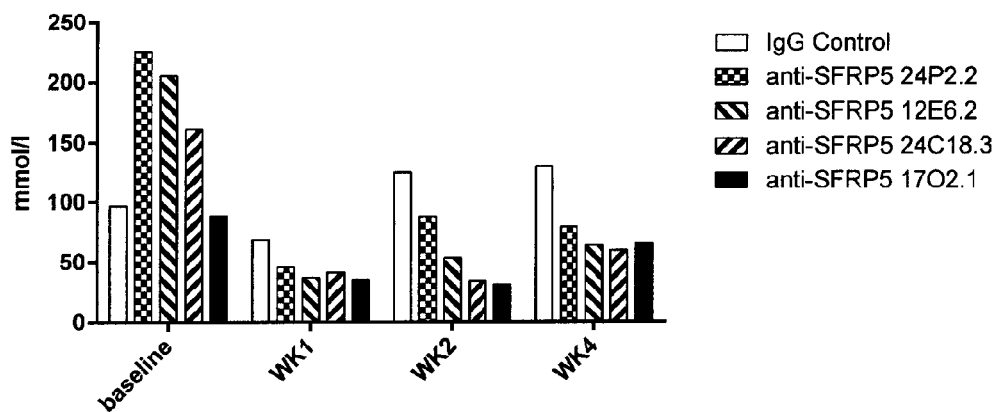

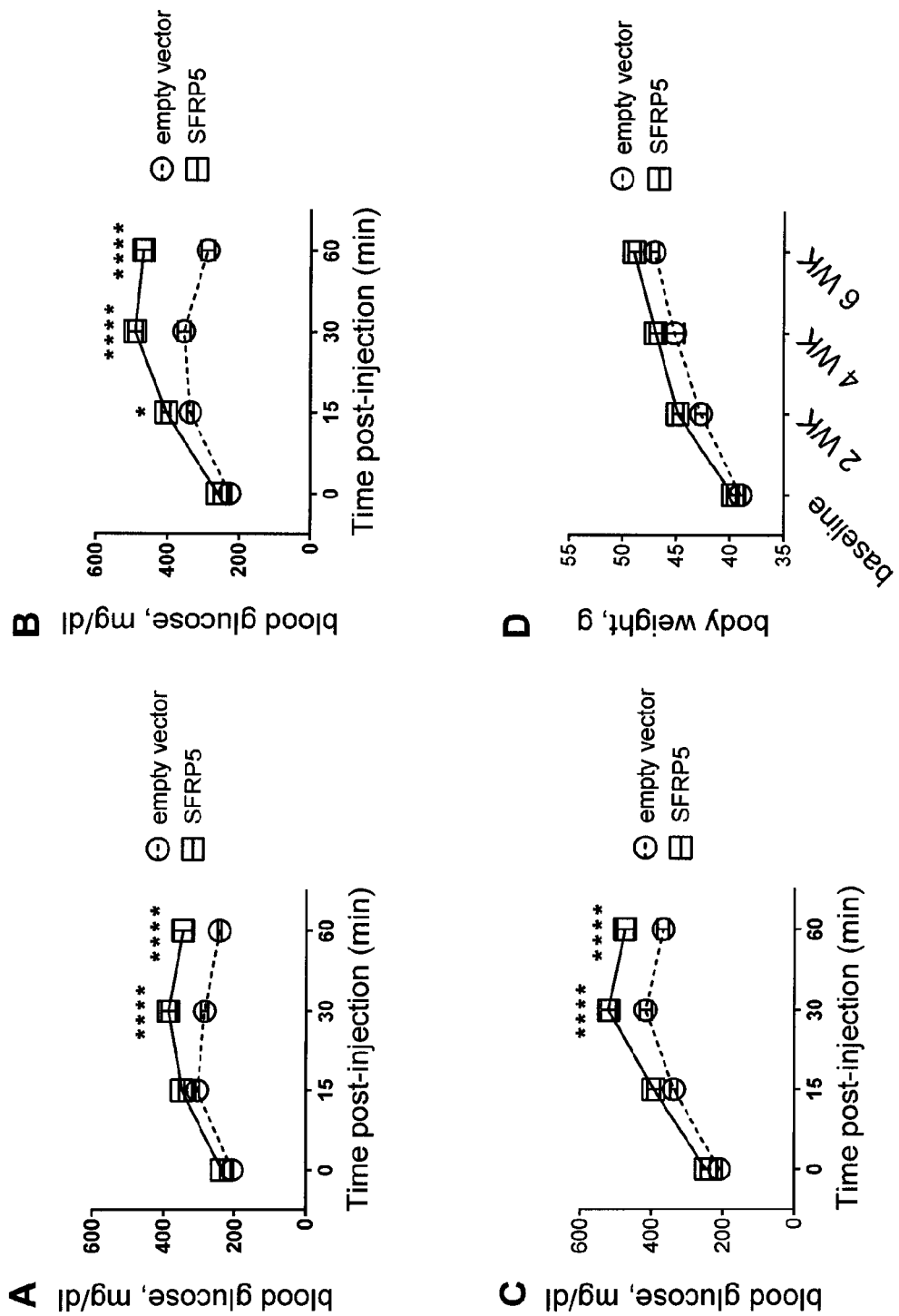

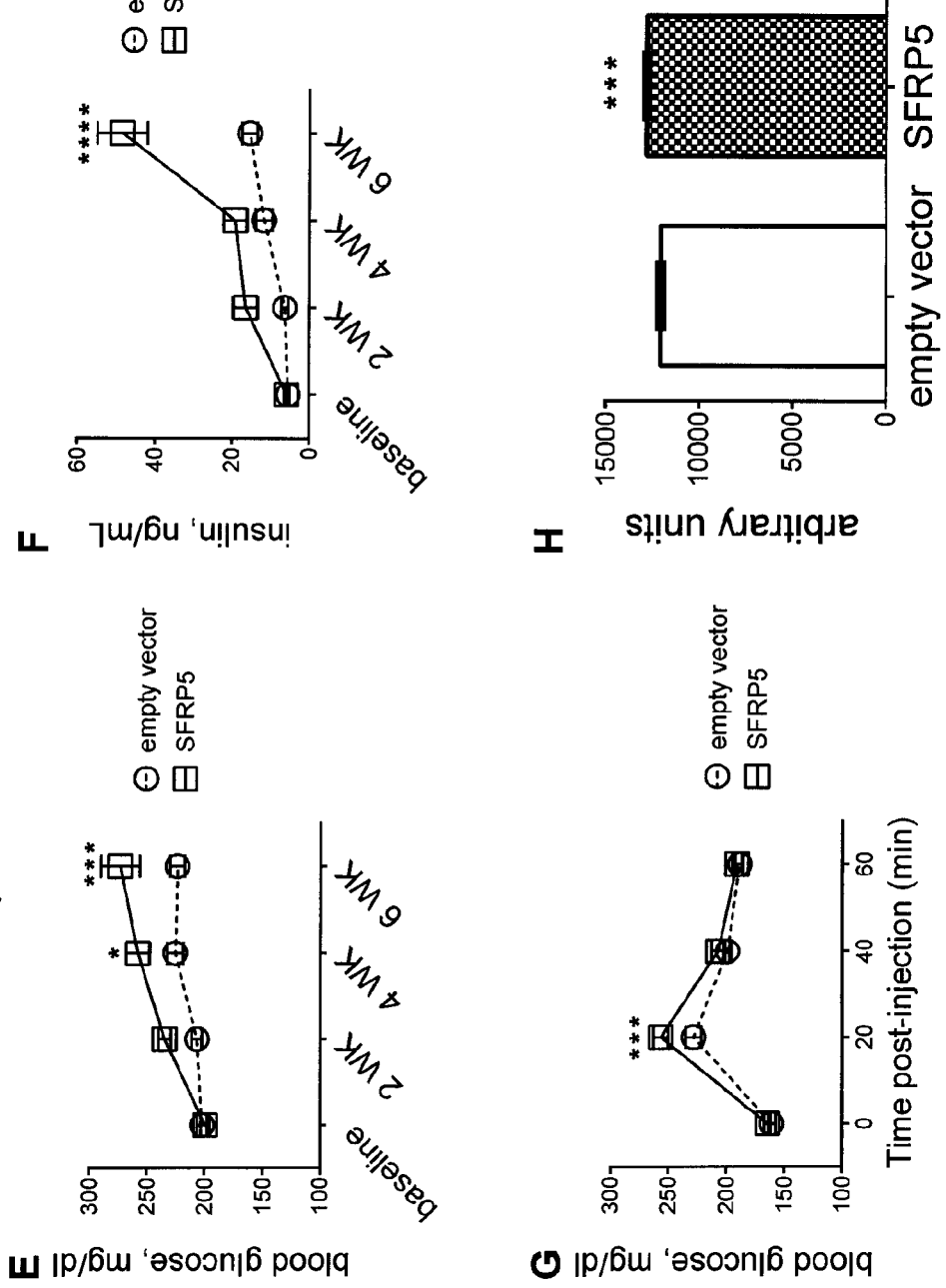

Figure 12
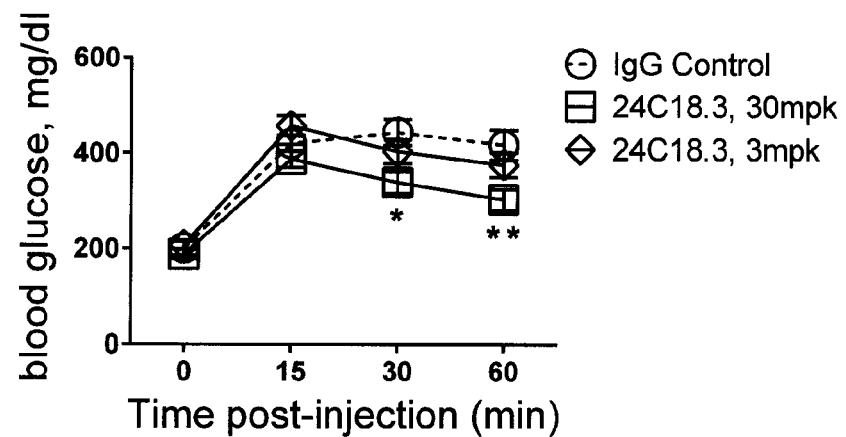
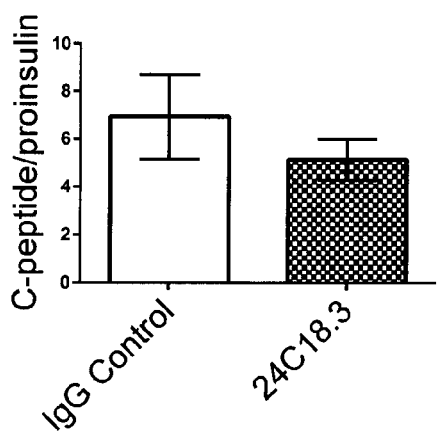
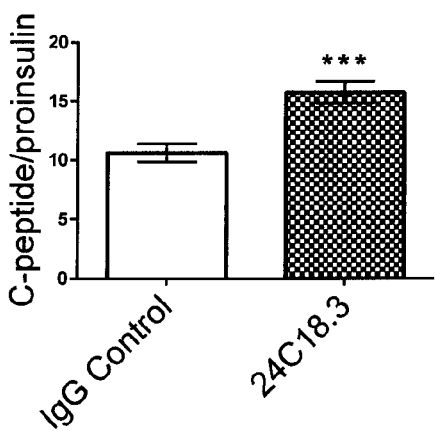

US 9,850,297 B2

SECRETED FRIZZLE-RELATED PROTEIN 5 (SFRP5) BINDING PROTEINS

This application is a national stage application under 35 U.S.C. §371 of International Application No. PCT/US2014/02901, having an international filing date of Mar. 14, 2014, which claims the benefit of U.S. Provisional Patent Application No. 61/799,619, filed on Mar. 15, 2013 which is hereby incorporated by reference.

The present application is being filed along with a Sequence Listing in electronic format. The Sequence Listing is provided as a file entitled A-1830-US-PCT_SeqList.txt, created Jun. 5, 2015, which is 45 KB in size. The information in the electronic format of the Sequence Listing is incorporated herein by reference in its entirety.

FIELD OF THE INVENTION

The present disclosure relates to the treatment or amelioration of a metabolic disorder, such as a disorder of glucose metabolism, by blocking or interfering with the biological activity of SFRP5.

BACKGROUND OF THE INVENTION

Secreted frizzled-related protein 5 (SFRP5) belongs to a family of secreted proteins that are antagonists for the WNT signaling pathway. It is also called SARP3. SFRPs are modular proteins that fold into two independent domains: 1) The N-terminus CRD (cystenine-rich domain) and 2) the NTR module. Chong et al., 2002, *J Biol Chem.*, 277:5134-5144; Bovolenta et al., 2008, *J Cell Sci.*, 121: 737-746. Biochemical studies performed in the 1990s established that SFRPs physically interact with WNT proteins to inhibit their binding to frizzled receptors and it is hypothesized this occurs via the CRD domain. Bovolenta et al., 2008.

Human SFRP5 gene is located on chromosome 10; and mouse SFRP5 gene is located on chromosome 19. Human SFRP5 is highly expressed in the retinal pigment epithelium (PRE) and pancreas, poorly expressed in heart, liver and muscle. Melkonyan et al., 1997, *Proc Natl Acad Sci U.S.A.*, 94:13636-13641; Hu et al., 1998, Biochem Biophys Res Commun 247:287-294; Chang et al., 1999, Hum Mol Genet 8:575-583.

Several GWAS studies link WNT-signaling to diabetes and metabolic dysfunction, suggesting that targeting proteins that modulate WNT-mediated signaling may have beneficial effects on diabetes. Grant et al., 2006, *Nature genetics* 38:320-323; Schafer et al., 2007, *Diabetologia* 50:2443-2450; Saxena et al., 2006, *Diabetes* 55, 2890-2895; Prokunina-Olsson et al., 2009, *PloS one* 4:e7231; Shu et al., 2009, *Human molecular genetics* 18:2388-2399; Shu et al., 2008, *Diabetes* 57:645-653; Groves et al., 2006, *Diabetes* 55:2640-2644; Guo et al., 2007. *Diabetes* 56:3082-3088; Grant et al., 2010, *Endocrine reviews* 31:183-193; Lyssenko et al., 2008, *The New England journal of medicine* 359: 2220-2232; Lyssenko et al., 2007, *The Journal of clinical investigation* 117:2155-2163; Guo et al., 2006, *Journal of medical genetics* 43:798-803; Fujino et al., 2003, *Proceedings of the National Academy of Sciences of the United States of America* 100:229-234; Magoori et al., 2003, *The Journal of biological chemistry* 278:11331-11336; Singh et al., 2013, *Cell metabolism* 17:197-209; Liu et al., 2012, *The Journal of biological chemistry* 287:7213-7223.

In 2010, Ken Walsh's group published data suggesting that ablation of SFRP5 in mice led to type 2 diabetic phenotypes that could be rescued by over-expression of adenovirus of SFRP5. Ouchi et al., 2010, *Science* 329:454-457. However, it has also been reported that mice that lack functional SFRP5 were resistant to diet-induced obesity. Mori et al., 2012, *The Journal of clinical investigation* 122:2405-2416.

SUMMARY OF THE INVENTION

Using a strategy of adeno-associated virus (AAV) vector technology, the present inventors over-expressed mouse SFRP5 in C57BL/6×DBA/2 F1 (BDF) diet-induced obese (DIO) mice, BDF lean mice, or B6.V-Lep$^{ob}$/J diabetic mice. Contrary to Walsh's findings, however, the present inventors reproducibly found over-expressed SFRP5 to significantly impair glucose tolerance and increase baseline fasting glucose. As described herein, the present inventors also made SFRP5 binding proteins to assess the efficacy of SFRP5 blockade on various diabetic phenotypes and found that blocking or interfering with the biological activity of SFRP5, e.g., by administering a therapeutically effective amount of an anti-SFRP5 monoclonal antibody, is useful in the treatment or amelioration of a metabolic disorder, such as Type 2 diabetes, elevated glucose levels, elevated insulin levels, dyslipidemia, obesity or diabetic nephropathy.

In a first embodiment, a method of treating a metabolic disorder in a patient comprising administering to the patient an effective amount of an antigen binding protein capable of inhibiting the activity of SFRP5 is provided.

In a second embodiment, a method of treating a disorder of glucose metabolism in a patient comprising administering to the patient an effective amount of an antigen binding protein capable of inhibiting the activity of SFRP5 is provided.

In a third embodiment, a method of treating diabetes mellitus in a patient comprising administering to the patient an effective amount of an antigen binding protein capable of inhibiting the activity of SFRP5 is provided.

In a fourth embodiment, a method of modulating blood glucose in a patient comprising administering to the patient an effective amount of an antigen binding protein capable of inhibiting the activity of SFRP5 is provided.

In a fifth embodiment, a method of treating insulin resistance in a patient comprising administering to the patient an effective amount of an antigen binding protein capable of inhibiting the activity of SFRP5 is provided.

In a sixth embodiment, a method of treating dyslipidemia in a patient comprising administering to the patient an effective amount of an antigen binding protein capable of inhibiting the activity of SFRP5 is provided.

In a seventh embodiment, a method of treating obesity in a patient comprising administering to the patient an effective amount of an antigen binding protein capable of inhibiting the activity of SFRP5 is provided.

In an eighth embodiment, a method of treating a disease or disorder characterized by undesired levels of triglycerides in a patient comprising administering to the patient an effective amount of an antigen binding protein capable of inhibiting the activity of SFRP5 is provided.

In a ninth embodiment, a method according to any one of the first eight embodiments is provided, wherein the antigen binding protein is an antibody.

In a tenth embodiment, a method according to any one of the first eight embodiments is provided, wherein the antigen binding protein is a humanized antibody.

In an eleventh embodiment, a method according to any one of the first eight embodiments is provided, wherein the antigen binding protein comprises:

a. one or more heavy chain complementary determining regions (CDRHs) selected from the group consisting of:
   i. a CDRH1 of SEQ ID NO:23;
   ii. a CDRH2 of SEQ ID NO:24;
   iii. a CDRH3 of SEQ ID NO:25;
   iv. a CDRH of (i), (ii) and (iii) that contains one or more amino acid substitutions, deletions or insertions totaling no more than 4 amino acids;
b. one or more light chain complementary determining regions (CDRLs) selected from the group consisting of:
   i. a CDRL1 of SEQ ID NO:26;
   ii. a CDRL2 of SEQ ID NO:27;
   iii. a CDRL3 of SEQ ID NO:28;
   iv. a CDRL of (i), (ii) and (iii) that contains one or more amino acid substitutions, deletions or insertions totaling no more than 4 amino acids; or
c. one or more CDRHs of (a) and one or more CDRLs of (b).

In a twelfth embodiment, a method according to any one of the first eight embodiments is provided, wherein the antigen binding protein comprises:
a. a CDRH selected from the group consisting of:
   i. a CDRH1 of SEQ ID NO:23;
   ii. a CDRH2 of SEQ ID NO:24; and
   iii. a CDRH3 of SEQ ID NO:25;
b. a CDRL selected from the group consisting of:
   i. a CDRL1 of SEQ ID NO:26;
   ii. a CDRL2 of SEQ ID NO:27; and
   iii. a CDRL3 of SEQ ID NO:28; or
c. one or more CDRHs of (a) and one or more CDRLs of (b).

In a thirteenth embodiment, a method according to the previous embodiment is provided, wherein the antigen binding protein comprises: a CDRH1 of SEQ ID NO:23, a CDRH2 of SEQ ID NO:24, a CDRH3 of SEQ ID NO:25; a CDRL1 of SEQ ID NO:26, a CDRL2 of SEQ ID NO:27, and a CDRL3 of SEQ ID NO:28.

In a fourteenth embodiment, a method according to any one of the first eight embodiments is provided, wherein the antigen binding protein comprises a heavy chain variable region ($V_H$) and/or a light chain variable region ($V_L$), wherein
a. the $V_H$ has at least 90% sequence identity with the amino acid sequence selected from the group consisting of SEQ ID NO: 19 and 20; and
b. the $V_L$ has at least 90% sequence identity with the amino acid sequence selected from the group consisting of SEQ ID NO:21 and 22.

In a fifteenth embodiment, a method according to the previous embodiment is provided, wherein the antigen binding protein comprises a heavy chain variable region ($V_H$) and a light chain variable region ($V_L$), wherein
a. the $V_H$ comprises the amino acid sequence of SEQ ID NO:19 and the $V_L$ comprises the amino acid sequence of SEQ ID NO:21;
b. the $V_H$ comprises the amino acid sequence of SEQ ID NO:20 and the $V_L$ comprises the amino acid sequence of SEQ ID NO:21;
c. the $V_H$ comprises the amino acid sequence of SEQ ID NO:19 and the $V_L$ comprises the amino acid sequence of SEQ ID NO:22; or
d. the $V_H$ comprises the amino acid sequence of SEQ ID NO:20 and the $V_L$ comprises the amino acid sequence of SEQ ID NO:22.

In a sixteenth embodiment, a method according to any one of the first eight embodiments is provided, wherein the antigen binding protein comprises a heavy chain (HC) and/or a light chain (LC), wherein
a. the HC has at least 90% sequence identity with the amino acid sequence selected from the group consisting of SEQ ID NO:15 and 16; and
b. the LC has at least 90% sequence identity with the amino acid sequence selected from the group consisting of SEQ ID NO: 17 and 18.

In a seventeenth embodiment, a method according to the previous embodiment is provided, wherein the antigen binding protein comprises a heavy chain (HC) and a light chain (LC), wherein
a. the HC comprises the amino acid sequence of SEQ ID NO:15 and the LC comprises the amino acid sequence of SEQ ID NO:17;
b. the HC comprises the amino acid sequence of SEQ ID NO:16 and the LC comprises the amino acid sequence of SEQ ID NO:17;
c. the HC comprises the amino acid sequence of SEQ ID NO:15 and the LC comprises the amino acid sequence of SEQ ID NO: 18; or
d. the HC comprises the amino acid sequence of SEQ ID NO: 16 and the LC comprises the amino acid sequence of SEQ ID NO:18.

In an eighteenth embodiment, an antigen binding protein that specifically binds to SFRP5 polypeptide is provided.

In a nineteenth embodiment, the antigen binding protein according to the eighteenth embodiment is provided, wherein the SFRP5 polypeptide is a human SFRP5 polypeptide.

In a twentieth embodiment, the antigen binding protein according to the eighteenth or nineteenth embodiment is provided, wherein the antigen binding protein is a human antigen binding protein.

In a twenty-first embodiment, the antigen binding protein according to the previous embodiment is provided, wherein the human antigen binding protein is a human antibody.

In a twenty-second embodiment, the antigen binding protein according to any one of embodiments eighteen through twenty-one is provided, wherein the antigen binding protein binds a human SFRP5 polypeptide consisting of SEQ ID NO:3.

In a twenty-third embodiment, the antigen binding protein according to any one of embodiments eighteen through twenty-two is provided, wherein the antigen binding protein comprises:
a. one or more heavy chain complementary determining regions (CDRHs) selected from the group consisting of:
   i. a CDRH1 of SEQ ID NO:23;
   ii. a CDRH2 of SEQ ID NO:24;
   iii. a CDRH3 of SEQ ID NO:25;
   iv. a CDRH of (i), (ii) and (iii) that contains one or more amino acid substitutions, deletions or insertions totaling no more than 4 amino acids;
b. one or more light chain complementary determining regions (CDRLs) selected from the group consisting of:
   i. a CDRL1 of SEQ ID NO:26;
   ii. a CDRL2 of SEQ ID NO:27;
   iii. a CDRL3 of SEQ ID NO:28;
   iv. a CDRL of (i), (ii) and (iii) that contains one or more amino acid substitutions, deletions or insertions totaling no more than 4 amino acids; or
c. one or more CDRHs of (a) and one or more CDRLs of (b).

In a twenty-fourth embodiment, the antigen binding protein according to any one of embodiments eighteen through twenty-two is provided, wherein the antigen binding protein comprises:
  a. a CDRH selected from the group consisting of:
    i. a CDRH1 of SEQ ID NO:23;
    ii. a CDRH2 of SEQ ID NO:24; and
    iii. a CDRH3 of SEQ ID NO:25;
  b. a CDRL selected from the group consisting of:
    i. a CDRL1 of SEQ ID NO:26;
    ii. a CDRL2 of SEQ ID NO:27; and
    iii. a CDRL3 of SEQ ID NO:28; or
  c. one or more CDRHs of (a) and one or more CDRLs of (b).

In a twenty-fifth embodiment, the antigen binding protein according to the previous embodiment is provided, wherein the antigen binding protein comprises: a CDRH1 of SEQ ID NO:23, a CDRH2 of SEQ ID NO:24, a CDRH3 of SEQ ID NO:25; a CDRL1 of SEQ ID NO:26, a CDRL2 of SEQ ID NO:27, and a CDRL3 of SEQ ID NO:28.

In a twenty-sixth embodiment, the antigen binding protein according to any one of embodiments eighteen through twenty-two is provided, wherein the antigen binding protein comprises a heavy chain variable region ($V_H$) and/or a light chain variable region ($V_L$), wherein
  a. the $V_H$ has at least 90% sequence identity with the amino acid sequence selected from the group consisting of SEQ ID NO: 19 and 20; and
  b. the $V_L$ has at least 90% sequence identity with the amino acid sequence selected from the group consisting of SEQ ID NO:21 and 22.

In a twenty-seventh embodiment, the antigen binding protein according to the previous embodiment, wherein the antigen binding protein comprises a heavy chain variable region ($V_H$) and a light chain variable region ($V_L$), wherein
  a. the $V_H$ comprises the amino acid sequence of SEQ ID NO:19 and the $V_L$ comprises the amino acid sequence of SEQ ID NO:21;
  b. the $V_H$ comprises the amino acid sequence of SEQ ID NO:20 and the $V_L$ comprises the amino acid sequence of SEQ ID NO:21;
  c. the $V_H$ comprises the amino acid sequence of SEQ ID NO:19 and the $V_L$ comprises the amino acid sequence of SEQ ID NO:22; or
  d. the $V_H$ comprises the amino acid sequence of SEQ ID NO:20 and the $V_L$ comprises the amino acid sequence of SEQ ID NO:22.

In a twenty-eighth embodiment, the antigen binding protein according to any one of embodiments eighteen through twenty-two is provided, wherein the antigen binding protein comprises a heavy chain (HC) and/or a light chain (LC), wherein
  a. the HC has at least 90% sequence identity with the amino acid sequence selected from the group consisting of SEQ ID NO:15 and 16; and
  b. the LC has at least 90% sequence identity with the amino acid sequence selected from the group consisting of SEQ ID NO: 17 and 18.

In a twenty-ninth embodiment, the antigen binding protein according to the previous embodiment is provided, wherein the antigen binding protein comprises a heavy chain (HC) and a light chain (LC), wherein
  a. the HC comprises the amino acid sequence of SEQ ID NO:15 and the LC comprises the amino acid sequence of SEQ ID NO: 17;
  b. the HC comprises the amino acid sequence of SEQ ID NO:16 and the LC comprises the amino acid sequence of SEQ ID NO:17;
  c. the HC comprises the amino acid sequence of SEQ ID NO:15 and the LC comprises the amino acid sequence of SEQ ID NO: 18; or
  d. the HC comprises the amino acid sequence of SEQ ID NO:16 and the LC comprises the amino acid sequence of SEQ ID NO: 18.

In a thirtieth embodiment, a pharmaceutical composition comprising at least one antigen binding protein according to any one of embodiments eighteen through twenty-nine is provided.

In a thirty-first embodiment, a nucleic acid molecule encoding the antigen binding protein according to any one of embodiments eighteen through twenty-nine is provided.

In a thirty-second embodiment, a vector comprising the nucleic acid of the previous embodiment is provided.

In a thirty-third embodiment, a host cell comprising the nucleic acid of the thirty-first embodiment and/or the vector of the previous embodiment is provided.

In a thirty-fourth embodiment, a method of making the antigen binding protein according to any one of embodiments eighteen through twenty-nine is provided, the method comprising preparing the antigen binding protein from a host cell that secretes the antigen binding protein.

In a thirty-fifth embodiment, the antigen binding protein according to of any one of embodiments eighteen through twenty-nine, or the pharmaceutical composition according to the thirtieth embodiment, is provided for use in therapy.

BRIEF DESCRIPTION OF THE DRAWINGS

FIG. 1 is a plot and bar graph showing the results from a 293/TCF luciferase cell assay demonstrating the inhibitory effect of SFRP5 on Wnt3a-mediated signaling. The plot (FIG. 1A) compares the relative luciferase units upon addition of recombinant human Wnt3a (200 ng/ml) (filled circles), recombinant human Wnt3a (200 ng/ml) plus recombinant human SFRP5 (6 µg/ml; open squares) or vehicle (open triangles). The bar graph (FIG. 1B) shows the inhibition of Wnt3a-mediated signaling upon an increasing concentration of recombinant mouse SFRP5-hemiFc protein. TCF/LEF Reporter (Luc)-HEK293 cell line from BPS Biosciences (San Diego, Calif.). Wnt3a from R&D Systems.

Lep$^{ob}$/J male mice. Each plot shows glucose levels (mg/dL) over a 60 minute period after oral injection of glucose (1 g/kg) in mice treated with an IgG control antibody or subclone 24P2.2, 12E6.2, 24C18.3, or 17O2.1. Mice were treated with 30 mgs/kg of antibody, i.p, two-times per week over the course of the four week study. N=12 for each cohort. 2-way ANOVA statistical significance (asterisks) comparing mice treated with subclone 24C18.3 to IgG control mice is shown.

FIG. 5 is a series of four bar graphs showing the results of fasting blood glucose levels (FIG. 5A), fasting serum insulin levels (FIG. 5B), body weight (FIG. 5C), and fasting triglyceride levels (FIG. 5D) over time after injection into 6 week old B6.V-Lep$^{ob}$/J male mice. Each bar graph shows results for mice treated with an IgG control antibody or subclone 24P2.2, 12E6.2, 24C18.3, or 17O2.1. Mice were treated with 30 mgs/kg of antibody, i.p, two-times per week over the course of the four week study. N=12 for each cohort. 2-way ANOVA statistical significance (asterisks) comparing mice treated with a subclone to IgG control mice.

Figure 6:
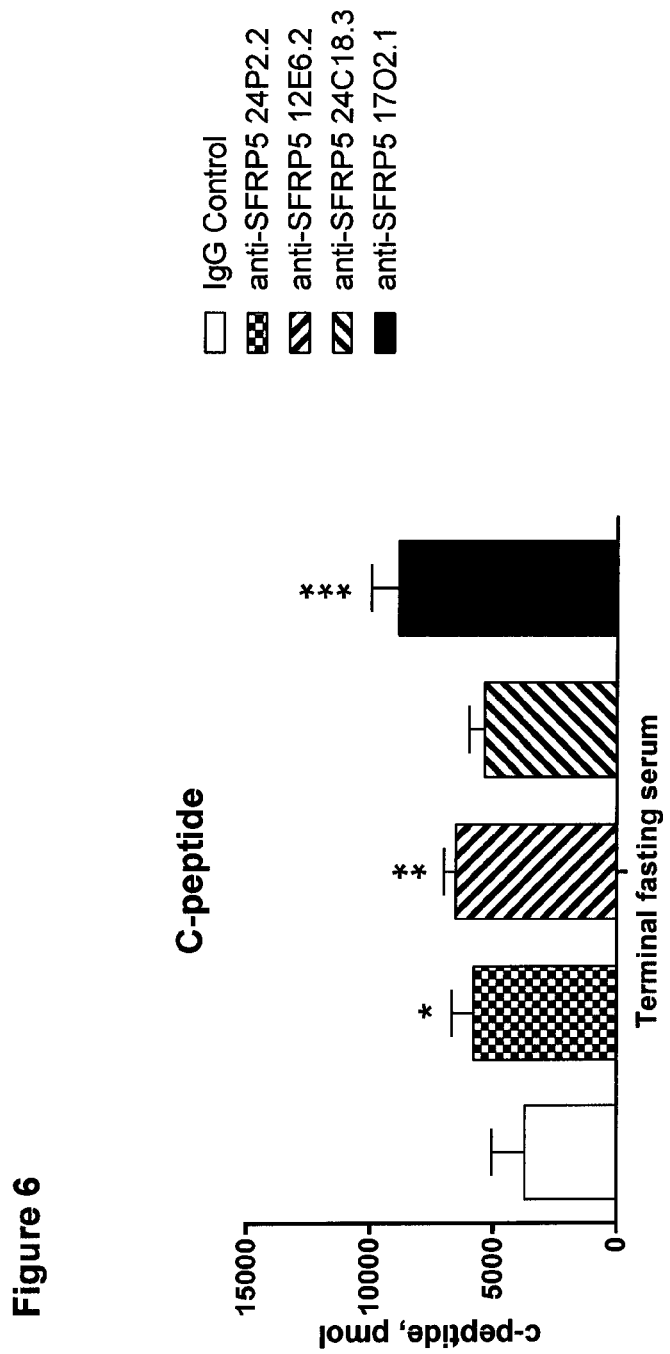

FIG. 6 is a bar graph showing the results of fasting c-peptide levels 4 weeks after treatment. Results are shown for mice treated with an IgG control antibody or subclone 24P2.2, 12E6.2, 24C18.3, or 17O2.1. Mice were treated with 30 mgs/kg of antibody, i.p, two-times per week over the course of the four week study. N=12 for each cohort. 2-way ANOVA statistical significance (asterisks) comparing mice treated with a subclone to IgG control mice is shown.

FIG. 7 is a series of plots and a bar graph showing the effects of SFRP5 overexpression in BDF-DIO (FIG. 7A-F) and BDF-lean (FIG. 7G-H) mice. The first series of plots show the results of glucose tolerance tests performed at week 2 (FIG. 7A), week 4 (FIG. 7B) and week 6 (FIG. 7C) after AAV injection into 12 week old BDF-DIO males mice. Each plot shows glucose levels (mg/dL) over a 60 minute period after oral injection of glucose (2 g/kg) into 4 hour fasted AAV-SFRP5 mice (n=15) and AAV-empty vector mice (n=15). Metabolic parameters were measured over time, including body weight (FIG. 7D), fasting blood glucose (FIG. 7E), and fasting insulin (FIG. 7F). A glucose tolerance test was performed in BDF-lean mice 2 weeks after AAV injection (FIG. 7G). The plot shows glucose levels (mg/dL) over a 60 minute period after oral injection of glucose (2 g/kg) into 4 hour fasted AAV-SFRP5 mice (n=11) and AAV-empty vector (control) mice (n=13). The area under the curve is presented (FIG. 7H). AAV viral vectors were injected intravenously at 8×10$^{12}$ viral particles per mouse in saline (BDF-DIO mice) or at 1.6E12 viral particles per mouse in saline (BDF-lean mice). 2-way ANOVA statistical significance (asterisks) comparing AAV-SFRP5 mice to AAV-empty vector mice. Standard error of the mean is shown. BDF-DIO mice were fed a 60% high fat diet for at least 7 weeks prior AAV injections.

Figure 8:
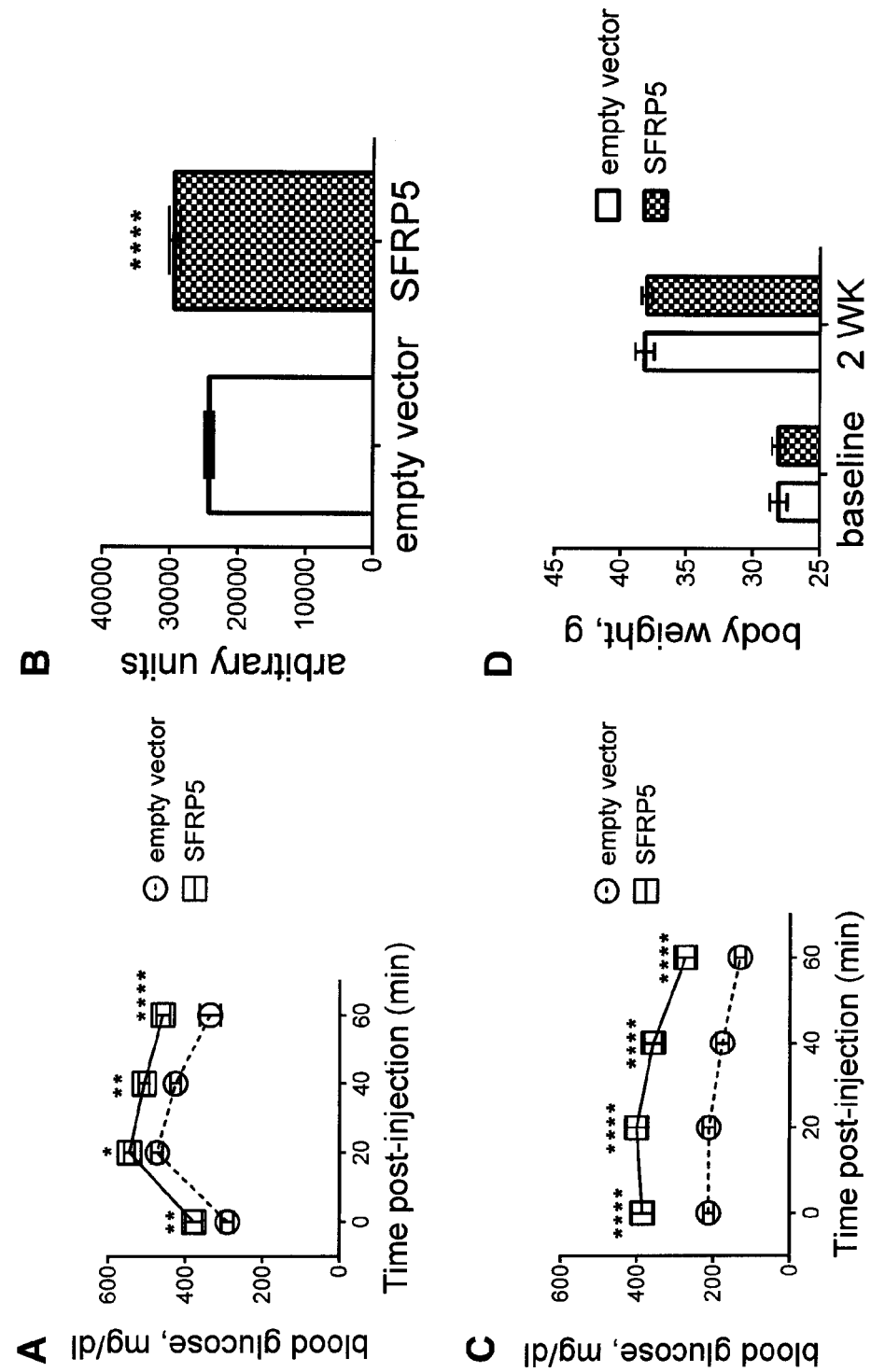
Figure 8:
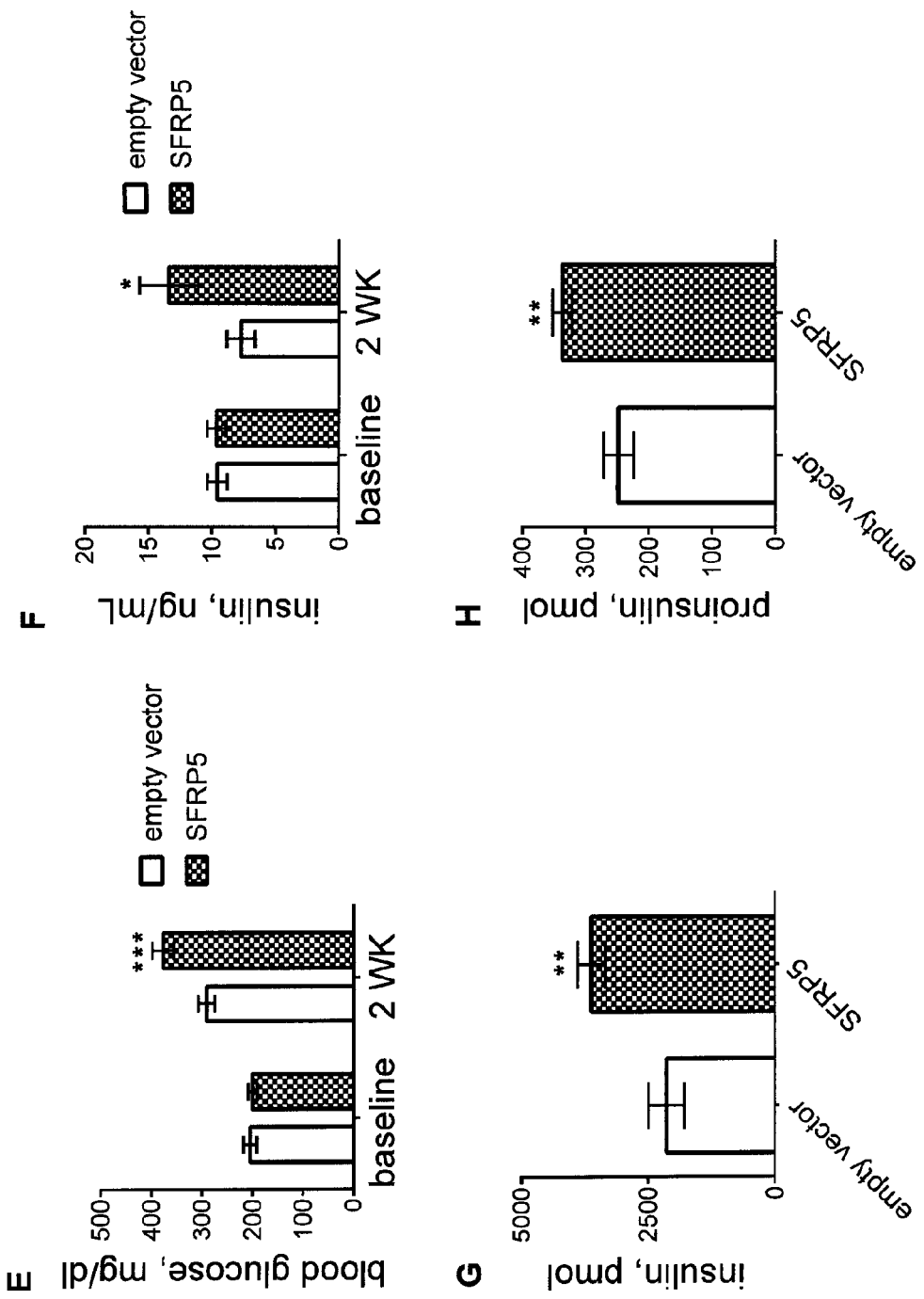

FIG. 8 is a series of plots and bar graphs showing the effects of SFRP5 over-expression in B6.V-Lep$^{ob}$/J male mice. The first plot (FIG. 8A) shows glucose levels (mg/dL) over a 60 minute period after oral injection of glucose (1 g/kg) into 4 hour fasted AAV-SFRP5 mice (n=17) and AAV-empty vector mice (n=15), 2 weeks after AAV injection. The first bar graph (FIG. 8B) shows the area under the curve for the glucose tolerance test. An insulin tolerance test was performed after 3 weeks post-AAV injection. Insulin (5 units/kg) was injected into mice fasted for 4 hours and blood glucose levels (mg/dL) were measured over a 60 minute period (FIG. 8C). Metabolic parameters were measured over time, including body weight (FIG. 8D), fasting blood glucose (FIG. 8E), and fasting insulin (FIG. 8F). The two final bar graphs show serum insulin (FIG. 8G) and serum proinsulin (FIG. 8H) levels 2 weeks after AAV injection. AAV viral vectors were injected intravenously at 4×10$^{12}$ viral particles per mouse in saline. Mice were 6 weeks old at the time of AAV injection. 2-way ANOVA statistical significance (asterisks) comparing AAV-SFRP5 mice to AAV-empty vector mice (FIGS. 8A-F) and 2-tailed, unpaired t-test (asterisks) comparing AAV-SFRP5 mice to AAV-empty vector mice (FIGS. 8G-H). Standard error of the mean is shown.

Figure 9:
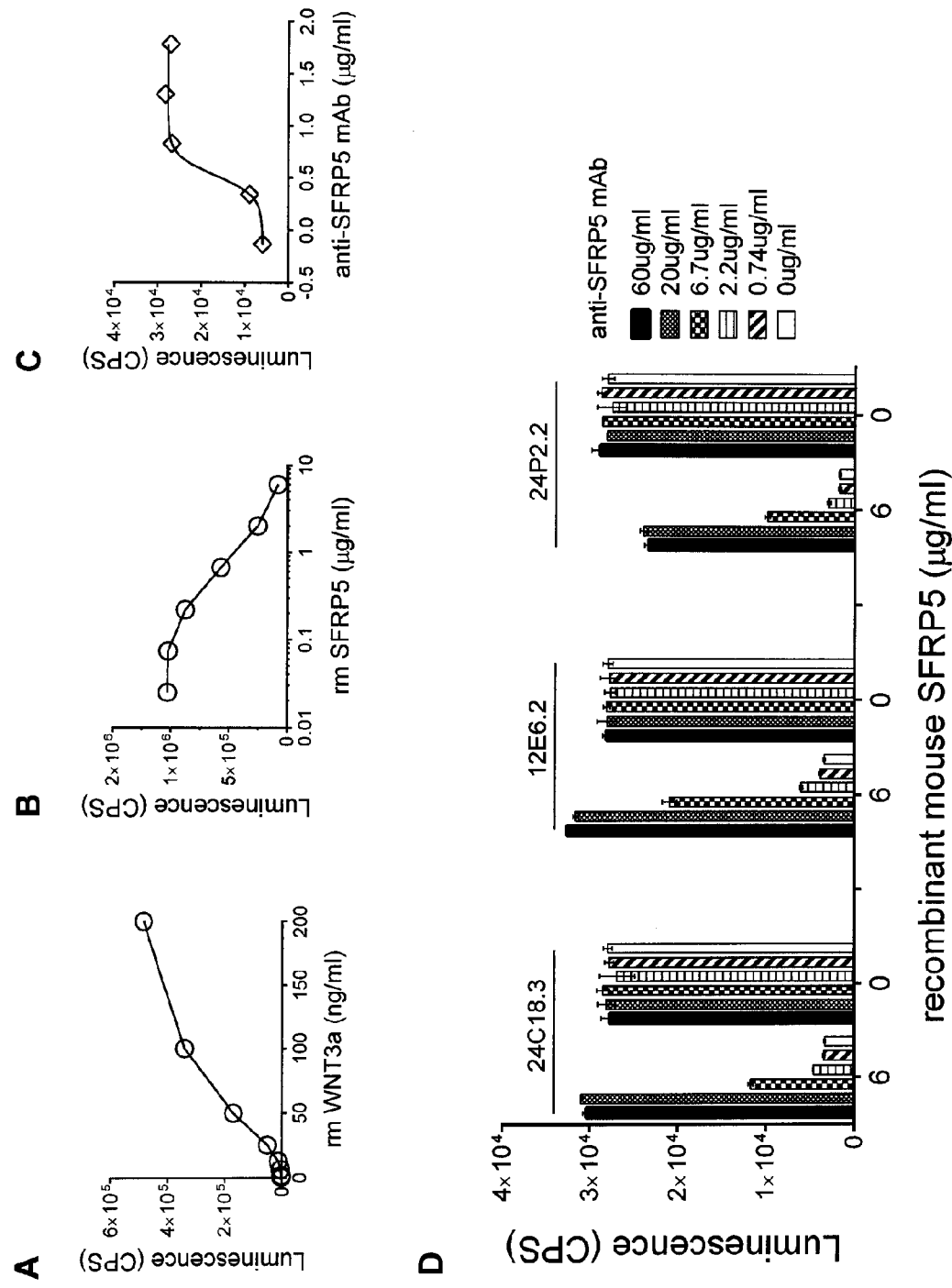

FIG. 9 is a series of plots and a bar graph showing the results from 293/TCF luciferase cell assays demonstrating the inhibitory effect of anti-SFRP5 monoclonal antibody on the inhibition of WNT3a-mediated signaling by SFRP5 recombinant protein. Relative luciferase units correlate with the addition of increasing recombinant human WNT3a added to 293/TCF cells (FIG. 9A). The addition of increasing amounts of recombinant SFRP5 added to WNT3a (180 ng/ml) inhibits WNT3a-mediated signaling (FIG. 9B). The addition of anti-SFRP5 (clone 24C18.3) to cells treated with both WNT3a (180 ng/ml) and recombinant SFRP5 (6 ug/ml) rescues the stimulatory effect of WNT3a on 293/TCF cells in a dose-dependent manner (FIG. 9C). Anti-SFRP5 monoclonal antibody clones, 24C18.3, 12E6.2 and 24P.2, were compared for their ability to inhibit SFRP5-mediated inhibition of WNT3a on 293/TCF cells (FIG. 9D). Standard error of the mean is shown. TCF/LEF Reporter (Luc)-HEK293 cell line from BPS Biosciences (San Diego, Calif.). Recombinant mouse WNT3a and SFRP5 from R&D Systems.

Figure 10:
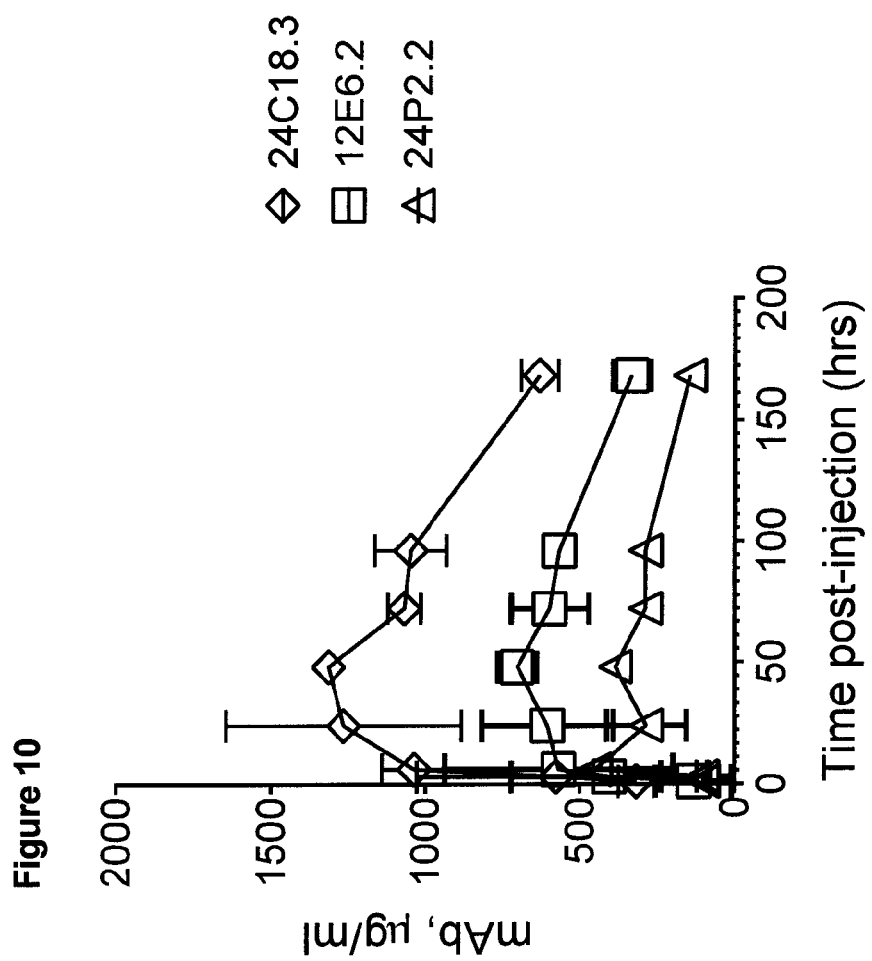

FIG. 10 is a plot for the in vivo study evaluating the pharmacokinetic properties of anti-SFRP5 monoclonal antibody clones 24C18.3, 12E6.2 and 24P2.2. B6.V-Lep$^{ob}$/J male mice (3 each for each time point) were injected intraperitoneally with one of the anti-SFRP5 monoclonal antibody clones. Blood was collected before injection (0) and 1, 3, 6, 24, 48, 72, 96 and 168 hours post injection. The plot shows the concentration of monoclonal antibody in the blood at each time point. Concentrations were determined by ELISA using recombinant mouse SFRP5 to coat plates. Standard deviation is shown.

Figure 11:
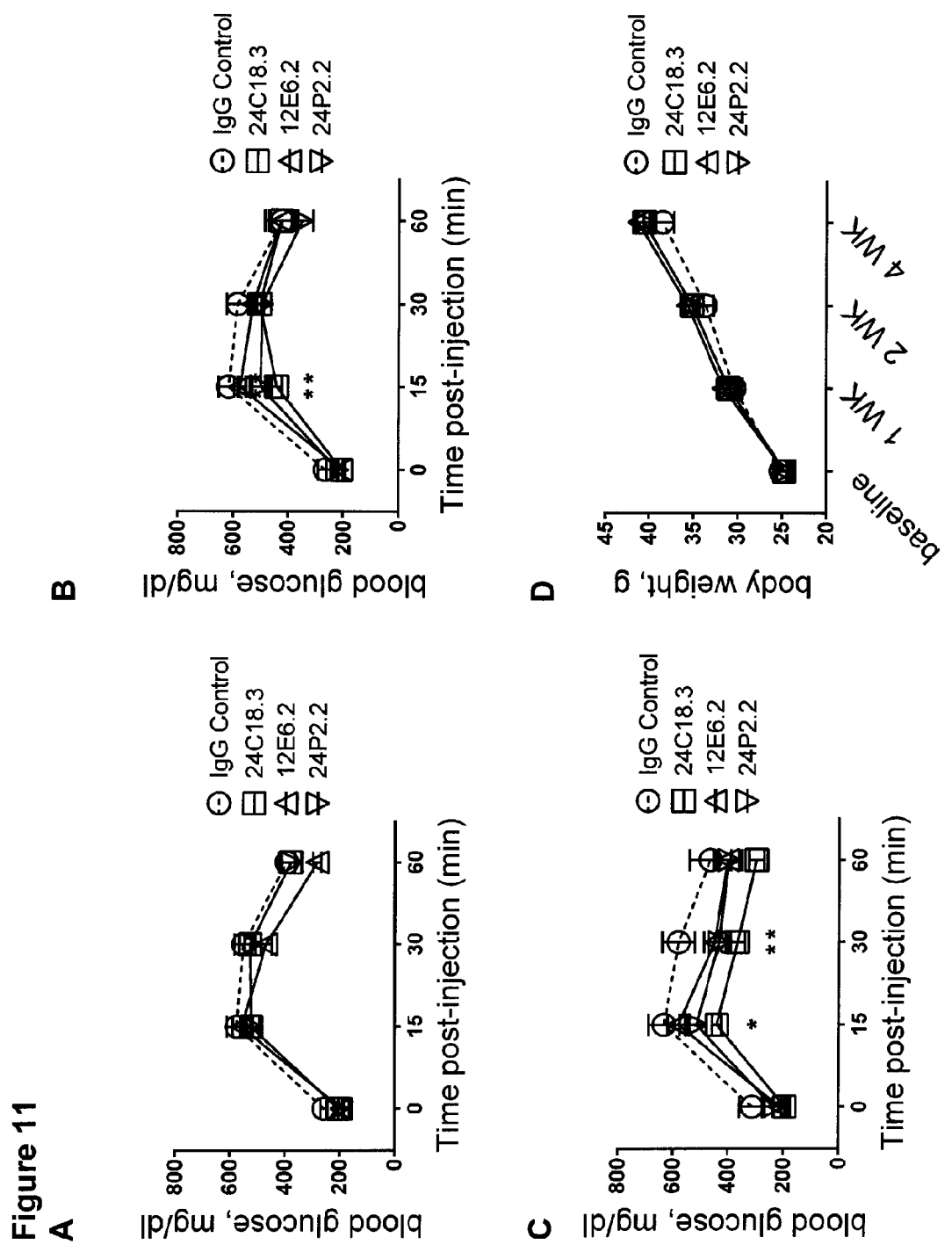
Figure 11:
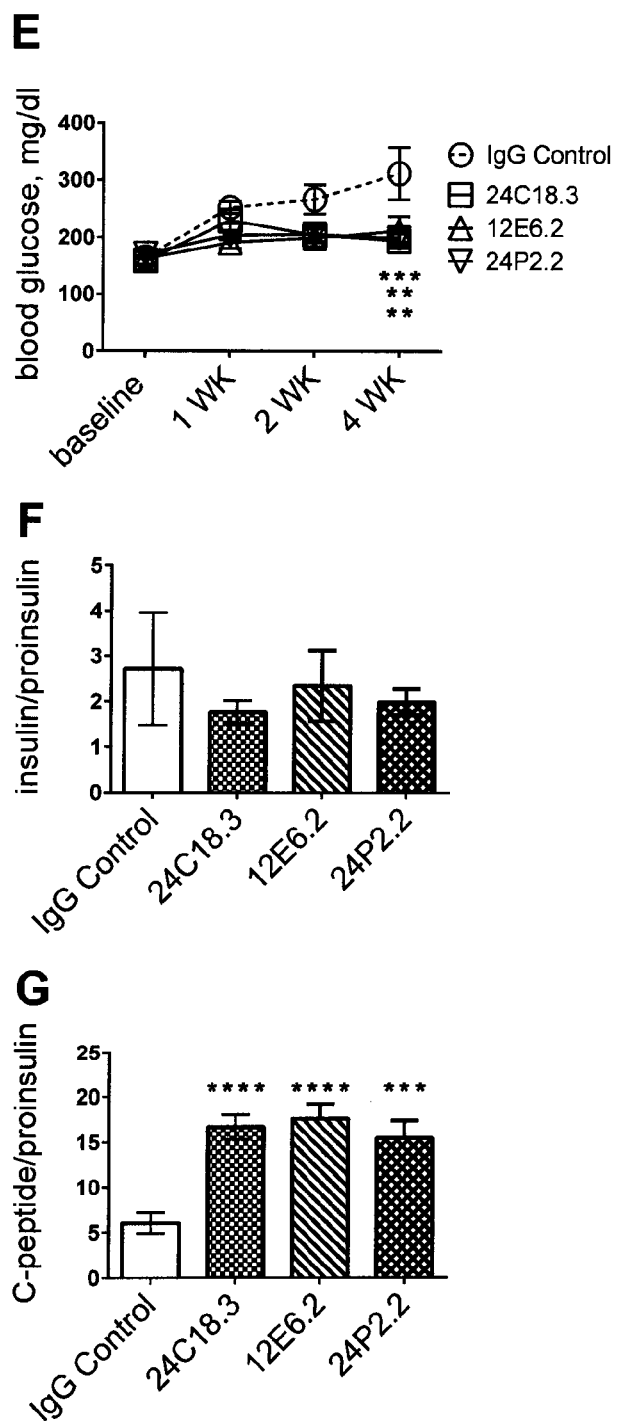

FIG. 11 is a series of plots and graphs showing the effects of anti-SFRP5 monoclonal antibody treatment in B6.V-Lep$^{bb}$/J male mice. 6 week old B6.V-Lep$^{ob}$/J male mice were injected with an IgG control antibody or one of the 3 anti-SFRP5 monoclonal antibody clones; 24C18.3, 12E6.1 or 24P2.2. Glucose tolerance tests were performed at week 1 (FIG. 11A), week 2 (FIG. 11B) and week 4 (FIG. 11C). Each plot shows glucose levels (mg/dL) over a 60 minute period after oral injection of glucose (1 g/kg for week 1, 2 g/kg for weeks 2 and 4). Plots for body weight over time (FIG. 11D) and fasting blood glucose levels (FIG. 11E) are shown. Bar graphs show the ratio of insulin to proinsulin (FIG. 11F) and C-peptide to proinsulin (FIG. 11G) present in the serum of 4 hour fasted mice upon harvest at week 5. Mice were treated with 30 mgs/kg of antibody, intraperitoneally, two-times per week over the course of the study. N=12 for each cohort. 2-way ANOVA statistical significance (asterisks) comparing mice treated with anti-SFRP5 monoclonal antibody to IgG control mice. Standard error of the mean is shown.

FIG. 12 is a plot and 2 bar graphs showing the effect of anti-SFRP5 monoclonal antibody clone, 24C18.3, on C57BL/6J male mice. 20 week old C57BL/6J male mice fed a 60% high fat diet for at least 8 weeks were injected with an IgG control antibody (30 mgs/kg) or anti-SFRP5 monoclonal antibody clone, 24C18.3 (30 mgs/kg or 3 mgs/kg). A glucose tolerance test was performed at week 2 on 4 hour fasted mice (FIG. 12A). The plot shows glucose levels (mg/dL) over a 60 minute period after oral injection of glucose (2 g/kg). The first bar graphs (FIG. 12B) shows the ratio of C-peptide to proinsulin in the serum of IgG-treated mice (30 mgs/kg) compared to 24C18.3-treated mice (30 mgs/kg). The second bar graphs (FIG. 12C) shows the ratio of C-peptide to proinsulin content in the pancreas of IgG-treated mice (30 mgs/kg) compared to 24C18.3-treated mice (30 mgs/kg). Hormone content was normalized to total protein content. Mice were treated with 30 mgs/kg or 3 mgs/kg (as indicated) of antibody, intraperitoneally, two-times per week over the course of the study. N=12 for each cohort. 2-way ANOVA statistical significance (asterisks) comparing mice treated with anti-SFRP5 monoclonal antibody to IgG control mice. Standard error of the mean is shown.

DETAILED DESCRIPTION OF THE INVENTION

The present disclosure provides a method of treating a metabolic disorder, such as a disorder of glucose metabolism (e.g., Type 2 diabetes, elevated glucose levels, elevated insulin levels, dyslipidemia, metabolic syndrome (Syndrome X or insulin resistance syndrome), glucosuria, metabolic acidosis, diabetic neuropathy, diabetic nephropathy, diabetic retinopathy, diabetic cardiomyopathy, Type 1 diabetes, obesity and conditions exacerbated by obesity) by blocking or interfering with the biological activity of SFRP5. In one embodiment, a therapeutically effective amount of an isolated human SFRP5 binding protein is administered to a subject in need thereof. Methods of administration and delivery are also provided.

The section headings used herein are for organizational purposes only and are not to be construed as limiting the subject matter described.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present application are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001), Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

It should be understood that this invention is not limited to the particular methodology, protocols, and reagents, etc., described herein and as such may vary. The terminology used herein is for the purpose of describing particular embodiments only, and is not intended to limit the scope of the disclosed, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

I. General Definitions

Following convention, as used herein "a" and "an" mean "one or more" unless specifically indicated otherwise.

As used herein, the term "SFRP5" (or "SFRP5 polypeptide" or "SFRP5 protein") refers to a naturally-occurring wild-type SFRP5 polypeptide expressed in a mammal, such as a human or a mouse (e.g., SEQ ID NO:1, 3, 5 or 7), and includes naturally occurring alleles (e.g., naturally occurring allelic forms of human SFRP5 protein). It will be appreciated that human SFRP5 may herein be referred to by the prefix "h" or "hu" (e.g., "huSFRP5"), and murine SFRP5 may herein be referred to by the prefix "m" or "mu" (e.g., "muSFRP5"). The term "SFRP5" (or "SFRP5 polypeptide" or "SFRP5 protein") also encompasses a SFRP5 polypeptide in which a naturally occurring SFRP5 polypeptide sequence has been modified. Such modifications include, but are not limited to, one or more amino acid substitutions, including substitutions with non-naturally occurring amino acids non-naturally-occurring amino acid analogs and amino acid mimetics.

In various embodiments, a SFRP5 polypeptide comprises an amino acid sequence that is at least about 85 percent identical to a naturally-occurring SFRP5 polypeptide (e.g., SEQ ID NO:1, 3, 5 or 7). In other embodiments, a SFRP5 polypeptide comprises an amino acid sequence that is at least about 90 percent, or about 95, 96, 97, 98, or 99 percent identical to a naturally-occurring SFRP5 polypeptide amino acid sequence (e.g., SEQ ID NO:1, 3, 5 or 7). The present invention also encompasses nucleic acid molecules encoding such SFRP5 polypeptide sequences.

The amount of SFRP5 or SFRP5 activity can be determined in various ways. The mass of SFRP5 can be determined by a competitive double antibody radioimmunoassay, or ELISA. The presence of SFRP5 in serum can be determined by Western Blot analysis. In addition, a number of cell-based assays for SFRP5 activity have been reported. See, e.g., Su et al., 2009, *Int. J. Cancer,* 127:555-567; Ouchi et al., 2010, *Science,* 329:454-457 and supporting online material (http://www.sciencemag.org/content/suppl/2010/06/17/science.1188280.DC1).

An "antigen binding protein" as used herein means any protein that specifically binds a specified target antigen, such as a SFRP5 polypeptide (e.g., a human SFRP5 polypeptide such as provided in SEQ ID NO: 1 or 3). The term encompasses intact antibodies that comprise at least two full-length heavy chains and two full-length light chains, as well as derivatives, variants, fragments, and mutations thereof, examples of which include Fab, Fab', F(ab')$_2$, and Fv fragments. An antigen binding protein also includes domain antibodies such as nanobodies and single-chain antibodies as described further below.

In general, a SFRP5 antigen binding protein is said to "specifically bind" its target antigen SFRP5 when the antigen binding protein exhibits essentially background binding to non-SFRP5 molecules. An antigen binding protein that specifically binds SFRP5 may, however, cross-react with SFRP5 polypeptides from different species. Typically, a SFRP5 antigen binding protein specifically binds human SFRP5 when the dissociation constant ($K_D$) is $\leq 10^{-7}$ M as measured via a surface plasma resonance technique (e.g., BIACore, GE-Healthcare Uppsala, Sweden). A SFRP5 antigen binding protein specifically binds human SFRP5 with "high affinity" when the $K_D$ is $\leq 5 \times 10^{-8}$ M, and with "very high affinity" when the $K_D$ is $\leq 5 \times 10^{-9}$ M, as measured using methods described.

"Antigen binding region" means a protein, or a portion of a protein, that specifically binds a specified antigen. For example, that portion of an antigen binding protein that contains the amino acid residues that interact with an antigen and confer on the antigen binding protein its specificity and affinity for the antigen is referred to as "antigen binding region." An antigen binding region typically includes one or more "complementary binding regions" ("CDRs"). Certain antigen binding regions also include one or more "framework" regions. A "CDR" is an amino acid sequence that contributes to antigen binding specificity and affinity. "Framework" regions can aid in maintaining the proper conformation of the CDRs to promote binding between the antigen binding region and an antigen.

A "recombinant protein", including a recombinant SFRP5 antigen binding protein, is a protein made using recombinant techniques, i.e., through the expression of a recombinant nucleic acid as described herein. Methods and techniques for the production of recombinant proteins are well known in the art.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" as such is a species of an antigen binding protein. An intact antibody generally will comprise at least two full-length heavy chains and two full-length light chains, but in some instances may include fewer chains such as antibodies naturally occurring in camelids which may comprise only heavy chains. Antibodies may be derived solely from a single source, or may be "chimeric," that is, different portions of the antibody may be derived from two different antibodies as described further below. The antigen binding proteins, antibodies, or binding fragments may be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and mutations thereof, examples of which include Fab, Fab', F(ab')$_2$, Fv fragments, domain antibodies such as Nanobodies® and single-chain antibodies as described in more detail below.

The term "light chain" as used with respect to an antibody or fragments thereof includes a full-length light chain and fragments thereof having sufficient variable region sequence to confer binding specificity. A full-length light chain includes a variable region domain, $V_L$, and a constant region domain. $C_L$. The variable region domain of the light chain is at the amino-terminus of the polypeptide. Light chains include kappa chains and lambda chains.

The term "heavy chain" as used with respect to an antibody or fragment thereof includes a full-length heavy chain and fragments thereof having sufficient variable region sequence to confer binding specificity. A full-length heavy chain includes a variable region domain, $V_H$, and three constant region domains, $C_H1$, $C_H2$, and $C_H3$. The $V_H$ domain is at the amino-terminus of the polypeptide, and the $C_H$ domains are at the carboxyl-terminus, with the $C_H3$ being closest to the carboxy-terminus of the polypeptide. Heavy chains may be of any isotype, including IgG (including IgG1, IgG2, IgG3 and IgG4 subtypes), IgA (including IgA1 and IgA2 subtypes), IgM and IgE.

The term "immunologically functional fragment" (or simply "fragment") of an antibody or immunoglobulin chain (heavy or light chain), as used herein, is an antigen binding protein comprising a portion (regardless of how that portion is obtained or synthesized) of an antibody that lacks at least some of the amino acids present in a full-length chain but which is capable of specifically binding to an antigen. Such fragments are biologically active in that they bind specifically to the target antigen and can compete with other antigen binding proteins, including intact antibodies, for specific binding to a given epitope. In one aspect, such a fragment will retain at least one CDR present in the full-length light or heavy chain, and in some embodiments will comprise a single heavy chain and/or light chain or portion thereof. These biologically active fragments may be produced by recombinant DNA techniques, or may be produced by enzymatic or chemical cleavage of antigen binding proteins, including intact antibodies. Immunologically functional immunoglobulin fragments include, but are not limited to, Fab, Fab', F(ab')$_2$, Fv, domain antibodies and single-chain antibodies, and may be derived from any mammalian source, including but not limited to human, mouse, rat, camelids or rabbit. It is contemplated further that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life.

An "Fab fragment" is comprised of one light chain and the CH1 and variable regions of one heavy chain. The heavy chain of a Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

An "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form an F(ab')$_2$ molecule.

An "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. No. 4,946,778 and U.S. Pat. No. 5,260,203, the disclosures of which are incorporated by reference.

A "domain antibody" is an immunologically functional immunoglobulin fragment containing only the variable region of a heavy chain or the variable region of a light chain. Examples of domain antibodies include Nanobodies®. In some instances, two or more $V_H$ regions are covalently joined with a peptide linker to create a bivalent domain antibody. The two $V_H$ regions of a bivalent domain antibody may target the same or different antigens.

A "bivalent antigen binding protein" or "bivalent antibody" comprises two antigen binding regions. In some instances, the two binding regions have the same antigen specificities. Bivalent antigen binding proteins and bivalent antibodies may be bispecific, see, infra.

A multispecific antigen binding protein" or "multispecific antibody" is one that targets more than one antigen or epitope.

A "bispecific," "dual-specific" or "bifunctional" antigen binding protein or antibody is a hybrid antigen binding protein or antibody, respectively, having two different antigen binding sites. Bispecific antigen binding proteins and antibodies are a species of multispecific antigen binding protein or multispecific antibody and may be produced by a variety of methods including, but not limited to, fusion of hybridomas or linking of Fab' fragments. See, e.g., Songsivilai and Lachmann, 1990. *Clin. Exp. Immunol.* 79:315-321; Kostelny et al., 1992, *J. Inmunol.* 148:1547-1553. The two binding sites of a bispecific antigen binding protein or antibody will bind to two different epitopes, which may reside on the same or different protein targets.

The term "compete" when used in the context of antigen binding proteins (e.g., antibodies) that compete for the same epitope means competition between antigen binding proteins is determined by an assay in which the antigen binding protein (e.g., antibody or immunologically functional fragment thereof) under test prevents or inhibits specific binding of a reference antigen binding protein to a common antigen (e.g., SFRP5 or a fragment thereof). Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, *Methods in Enzymology* 2:242-253); solid phase direct biotin-avidin EIA (see, e.g., Kirkland et al., 1986, *J. Inmunol.* 137:3614-3619) solid phase direct labeled assay, solid phase direct labeled sandwich assay (see, e.g., Harlow and Lane, 1988, *Antibodies, A Laboratory Manual*, Cold Spring Harbor Press); solid phase direct label RIA using 1-125 label (see, e.g., Morel et al., 1988, *Molec. Immunol.* 25:7-15); solid phase direct biotin-avidin EIA (see, e.g., Cheung, et al., 1990, *Virology* 176:546-552); and direct labeled RIA (Moldenhauer et al., 1990, *Scand. J. Immunol.* 32:77-82). Typically, such an assay involves the use of purified antigen bound to a solid surface or cells bearing either of these, an unlabelled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the Examples herein. Usually, when a competing antigen binding protein is present in excess, it will inhibit specific binding of a reference antigen binding protein to a common antigen by at least 40%, 45%, 50%, 55%, 60%, 65%, 70% or 75%. In some instances, binding is inhibited by at least 80%, 85%, 90%, 95%, or 97% or more.

The term "antigen" refers to a molecule or a portion of a molecule capable of being bound by a selective binding agent, such as an antigen binding protein (including, e.g., an antibody), and additionally capable of being used in an animal to produce antibodies capable of binding to that antigen. An antigen may possess one or more epitopes that are capable of interacting with different antigen binding proteins, e.g., antibodies.

The term "epitope" is the portion of a molecule that is bound by an antigen binding protein (for example, an antibody). The term includes any determinant capable of specifically binding to an antigen binding protein, such as an antibody. An epitope can be contiguous or non-contiguous (discontinuous) (e.g., in a polypeptide, amino acid residues that are not contiguous to one another in the polypeptide sequence but that within in context of the molecule are bound by the antigen binding protein). A conformational epitope is an epitope that exists within the conformation of an active protein but is not present in a denatured protein. In certain embodiments, epitopes may be mimetic in that they comprise a three dimensional structure that is similar to an epitope used to generate the antigen binding protein, yet comprise none or only some of the amino acid residues found in that epitope used to generate the antigen binding protein. Most often, epitopes reside on proteins, but in some instances may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Generally, antigen binding proteins specific for a particular target antigen will preferentially recognize an epitope on the target antigen in a complex mixture of proteins and/or macromolecules.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in *Computational Molecular Biology*, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, *SIAM J. Applied Math.* 48:1073.

In calculating percent identity, the sequences being compared are aligned in a way that gives the largest match between the sequences. The computer program used to determine percent identity is the GCG program package, which includes GAP (Devereux et al., 1984, *Nucl. Acid Res.* 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, *Atlas of Protein Sequence and Structure* 5:345-352 for the PAM 250 comparison matrix; Henikoff et al., 1992, *Proc. Natl. Acad. Sci. U.S.A.* 89:10915-10919 for the BLOSUM 62 comparison matrix) is also used by the algorithm.

Recommended parameters for determining percent identity for polypeptides or nucleotide sequences using the GAP program are the following:
Algorithm: Needleman et al., 1970, *J. Mol. Biol.* 48:443-453;
Comparison matrix: BLOSUM 62 from Henikoff et al., 1992, supra;
Gap Penalty: 12 (but with no penalty for end gaps)
Gap Length Penalty: 4
Threshold of Similarity: 0.

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, or 99% of all macromolecular species present in the composition. In other embodiments, the object species is purified to essential homogeneity wherein contaminating species cannot be detected in the composition by conventional detection methods and thus the composition consists of a single detectable macromolecular species.

The terms "treat" and "treating" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods presented herein successfully treat cardiovascular disease such as atherosclerosis by decreasing the incidence of cardiovascular disease, causing remission of cardiovascular disease and/or ameliorating a symptom associated with cardiovascular disease.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with the disease state (e.g., diabetes, obesity, dyslipidemia, elevated glucose levels, elevated insulin levels or diabetic nephropathy. In some embodiments, the effective amount is a therapeutically effective amount or a prophylactically effective amount. A "therapeutically effective amount" is an amount sufficient to remedy a disease state (e.g. atherosclerosis) or symptoms, particularly a state or symptoms associated with the disease state, or otherwise prevent, hinder, retard or reverse the progression of the disease state or any other undesirable symptom associated with the disease in any way whatsoever. A "prophylactically effective amount" is an amount of a pharmaceutical composition that, when administered to a subject, will have the intended prophylactic effect, e.g., preventing or delaying the onset (or reoccurrence) of the disease state, or reducing the likelihood of the onset (or reoccurrence) of the disease state or associated symptoms. The full therapeutic or prophylactic effect does not necessarily occur by administration of one dose, and may occur only after administration of a series of doses. Thus, a therapeutically or prophylactically effective amount may be administered in one or more administrations.

The terms "therapeutically effective dose" and "therapeutically effective amount," as used herein, means an amount of a SFRP5 binding protein that elicits a biological or medicinal response in a tissue system, animal, or human being sought by a researcher, physician, or other clinician, which includes alleviation or amelioration of the symptoms of the disease or disorder being treated, i.e., an amount of a SFRP5 binding protein that supports an observable level of one or more desired biological or medicinal response, for example lowering blood glucose, insulin, triglyceride, or cholesterol levels; reducing body weight; or improving glucose tolerance, energy expenditure, or insulin sensitivity.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. The modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate. The term "encoding" refers to a polynucleotide sequence encoding one or more amino acids. The term does not require a start or stop codon. An amino acid sequence can be encoded in any one of six different reading frames provided by a polynucleotide sequence.

The term "oligonucleotide" means a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides may be sense or antisense oligonucleotides. An oligonucleotide can include a label, including a radiolabel, a fluorescent label, a hapten or an antigenic label, for detection assays. Oligonucleotides may be used, for example, as PCR primers, cloning primers or hybridization probes.

An "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty other proteins or portions thereof, or may include operably linked regulatory sequences that control expression of the coding region of the recited nucleic acid sequences, and/or may include vector sequences.

Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The term "control sequence" refers to a polynucleotide sequence that can affect the expression and processing of coding sequences to which it is ligated. The nature of such control sequences may depend upon the host organism. In particular embodiments, control sequences for prokaryotes may include a promoter, a ribosomal binding site, and a transcription termination sequence. For example, control sequences for eukaryotes may include promoters comprising one or a plurality of recognition sites for transcription factors, transcription enhancer sequences, and transcription termination sequences. "Control sequences" can include leader sequences and/or fusion partner sequences.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

As used herein, "operably linked" means that the components to which the term is applied are in a relationship that allows them to carry out their inherent functions under suitable conditions. For example, a control sequence in a vector that is "operably linked" to a protein coding sequence is ligated thereto so that expression of the protein coding sequence is achieved under conditions compatible with the transcriptional activity of the control sequences.

The term "host cell" means a cell that has been transformed with a nucleic acid sequence and thereby expresses a gene of interest. The term includes the progeny of the parent cell, whether or not the progeny is identical in morphology or in genetic make-up to the original parent cell, so long as the gene of interest is present.

The terms "polypeptide" or "protein" are used interchangeably herein to refer to a polymer of amino acid residues. The terms also apply to amino acid polymers in which one or more amino acid residues is an analog or mimetic of a corresponding naturally occurring amino acid, as well as to naturally occurring amino acid polymers. The terms can also encompass amino acid polymers that have been modified, e.g., by the addition of carbohydrate residues to form glycoproteins, or phosphorylated. Polypeptides and proteins can be produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The terms "polypeptide" and "protein" specifically encompass SFRP5 antigen binding proteins, antibodies, and/or sequences that have deletions from, additions to, and/or substitutions of one or more amino acids of an antigen-binding protein. The term "polypeptide fragment" refers to a polypeptide that has an amino-terminal deletion, a carboxyl-terminal deletion, and/or an internal deletion as compared with the full-length protein. Such fragments may also contain modified amino acids as compared with the full-length protein. In certain embodiments, fragments are about five to 500 amino acids long. For example, fragments may be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a SFRP5 antibody, useful fragments include but are not limited to a CDR region, a variable domain of a heavy or light chain, a portion of an antibody chain or just its variable region including two CDRs, and the like.

The term "isolated protein" means that a subject protein (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an "isolated protein" constitutes at least about 5%, at least about 10%, at least about 25%, or at least about 50% of a given sample. Genomic DNA, cDNA, mRNA or other RNA, of synthetic origin, or any combination thereof may encode such an isolated protein. Preferably, the isolated protein is substantially free from proteins or polypeptides or other contaminants that are found in its natural environment that would interfere with its therapeutic, diagnostic, prophylactic, research or other use.

A "variant" of a polypeptide (e.g., an antigen binding protein such as an antibody) comprises an amino acid sequence wherein one or more amino acid residues are inserted into, deleted from and/or substituted into the amino acid sequence relative to another polypeptide sequence. Variants include fusion proteins.

A "derivative" of a polypeptide is a polypeptide (e.g., an antigen binding protein such as an antibody) that has been chemically modified in some manner distinct from insertion, deletion, or substitution variants, e.g., via conjugation to another chemical moiety.

The term "naturally occurring" as used throughout the specification in connection with biological materials such as polypeptides, nucleic acids, host cells, and the like, refers to materials which are found in nature.

"Amino acid" includes its normal meaning in the art. The twenty naturally-occurring amino acids and their abbreviations follow conventional usage. See, Immunology—A Synthesis, 2nd Edition, (E. S. Golub and D. R. Green, eds.), Sinauer Associates: Sunderland, Mass. (1991), incorporated herein by reference for any purpose. Stereoisomers (e.g., D-amino acids) of the twenty conventional amino acids, unnatural amino acids such as [alpha]-, [alpha]-disubstituted amino acids. N-alkyl amino acids, and other unconventional amino acids may also be suitable components for polypeptides and are included in the phrase "amino acid." Examples of unconventional amino acids include: 4-hydroxyproline, [gamma]-carboxyglutamate, [epsilon]-N,N,N-trimethyllysine, [epsilon]-N-acetyllysine, 0-phosphoserine, N-acetylserine, N-formylmethionine, 3-methylhistidine, 5-hydroxylysine, [sigma]-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

A "subject" or "patient" as used herein can be any mammal. In a typical embodiment, the subject or patient is a human.

II. SFRP5 Polypeptides and Nucleic Acids

As disclosed herein, a SFRP5 polypeptide can be engineered and/or produced using standard molecular biology methodology. In various examples, a nucleic acid sequence encoding a SFRP5, which can comprise all or a portion of SEQ ID NO:1, 3, 5 or 7, can be isolated and/or amplified from genomic DNA, or cDNA using appropriate oligonucleotide primers. Primers can be designed based on the nucleic and amino acid sequences provided herein according to standard (RT)-PCR amplification techniques. The amplified SFRP5 nucleic acid can then be cloned into a suitable vector and characterized by DNA sequence analysis.

Oligonucleotides for use as probes in isolating or amplifying all or a portion of the SFRP5 sequences provided herein can be designed and generated using standard synthetic techniques, e.g., automated DNA synthesis apparatus, or can be isolated from a longer sequence of DNA.

II.A. Naturally-Occurring and Variant SFRP5 Polypeptide and Polynucleotide Sequences In vivo, SFRP5 is expressed as a contiguous amino acid sequence comprising a signal sequence.

The 317 amino acid sequence of full length human SFRP5 is (Melkonyan et al., 1997, *Proc Natl Acad Sci U.S.A.*, 94:13636-41; NCBI Reference Sequence: NP_003006.2):

(SEQ ID NO: 1)
MRAAAAGGGCRTAALALLLGALHWAPARCEEYDYYGWQAEPLHGRS

YSKPPQCLDIPADLPLCHTVGYKRMRLPNLLEHESLAEVKQQASSW

LPLLAKRCHSDTQVFLCSLFAPVCLDRPIYPCRSLCEAVRAGCAPL

MEAYGFPWPEMLHCHKFPLDNDLCIAVQFGHLPATAPPVTKICAQC

EMEHSADGLMEQMCSSDFVVKMRIKEIKIENGDRKLIGAQKKKKLL

KPGPLKRKDTKRLVLHMKNGAGCPCPQLDSLAGSFLVMGRKVDGQL

LLMAVYRWDKKNKEMKFAVKFMFSYPCSLYYPFFYGAAEPH and is encoded by the DNA sequence (shown with optional stop codon):

(SEQ ID NO: 2)
atgcgcgcggcggcggcgggcggcggcgtgcgcaccgcggcgctgg cgctgctgctgggcgcgctgcattgggcgccggcgcgctgcgaaga atatgattattatggctggcaggcggaaccgctgcatggccgcagc tatagcaaaccgccgcagtgcctggatattccggcggatctgccgc tgtgccataccgtgggctataaacgcatgcgcctgccgaacctgct ggaacatgaaagcctggcggaagtgaaacaggcgagcagctgg ctgccgctgctggcgaaacgctgccatagcgatacccaggtgtttc tgtgcagcctgtttgcgccggtgtgcctggatcgcccgatttatcc gtgccgcagcctgtgcgaagcggtgcgcgcgggctgcgcgccgctg atggaagcgtatggctttccgtggccggaaatgctgcattgccata aatttccgctggataacgatctgtgcattgcggtgcagtttggcca tctgccggcgaccgcgccgccggtgaccaaaatttgcgcgcagtgc gaaatggaacatagcgcggatggcctgatggaacagatgtgcagca gcgatttgtggtgaaaatgcgcattaaagaaattaaaattgaaaa cggcgatcgcaaactgattggcgcgcagaaaaaaaaaaactgctg aaaccgggcccgctgaaacgcaaagataccaaacgcctggtgctgc atatgaaaaacggcgcgggctgccgtgcccgcagctggatagcct ggcgggcagctttctggtgatgggccgcaaagtggatggccagctg ctgctgatggcggtgtatcgctgggataaaaaaaacaaagaaatga aatttgcggtgaaatttatgtttagctatccgtgcagcctgtatta tccgttttttatggcgcggcggaaccgcattaa The amino acid sequence of human SFRP5 following cleavage of the predicted 29 amino acid residue signal sequence is:

(SEQ ID NO: 3)
EEYDYYGWQAEPLHGRSYSKPPQCLDIPADLPLCHTVGYKRMRLPN

LLEHESLAEVKQQASSWLPLLAKRCHSDTQVFLCSLFAPVCLDRPI

YPCRSLCEAVRAGCAPLMEAYGFPWPEMLHCHKFPLDNDLCIAVQF

GHLPATAPPVTKICAQCEMEHSADGLMEQMCSSDFVVKMRIKEIKI

ENGDRKLIGAQKKKKLLKPGPLKRKDTKRLVLHMKNGAGCPCPQLD

SLAGSFLVMGRKVDGQLLLMAVYRWDKKNKEMKFAVKFMFSYPCSL

YYPFFYGAAEPH and is encoded by the DNA sequence (shown with optional stop codon):

(SEQ ID NO: 4)
gaagaatatgattattatggctggcaggcggaaccgctgcatggcc gcagctatagcaaaccgccgcagtgcctggatattccggcggatct gccgctgtgccataccgtgggctataaacgcatgcgcctgccgaac ctgctggaacatgaaagcctggcggaagtgaaacagcaggcgagca gctggctgccgctgctggcgaaacgctgccatagcgatacccaggt gtttctgtgcagcctgtttgcgccggtgtgcctggatcgcccgatt tatccgtgccgcagcctgtgcgaagcggtgcgcgcgggctgcgcgc cgctgatggaagcgtatggctttccgtggccggaaatgctgcattg ccataaatttccgctggataacgatctgtgcattgcggtgcagttt ggccatctgccggcgaccgcgccgccggtgaccaaaatttgcgcgc agtgcgaaatggaacatagcgcggatggcctgatggaacagatgtg cagcagcgattttgtggtgaaaatgcgcattaaagaaattaaaatt cagcagcgattttgtggtgaaaatgcgcattaaagaaattaaaatt gaaaacggcgatcgcaaactgattggcgcgcagaaaaaaaaaaaac tgctgaaaccgggcccgctgaaacgcaaagataccaaacgcctggt gctgcatatgaaaaacggcgcgggctgcccgtgcccgcagctggat agcctggcgggcagctttctggtgatgggccgcaaagtggatggcc agctgctgctgatggcggtgtatcgctgggataaaaaaaacaaaga aatgaaatttgcggtgaaatttatgtttagctatccgtgcagcctg tattatccgtttttttatggcgcggcggaaccgcattaa The 314 amino acid sequence of full length murine SFRP5 is (NCBI Reference Sequence: NP_061250.2):

(SEQ ID NO: 5)
MWVAWSARTAALALLLGALHGAPTRGQEYDYYGWQAEPLHGRSYSK

PPQCLDIPADLPLCHTVGYKRMRLPNLLEHESLAEVKQQASSWLPL

LAKRCHSDTQVFLCSLFAPVCLDRPIYPCRSLCEAVRAGCAPLMEA

YGFPWPEMLHCHKFPLDNDLCIAVQFGHLPATAPPVTKICAQCEME

HSADGLMEQMCSSDFVVKMRIKEIKIDNGDRKLIGAQKKKKLLKAG

PLKRKDTKKLVLHMKNGASCPCPQLDNLTGSFLVMGRKVEGQLLLT

AVYRWDKKNKEMKFAVKFMFSYPCSLYYPFFYGAAEPH and is encoded by the DNA sequence (shown with optional stop codon):

(SEQ ID NO: 6)
atgtgggtggcgtggagcgcgcgcaccgcggcgctggcgctgctgc tgggcgcgctgcatggcgcgccgacccgcggccaggaatatgatta ttatggctggcaggcggaaccgctgcatggccgcagctatagcaaa ccgccgcagtgcctggatattccggcggatctgccgctgtgccata ccgtgggctataaacgcatgcgcctgccgaacctgctggaacatga aagcctggcggaagtgaaacagcaggcgagcagctggctgccgctg ctggcgaaacgctgccatagcgatacccaggtgtttctgtgcagcc tgtttgcgccggtgtgcctggatcgcccgatttatccgtgccgcag cctgtgcgaagcggtgcgcgcgggctgcgcgccgctgatggaagcg tatggctttccgtggccggaaatgctgcattgccataaatttccgc tggataacgatctgtgcattgcggtgcagtttggccatctgccggc gaccgcgccgccggtgaccaaaatttgcgcgcagtgcgaaatggaa catagcgcggatggcctgatggaacagatgtgcagcagcgattttg tggtgaaaatgcgcattaaagaaattaaaattgataacggcgatcg caaactgattggcgcgcagaaaaaaaaaaaactgctgaaagcgggc ccgctgaaacgcaaagataccaaaaaactggtgctgcatatgaaaa acggcgcgagctgcccgtgcccgcagctggataacctgaccggcag ctttctggtgatgggccgcaaagtggaaggccagctgctgctgacc gcggtgtatcgctgggataaaaaaaacaaagaaatgaaatttgcgg tgaaatttatgtttagctatccgtgcagcctgtattatccgttttt ttatggcgcggcggaaccgcattaa.

The amino acid sequence of murine SFRP5 following cleavage of the predicted 21 amino acid residue signal sequence is:

(SEQ ID NO: 7)
APTRGQEYDYYGWQAEPLHGRSYSKPPQCLDIPADLPLCHTVGYKR

MRLPNLLEHESLAEVKQQASSWLPLLAKRCHSDTQVFLCSLFAPVC

LDRPIYPCRSLCEAVRAGCAPLMEAYGFPWPEMLHCHKFPLDNDLC

IAVQFGHLPATAPPVTKICAQCEMEHSADGLMEQMCSSDFVVKMRI

KEIKIDNGDRKLIGAQKKKKLLKAGPLKRKDTKKLVLHMKNGASCP

CPQLDNLTGSFLVMGRKVEGQLLLTAVYRWDKKNKEMKFAVKFMFS

YPCSLYYPFFYGAAEPH and is encoded by the DNA sequence (shown with optional stop codon):

(SEQ ID NO: 8)
gcgccgacccgcggccaggaatatgattattatggctggcaggcgg aaccgctgcatggccgcagctatagcaaaccgccgcagtgcctgga tattccggcggatctgccgctgtgccataccgtgggctataaacgc atgcgcctgccgaacctgctggaacatgaaagcctggcggaagtga aacagcaggcgagcagctggctgccgctgctggcgaaacgctgcca tagcgatacccaggtgtttctgtgcagcctgtttgcgccggtgtgc ctggatcgcccgatttatccgtgccgcagcctgtgcgaagcggtgc gcgcgggctgcgcgccgctgatggaagcgtatggctttccgtggcc ggaaatgctgcattgccataaatttccgctggataacgatctgtgc attgcggtgcagtttggccatctgccggcgaccgcgccgccggtga ccaaaatttgcgcgcagtgcgaaatggaacatagcgcggatggcct gatggaacagatgtgcagcagcgattttgtggtgaaaatgcgcatt

```
aaagaaattaaaattgataacggcgatcgcaaactgattggcgcgc agaaaaaaaaaaaactgctgaaagcgggcccgctgaaacgcaaaga taccaaaaaactggtgctgcatatgaaaaacggcgcgagctgcccg tgcccgcagctggataacctgaccggcagctttctggtgatgggcc gcaaagtggaaggccagctgctgctgaccgcggtgtatcgctggga taaaaaaaacaaagaaatgaaatttgcggtgaaatttatgtttagc tatccgtgcagcctgtattatccgttttttttatggcgcggcggaac cgcattaa.
```

Nucleic acid sequences encoding a SFRP5 polypeptide provided herein, including those degenerate to SEQ ID NO: 2, 4, 6 or 8, and those encoding polypeptide variants of SEQ ID NO: 1, 3, 5 or 7 form other aspects of the instant disclosure.

II.B. SFRP5 Vectors

In order to express the SFRP5 nucleic acid sequences provided herein, the appropriate coding sequences, e.g., SEQ ID NO: 2 or 4, can be cloned into a suitable vector and after introduction in a suitable host, the sequence can be expressed to produce the encoded polypeptide according to standard cloning and expression techniques, which are known in the art (e.g., as described in Sambrook et al., (2001), supra). The invention also relates to such vectors comprising a nucleic acid sequence according to the invention.

A "vector" refers to a delivery vehicle that (a) promotes the expression of a polypeptide-encoding nucleic acid sequence; (b) promotes the production of the polypeptide therefrom; (c) promotes the transfection/transformation of target cells therewith; (d) promotes the replication of the nucleic acid sequence; (e) promotes stability of the nucleic acid; (f) promotes detection of the nucleic acid and/or transformed/transfected cells; and/or (g) otherwise imparts advantageous biological and/or physiochemical function to the polypeptide-encoding nucleic acid. A vector can be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors.

A recombinant expression vector can be designed for expression of a SFRP5 protein in prokaryotic (e.g., *E. coli*) or eukaryotic cells (e.g., insect cells, using baculovirus expression vectors, yeast cells, or mammalian cells). Representative host cells include those hosts typically used for cloning and expression, including *Escherichia coli* strains TOP10F', TOP10, DH10B, DH5a, HB101, W3110, BL21 (DE3) and BL21 (DE3)pLysS, BLUESCRIPT (Stratagene), mammalian cell lines CHO, CHO-K1, HEK293, 293-EBNA pIN vectors (Van Heeke & Schuster, *J. Biol. Chem.* 264: 5503-5509 (1989); pET vectors (Novagen, Madison Wis.). Alternatively, the recombinant expression vector can be transcribed and translated in vitro, for example using T7 promoter regulatory sequences and T7 polymerase and an in vitro translation system. Preferably, the vector contains a promoter upstream of the cloning site containing the nucleic acid sequence encoding the polypeptide. Examples of promoters, which can be switched on and off, include the lac promoter, the T7 promoter, the trc promoter, the tac promoter and the trp promoter.

Thus, provided herein are vectors comprising a nucleic acid sequence encoding SFRP5 that facilitate the expression of recombinant SFRP5. In various embodiments, the vectors comprise an operably linked nucleotide sequence which regulates the expression of SFRP5. A vector can comprise or be associated with any suitable promoter, enhancer, and other expression-facilitating elements. Examples of such elements include strong expression promoters (e.g., a human CMV IE promoter/enhancer, an RSV promoter, SV40 promoter, SL3-3 promoter, MMTV promoter, or HIV LTR promoter, EF1alpha promoter, CAG promoter), effective poly (A) termination sequences, an origin of replication for plasmid product in *E. coli*, an antibiotic resistance gene as a selectable marker, and/or a convenient cloning site (e.g., a polylinker). Vectors also can comprise an inducible promoter as opposed to a constitutive promoter such as CMV IE. In one aspect, a nucleic acid comprising a sequence encoding a SFRP5 polypeptide which is operatively linked to a tissue specific promoter which promotes expression of the sequence in a metabolically-relevant tissue, such as liver or pancreatic tissue is provided.

II.C. Host Cells

In another aspect of the instant disclosure, host cells comprising the SFRP5 nucleic acids and vectors disclosed herein are provided. In various embodiments, the vector or nucleic acid is integrated into the host cell genome, which in other embodiments the vector or nucleic acid is extra-chromosomal.

Recombinant cells, such as yeast, bacterial (e.g., *E. coli*), and mammalian cells (e.g., immortalized mammalian cells) comprising such a nucleic acid, vector, or combinations of either or both thereof are provided. In various embodiments cells comprising a non-integrated nucleic acid, such as a plasmid, cosmid, phagemid, or linear expression element, which comprises a sequence coding for expression of a SFRP5 polypeptide, are provided.

A vector comprising a nucleic acid sequence encoding a SFRP5 polypeptide provided herein can be introduced into a host cell by transformation or by transfection. Methods of transforming a cell with an expression vector are well known.

A SFRP5-encoding nucleic acid can be positioned in and/or delivered to a host cell or host animal via a viral vector. Any suitable viral vector can be used in this capacity. A viral vector can comprise any number of viral polynucleotides, alone or in combination with one or more viral proteins, which facilitate delivery, replication, and/or expression of the nucleic acid of the invention in a desired host cell. The viral vector can be a polynucleotide comprising all or part of a viral genome, a viral protein/nucleic acid conjugate, a virus-like particle (VLP), or an intact virus particle comprising viral nucleic acids and a SFRP5 polypeptide-encoding nucleic acid. A viral particle viral vector can comprise a wild-type viral particle or a modified viral particle. The viral vector can be a vector which requires the presence of another vector or wild-type virus for replication and/or expression (e.g., a viral vector can be a helper-dependent virus), such as an adenoviral vector amplicon. Typically, such viral vectors consist of a wild-type viral particle, or a viral particle modified in its protein and/or nucleic acid content to increase transgene capacity or aid in transfection and/or expression of the nucleic acid (examples of such vectors include the herpes virus/AAV amplicons). Typically, a viral vector is similar to and/or derived from a virus that normally infects humans. Suitable viral vector particles in this respect, include, for example, adenoviral vector particles (including any virus of or derived from a virus of the adenoviridae), adeno-associated viral vector particles (AAV vector particles) or other parvoviruses and parvoviral vector particles, papillomaviral vector particles, flaviviral vectors, alphaviral vectors, herpes viral vectors, pox virus vectors, retroviral vectors, including lentiviral vectors.

II.D. Isolation of a SFRP5 Polypeptide

A SFRP5 polypeptide expressed as described herein can be isolated using standard protein purification methods. A SFRP5 polypeptide can be isolated from a cell in which is it naturally expressed or it can be isolated from a cell that has been engineered to express SFRP5, for example a cell that does not naturally express SFRP5.

Protein purification methods that can be employed to isolate a SFRP5 polypeptide, as well as associated materials and reagents, are known in the art. Additional purification methods that may be useful for isolating a SFRP5 polypeptide can be found in references such as Bootcov M R, 1997, *Proc. Natl. Acad. Sci. USA* 94:11514-9, Fairlie W D, 2000, *Gene* 254: 67-76.

II.E. SFRP5 Antigen-Binding Proteins

The antigen binding proteins provided are polypeptides into which one or more complementary determining regions (CDRs), as described herein, are embedded and/or joined. In some antigen binding proteins, the CDRs are embedded into a "framework" region, which orients the CDR(s) such that the proper antigen binding properties of the CDR(s) are achieved. Certain antigen binding proteins described herein are antibodies or are derived from antibodies. In other antigen binding proteins, the CDR sequences are embedded in a different type of protein scaffold. The various structures are further described below.

The antigen binding proteins that are disclosed herein have a variety of utilities. The antigen binding proteins, for instance, are useful in specific binding assays, affinity purification of SFRP5, and in screening assays to identify other antagonists of SFRP5 activity. Other uses for the antigen binding proteins include, for example, diagnosis of SFRP5-associated diseases or conditions and screening assays to determine the presence or absence of SFRP5. Given that the antigen binding proteins that are provided are antagonists, the SFRP5 antigen binding proteins have value in therapeutic methods in which it is useful to reduce weight gain, even while maintaining or increasing food intake, increasing % fat mass and increasing % lean mass, improving glucose tolerance, decreasing insulin levels, decreasing cholesterol and triglyceride levels. Accordingly, the antigen binding proteins have utility in the treatment and prevention of diabetes, e.g., type 2 diabetes, obesity, dyslipidemia, elevated glucose levels or elevated insulin levels.

A variety of selective binding agents useful for modulating the activity of SFRP5 are provided. These agents include, for instance, antigen binding proteins that contain an antigen binding domain (e.g., single chain antibodies, domain antibodies, and polypeptides with an antigen binding region) and specifically bind to a SFRP5 polypeptide, in particular human SFRP5. Some of the agents, for example, are useful in enhancing the activity of SFRP5, and can activate one or more activities associated with SFRP5.

In general the antigen binding proteins that are provided typically comprise one or more CDRs as described herein (e.g., 1, 2, 3, 4, 5 or 6). In some instances, the antigen binding protein comprises (a) a polypeptide structure and (b) one or more CDRs that are inserted into and/or joined to the polypeptide structure. The polypeptide structure can take a variety of different forms. For example, it can be, or comprise, the framework of a naturally occurring antibody, or fragment or variant thereof, or may be completely synthetic in nature. Examples of various polypeptide structures are further described below.

In some embodiments in which the antigen binding protein comprises (a) a polypeptide framework structure and (b) one or more CDRs that are inserted into and/or joined to the polypeptide framework structure, the polypeptide framework structure of an antigen binding protein is an antibody or is derived from an antibody, including, but not limited to, monoclonal antibodies, bispecific antibodies, minibodies, domain antibodies such as Nanobodies®, synthetic antibodies (sometimes referred to herein as "antibody mimetics"), chimeric antibodies, humanized antibodies, antibody fusions (sometimes referred to as "antibody conjugates"), and portions or fragments of each, respectively. In some instances, the antigen binding protein is an immunological fragment of an antibody (e.g., a Fab, a Fab', a F(ab')$_2$, or a scFv).

In one embodiment, an antigen binding protein specifically binds to human SFRP5. In a specific embodiment, the antigen binding protein specifically binds to human SFRP5 comprising or consisting of the amino acid sequence of SEQ ID NO:1. In another specific embodiment, the antigen binding protein specifically binds to human SFRP5 comprising or consisting of the amino acid sequence of SEQ ID NO:3. In another embodiment, the antigen binding protein specifically binds to murine SFRP5. In a specific embodiment, the antigen binding protein specifically binds to murine SFRP5 comprising or consisting of SEQ ID NO: 5. In another a specific embodiment, the antigen binding protein specifically binds to murine SFRP5 comprising or consisting of SEQ ID NO:7. In yet another embodiment, the antigen binding protein specifically binds to both a human SFRP5 and a murine SFRP5.

The antigen binding proteins that are provided are antagonists and typically have one, two, three, four, five, six, seven or all eight of the following characteristics:

(a) ability to reduce circulating levels of SFRP5, where the levels can be measured, for example, by the methods described herein (e.g., Western Blot analysis). The decrease can be at least 10, 25, 50, 100% or more relative to the pre-treatment levels of SEQ ID NO: 1 or 3 under comparable conditions.

(b) ability to increase glucose tolerance;
(c) ability to increase insulin sensitivity;
(d) ability to decrease fat mass;
(e) ability to decrease fasting insulin levels;
(f) ability to decrease cholesterol levels;
(g) ability to decrease triglyceride levels;
(h) decrease AST, ALT, and/or ALP levels.

In one embodiment, a SFRP5 antigen binding protein has one or more of the following activities:

(a) binds human SFRP5 such that $K_D$, is ≤200 nM, is ≤150 nM, is ≤100 nM, is ≤50 nM, is ≤10 nM, is ≤5 nM, is ≤2 nM, or is ≤1 nM, e.g., as measured via a surface plasma resonance technique.

(b) has a half-life in human serum of at least 3 days;

Some antigen binding proteins that are provided have an on-rate ($k_a$) for SFRP5 of at least $10^4$/M×seconds, at least $10^5$/M×seconds, or at least $10^6$/M×seconds as measured, for instance, as described below. Certain antigen binding proteins that are provided have a slow dissociation rate or off-rate. Some antigen binding proteins, for instance, have a $k_d$ (off-rate) of $1 \times 10^{-2}$ s$^{-1}$, or $1 \times 10^{-3}$ s$^{-1}$, or $1 \times 10^{-4}$ s$^{-1}$, or $1 \times 10^{-5}$ s$^{-1}$. In certain embodiments, the antigen binding protein has a $K_1$ (equilibrium binding affinity) of less than 25 pM, 50 pM, 100 pM, 500 pM, 1 nM, 5 nM, 10 nM, 25 nM or 50 nM.

In another aspect, an antigen-binding protein is provided having a half-life of at least one day in vitro or in vivo (e.g., when administered to a human subject). In one embodiment, the antigen binding protein has a half-life of at least three days. In various other embodiments, the antigen binding protein has a half-life of 4, 5, 6, 7, 8, 9, 10, 15, 20, 25, 30, 40, 50, or 60 days or longer. In another embodiment, the antigen binding protein is derivatized or modified such that it has a longer half-life as compared to the underivatized or unmodified antibody. In another embodiment, the antigen binding protein contains point mutations to increase serum half life. Further details regarding such mutant and derivatized forms are provided below.

SFRP5 Antigen-Binding Proteins with Naturally Occurring Antibody Structure

Some of the antigen binding proteins that are provided have the structure typically associated with naturally occurring antibodies. The structural units of these antibodies typically comprise one or more tetramers, each composed of two identical couplets of polypeptide chains, though some species of mammals also produce antibodies having only a single heavy chain. In a typical antibody, each pair or couplet includes one full-length "light" chain (in certain embodiments, about 25 kDa) and one full-length "heavy" chain (in certain embodiments, about 50-70 kDa). Each individual immunoglobulin chain is composed of several "immunoglobulin domains", each consisting of roughly 90 to 110 amino acids and expressing a characteristic folding pattern. These domains are the basic units of which antibody polypeptides are composed. The amino-terminal portion of each chain typically includes a variable domain that is responsible for antigen recognition. The carboxy-terminal portion is more conserved evolutionarily than the other end of the chain and is referred to as the "constant region" or "C region". Human light chains generally are classified as kappa and lambda light chains, and each of these contains one variable domain and one constant domain. Heavy chains are typically classified as mu, delta, gamma, alpha, or epsilon chains, and these define the antibody's isotype as IgM, IgD, IgG, IgA, and IgE, respectively. IgG has several subtypes, including, but not limited to, IgG1, IgG2, IgG3, and IgG4. IgM subtypes include IgM, and IgM2. IgA subtypes include IgA1 and IgA2. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that may be responsible for effector function. The number of heavy chain constant region domains will depend on the isotype. IgG heavy chains, for example, each contain three C region domains known as $C_H1$, $C_H2$ and $C_H3$. The antibodies that are provided can have any of these isotypes and subtypes. In certain embodiments, the SFRP5 antibody is of the IgG1, IgG2, or IgG4 subtype.

In full-length light and heavy chains, the variable and constant regions are joined by a "J" region of about twelve or more amino acids, with the heavy chain also including a "D" region of about ten more amino acids. See, e.g. Fundamental Immunology, 2nd ed., Ch. 7 (Paul, W., ed.) 1989, New York: Raven Press (hereby incorporated by reference in its entirety for all purposes). The variable regions of each light/heavy chain pair typically form the antigen binding site.

One example of an IgG2 heavy constant domain of an exemplary SFRP5 monoclonal antibody has the amino acid sequence:

```
ASTKGPSVFPLAPCSRSTSESTAALGCLVKDYFPEPVTVSWNSGAL

TSGVHTFPAVLQSSGLYSLSSVVTVPSSNGFTQTYTCNVDHKPSNT

KVDKTVERKCCVECPPCPAPPVAGPSVFLFPPKPKDTLMISRTPEV

TCVVVDVSHEDPEVQFNWYVDGVEVHNAKTKPREEQFNSTFRVVSV

LTVVHQDWLNGKEYKCKVSNKGLPAPIEKTISKTKGQPREPQVYTL

PPSREEMTKNQVSLTCLVKGFYPSDIAVEWESNGQPENNYKTTPPM

LDSDGSFFLYSKLTVDKSRWQQGNVFSCSVMHEALHNHYTQKSLSL

SPGK*

(SEQ. ID NO: 9; asterisk corresponds to stop codon).
```

One example of a lambda light chain constant domain of an exemplary SFRP5 monoclonal antibody has the amino acid sequence:

```
QPKAAPSVTLFPPSSEELQANKATLVCLISDFYPGAVTVAWKADSS

PVKAGVETTTPSKQSNNKYAASSYLSLTPQEWKSHRSYSCQVTHEG

STVEKTVAPTECS*

(SEQ ID NO: 10; asterisk corresponds to stop codon)
```

An example of a kappa light chain constant domain of an exemplary SFRP5 monoclonal antibody has the amino acid sequence:

```
TVAAPSVFIFPPSDEQLKSGTASVVCLLNNFYPREAKVQWKVDNAL

QSGNSQESVTEQDSKDSTYSLSSTLTLSKADYEKHKVYACEVTHQG

LSSPVTKSFNRGEC*

(SEQ ID NO: 11; asterisk corresponds to stop codon)
```

For the antibodies provided herein, the variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair mentioned above typically are aligned by the framework regions to form a structure that binds specifically with a specific epitope on SFRP5. From N-terminal to C-terminal, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, Md.), or Chothia & Lesk, 1987, J. Mol. Biol. 196:901-917; Chothia et al., 1989, Nature 342:878-883.

The various heavy chain and light chain variable regions of a human antibody framework (IgG2/kappa) into which CDRs from the specific murine monoclonal antibodies described in the Examples (see Example 5; Tables 9 and 10) have been embedded, including appropriate back-mutations, are set forth in Table 2. Each of these variable regions may be attached to be above heavy and light chain constant regions to form a complete antibody heavy and light chain, respectively (see Table 1). Further, each of the so generated heavy and light chain sequences may be combined to form a complete antibody structure. It should be understood that the heavy chain and light chain variable regions provided herein can also be attached to other constant domains having different sequences that the exemplary sequences listed above.

Specific examples of full length heavy and light chain sequences of a human antibody framework (IgG2/kappa) into which into which CDRs from the specific murine monoclonal antibodies described in the Examples (see Example 5; Tables 9 and 10), have been embedded, including appropriate back-mutations, are set forth in Table 1 (CDR sequences underlined).

other instances, the antibodies contain two identical light chains and two identical heavy chains. As an example, an antibody or immunologically functional fragment may include two H1 heavy chains and two L1 light chains, or two H2 heavy chains and two L2 light chains and other similar combinations of pairs of light chains and pairs of heavy chains as listed in Table 1.

Other antigen binding proteins that are provided are variants of antibodies formed by combination of the heavy and light chains shown in Table 1 and comprise light and/or heavy chains that each have at least 70%, 75%, 80%, 85%, 90%, 95%, 97% or 99% identity to the amino acid sequences of these chains. In some instances, such antibodies include at least one heavy chain and one light chain, whereas in other instances the variant forms contain two identical light chains and two identical heavy chains Variable Domains of Exemplary SFRP5 Antigen Binding Proteins Also provided are antigen binding proteins that contain a heavy chain variable region selected from the group con-

TABLE 1

Exemplary Heavy and Light Chains

| Designation | SEQ ID NO: | Amino Acid Sequence |
| --- | --- | --- |
| H1 | 15 | QVQLVQSGAEVKKPGASVKVSCKASGYTFT<u>DYYIN</u>WVRQAT GQGLEWMG<u>RIYPGSGNTYYNEKFKG</u>RVTMTRDTSISTAYME LSSLRSEDTAVYYCAR<u>YSASAMDY</u>WGQGTLVTVSSASTKGP SVFPLAPCSRSTSESTAALGCLVKDYFPEPVTVSWNSGALT SGVHTFPAVLQSSGLYSLSSVVTVPSSNGFTQTYTCNVDHK PSNTKVDKTVERKCCVECPPCPAPPVAGPSVFLFPPKPKDT LMISRTPEVTCVVVDVSHEDPEVQRNWYVDGVEVHNAKTKP REEQFNSTFRVVSVLTVVHQDWLNGKEYKCKVSNKGLPAPI EKTISKTKGQPREPQVYTLPPSREEMTKNQVSLTCLVKGFY PSDIAVEWESNGQPENNYKTTPPMLDSDGSFFLYSKLTVDK SRWQQGNVFSCSVMHEALHNHYTQKSLSLSPGK |
| H2 | 16 | QVQLVQSGAEVKKPGASVKVSCKASGYTFT<u>DYYIN</u>WVRQAT GQGLEWMG<u>RIYPGSGNTYYNEKFKG</u>RVTLTAEKSSSTAYME LSSLRSEDTAVYFCAA<u>YSASAMDY</u>WGQGTLVTVSSASTKGP SVFPLAPCSRSTSESTAALGCLVKDYFPEPVTVSWNSGALT SGVHTFPAVLQSSGLYSLSSVVTVPSSNFGTQTYTCNVDHK PSNTKVDKTVERKCCVECPPCPAPPVAGPSVFLFPPKPKDT LMISRTPEVTCVVVDVSHEDPEVQFNWYVDGVEVHNAKTKP REEQFNSTFRVVSVLTVVHQDWLNGKEYKCKVSNKGLPAPI EKTISKTKGQPREPQVYTLPPSREEMTKNQVSLTCLVKGFY PSDIAVEWESNGQPENNYKTTPPMLDSDGSFFLYSKLTVDK SRWQQGNVFSCSVMHEALHNHYTQKSLSLSPGK |
| L1 | 17 | DIVMTQSPDSLAVSLGERATINC<u>RASESVDSYGKSFMY</u>WYQ QKPGQPPKLLIY<u>LANNLES</u>GVPDRFSGSGSGTDFTLTISSL QAEDVAVYYC<u>QQNNEDPWT</u>FGGGTKVEIKRTVAAPSVFIFP PSDEQLKSGTASVVCLLNNFYPREAKVQWKVDNALQSGNSQ ESVTEQDSKDSTYSLSSTLTLSKADYEKHKVYACEVTHQGL SSPVTKSFNRGEC |
| L2 | 18 | DVVLTQSPDSLAVSLGERATINC<u>RASESVDSYGKSFMY</u>WYQ QKPGQPPKLLIY<u>LANNLES</u>GVPDRFSGSGSRTFTLTISSL QAEDVAVYYC<u>QQNNEDPWT</u>FGGGTKVEIKRTVAAPSVFIFP PSDEQLKSGTASVVCLLNNFYPREAKVQWKVDNALQSGNSQ ESVTEQDSKDSTYSLSSTLTLSKADYEKHKVYACEVTHQGL SSPVTKSFNRGEC |

Each of the exemplary heavy chains (H1 and H2) listed in Table 1 can be combined with any of the exemplary light chains listed in Table 1 (L1 and L2) to form an antibody. Examples of such combinations include H1 combined with L1 or L2; and H2 combined with L1 or L2. In some instances, the antibodies include at least one heavy chain and one light chain from those listed in Table 1. In other embodiments, the antibodies comprise two different heavy chains and two different light chains listed in Table 1. In still sisting of $V_H1$ and $V_H2$ and/or a light chain variable region selected from the group consisting of $V_L1$ and $V_L2$, as shown in Table 2 below, and immunologically functional fragments, derivatives, muteins and variants of these light chain and heavy chain variable regions.

Antigen binding proteins of this type can generally be designated by the formula "$V_Hx/V_Ly$," where "x" corresponds to the number of heavy chain variable regions and "y" corresponds to the number of the light chain variable regions (in general, x and y are each 1 or 2) as listed in Table 2. However, the SFRP5 antigen binding proteins can also include a single light chain variable domain or a single heavy chain variable domain, provided the individual domain can bind a SFRP5 polypeptide (e.g., SEQ ID NO: 1 or 3).

As discussed above, the sequences set forth in Table 2 reflect the various heavy chain and light chain variable regions of a human antibody framework (IgG2/kappa) into which CDRs from the specific murine monoclonal antibodies described in the Examples (see Example 5; Tables 9 and 10) have been embedded, including appropriate back-mutations (CDR sequences underlined).

TABLE 2

Exemplary $V_H$ and $V_L$ Chains

| Designation | SEQ ID NO: | Amino Acid Sequence |
|---|---|---|
| $V_H1$ | 19 | QVQLVQSGAEVKKPGASVKVSCKASGYTFT<u>DYYIN</u>WVRQAT GQGLEWMG<u>RIYPGSGNTYYNEKFKG</u>RVTMTRDTSISTAYME LSSLRSEDTAVYYCAR<u>YSASAMDY</u>WGQGTLVTVSS |
| $V_H2$ | 20 | QVQLVQSGAEVKKPGASVKVSCKASGYTFT<u>DYYIN</u>WVRQAT GQGLEWMG<u>RIYPGSGNTYYNEKFKG</u>RVTLTAEKSSSTAYME LSSLRSEDTAVYFCAA<u>YSASAMDY</u>WGQGTLVTVSS |
| $V_L1$ | 21 | DIVMTQSPDSLAVSLGERATINC<u>RASESVDSYGKSFMY</u>WYQ QKPGQPPKLLIY<u>LANNLES</u>GVPDRFSGSGSGTDFTLTISSL QAEVAVYYC<u>QQNNEDPWT</u>FGGGTKVEIKR |
| $V_L2$ | 22 | DVVLTQSPDSLAVSLGERATINC<u>RASESVDSYGKSFMY</u>WYQ QKPGQPPKLLIY<u>LANNLES</u>GVPDRFSGSGSRTDFTLTISSL QAEDVAVYYC<u>QQNNEDPWT</u>FGGGTKVEIKR |

Each of the heavy chain variable regions listed in Table 2 may be combined with any of the light chain variable regions shown in Table 2 to form an antigen binding protein. Examples of such combinations include $V_H1$ combined with $V_L1$ or $V_L2$; and $V_H2$ combined with $V_L1$ or $V_L2$.

In some embodiments, the antigen binding protein includes at least one heavy chain variable region and/or one light chain variable region from those listed in Table 2. In some instances, the antigen binding protein includes at least two different heavy chain variable regions and/or light chain variable regions from those listed in Table 2. An example of such an antigen binding protein comprises one $V_H1$, and one $V_L2$. Similarly, an example of such an antigen binding protein comprises one $V_L1$, and one $V_L2$.

The various combinations of heavy chain variable regions may be combined with any of the various combinations of light chain variable regions.

In certain embodiments, the antigen binding protein contains two identical light chain variable regions and/or two identical heavy chain variable regions. As an example, the antigen binding protein may be an antibody or immunologically functional fragment that includes two light chain variable regions and two heavy chain variable regions in combinations of pairs of light chain variable regions and pairs of heavy chain variable regions as listed in Table 2.

Some antigen binding proteins that are provided comprise a heavy chain variable domain comprising a sequence of amino acids that differs from the sequence of a heavy chain variable domain selected from $V_H1$ or $V_H2$ at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing variable domain sequences. The heavy chain variable region in some antigen binding proteins comprises a sequence of amino acids that has at least 70%, 75%, 80%, 85%, 90%, 95%, 97% or 99% sequence identity to the amino acid sequences of the heavy chain variable region of $V_H1$ or $V_H2$.

Certain antigen binding proteins comprise a light chain variable domain comprising a sequence of amino acids that differs from the sequence of a light chain variable domain selected from $V_L1$ or $V_L2$ at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing variable domain sequences. The light chain variable region in some antigen binding proteins comprises a sequence of amino acids that has at least 70%, 75%, 80%, 85%, 90%, 95%, 97% or 99% sequence identity to the amino acid sequences of the light chain variable region of $V_L1$ or $V_L2$.

CDRs of Exemplary SFRP5 Antigen Binding Proteins

The antigen binding proteins disclosed herein are polypeptides into which one or more CDRs are grafted, inserted and/or joined. An antigen binding protein can have 1, 2, 3, 4, 5 or 6 CDRs. An antigen binding protein thus can have, for example, one heavy chain CDR1 ("CDRH1"), and/or one heavy chain CDR2 ("CDRH2"), and/or one heavy chain CDR3 ("CDRH3"), and/or one light chain CDR1 ("CDRL1"), and/or one light chain CDR2 ("CDRL2"), and/or one light chain CDR3 ("CDRL3"). Some antigen binding proteins include both a CDRH3 and a CDRL3. Specific heavy and light chain CDRs are identified in Tables 3A and 3B, respectively.

Complementarity determining regions (CDRs) and framework regions (FR) of a given antibody may be identified using the system described by Kabat et al. in Sequences of Proteins of Immunological Interest, 5th Ed., US Dept. of Health and Human Services, PHS, NIH, NIH Publication no. 91-3242, 1991. Certain antibodies that are disclosed herein comprise one or more amino acid sequences that are identical or have substantial sequence identity to the amino acid sequences of one or more of the CDRs presented in Table 3A (CDRHs) and Table 3B (CDRLs).

TABLE 3A

Exemplary CDRH Sequences

| Designation | SEQ ID NO: | Amino Acid Sequence |
|---|---|---|
| CDRH1 | 23 | DYYIN |
| CDRH2 | 24 | RIYPGSGNTYYNEKFKG |
| CDRH3 | 25 | YSASAMDY |

TABLE 3B

Exemplary CDRL Sequences

| Designation | SEQ ID NO: | Amino Acid Sequence |
|---|---|---|
| CDRL1 | 26 | RASESVDSYGKSFMY |
| CDRL2 | 27 | LANNLES |
| CDRL3 | 28 | QQNNEDPWT |

In another aspect, an antigen binding protein includes 1, 2, 3, 4, 5, or 6 variant forms of the CDRs listed in Tables 3A and 3B, each having at least 80%, 85%, 90%, 95%, 96%, 97%, 98%, or 99% sequence identity to a CDR sequence listed in Tables 3A and 3B. Some antigen binding proteins include 1, 2, 3, 4, 5, or 6 of the CDRs listed in Tables 3A and 3B, each or collectively differing by no more than 1, 2, 3, 4 or 5 amino acids from the CDRs listed in these tables.

Exemplary Antigen Binding Proteins

The sequence information for "humanized" antibodies (identified by the prefix "hz") and appropriate back mutations (identified by the prefix "hzbm") corresponding to specific murine monoclonal antibodies described in the Examples below is summarized in Table 4. Thus, in an embodiment, an antigen binding protein is an antibody with the CDR, variable domain and/or light and heavy chain sequences as specified in one of the rows of Table 4.

TABLE 4

Exemplary Humanized Antigen Binding Proteins

| Ref. No. | Full Heavy SEQ ID NO: | Full Light SEQ ID NO: | Variable Heavy SEQ ID NO: | Variable Light SEQ ID NO: | CDRH1 SEQ ID NO: | CDRH2 SEQ ID NO: | CDRH3 SEQ ID NO: | CDRL1 SEQ ID NO: | CDRL2 SEQ ID NO: | CDRL3 SEQ ID NO: |
|---|---|---|---|---|---|---|---|---|---|---|
| hz24C18.3.001 | 15 | 17 | 19 | 21 | 23 | 24 | 25 | 26 | 27 | 28 |
| hz24C18.3.002 | 16 | 18 | 20 | 22 | 23 | 24 | 25 | 26 | 27 | 28 |

The structure and properties of CDRs within a naturally occurring antibody has been described, supra. Briefly, in a traditional antibody, the CDRs are embedded within a framework in the heavy and light chain variable region where they constitute the regions responsible for antigen binding and recognition. A variable region comprises at least three heavy or light chain CDRs, see, supra (Kabat et al., 1991, *Sequences of Proteins of Immunological Interest*, Public Health Service N.I.H., Bethesda, Md.; see also Chothia and Lesk, 1987, *J. Mol. Biol.* 196:901-917; Chothia et al., 1989, *Nature* 342: 877-883), within a framework region (designated framework regions 1-4, FR1, FR2, FR3, and FR4, by Kabat et al., 1991, supra; see also Chothia and Lesk, 1987, supra). The CDRs provided herein, however, may not only be used to define the antigen binding domain of a traditional antibody structure, but may be embedded in a variety of other polypeptide structures, as described herein.

In one aspect, the CDRs provided are (A) a CDRH selected from the group consisting of (i) a CDRH1 of SEQ ID NO:23; (ii) a CDRH2 of SEQ ID NO:24; (iii) a CDRH3 of SEQ ID NO:25; and (iv) a CDRH of (i), (ii) and (iii) that contains one or more amino acid substitutions, deletions or insertions of no more than five, four, three, two, or one amino acids; (B) a CDRL selected from the group consisting of (i) a CDRL1 of SEQ ID NO:25, (ii) a CDRL2 of SEQ ID NO:26; (iii) a CDRL3 of SEQ ID NO:27; and (iv) a CDRL of (i), (ii) and (iii) that contains one or more amino acid substitutions, deletions or insertions of no more than five, four, three, two, or one amino acids amino acids.

In various other embodiments, the antigen binding protein is derived from such antibodies. For instance, in one aspect, the antigen binding protein comprises 1, 2, 3, 4, 5 or all 6 of the CDRs listed in one of the rows for any particular antibody listed in Table 4. In another aspect, an antigen binding protein includes 1, 2, 3, 4, 5, or 6 variant forms of the CDRs listed in one of the rows for an antibody in Table 4, each CDR having at least 80%, 85%, 90%, 95%, 96%, 97%, 98%, or 99% sequence identity to a CDR sequence listed in Table 4. Some antigen binding proteins include 1, 2, 3, 4, 5, or 6 of the CDRs listed in one of the rows of Table 4, each differing by no more than 1, 2, 3, 4 or 5 amino acids from the CDRs listed in these tables. In another aspect, the antigen binding protein comprises all 6 of the CDRS listed in a row of Table 4 and the total number of amino acid changes to the CDRs collectively is no more than 1, 2, 3, 4, or 5 amino acids.

Some antigen binding proteins comprise a variable light domain and a variable heavy domain as listed in one of the rows for one of the antibodies listed in Table 4. In some instances, the antigen binding protein comprises two identical variable light domains and two identical variable heavy domains from one of the antibodies listed in Table 4. Some antigen binding proteins that are provided comprise a variable light domain and a variable heavy domain as listed in one of the rows for one of the antibodies listed in Table 4, except that one or both of the domains differs from the sequence specified in the table at only 1, 2, 3, 4, 5, 6, 7, 8, 9, 10, 11, 12, 13, 14 or 15 amino acid residues, wherein each such sequence difference is independently either a single amino acid deletion, insertion or substitution, with the deletions, insertions and/or substitutions resulting in no more than 1, 2, 3, 4, 5, 6, 7, 8, 9, 10, 11, 12, 13, 14 or 15 amino acid changes relative to the variable domain sequences specified in Table 4. Other antigen binding proteins also comprise a variable light domain and a variable heavy domain as listed in one of the rows for one of the antibodies listed in Table 4, except that one or both of the domains differs from the sequence specified in the table in that the heavy chain variable domain and/or light chain variable domain comprises or consists of a sequence of amino acids that has at least 70%, 75%, 80%, 85%, 90%, 95%, 96%, 97%, 98%, or 99% sequence identity to the amino acid sequences of the heavy chain variable domain or light chain variable domain sequences as specified in Table 4.

In another aspect, the antigen binding protein consists just of a variable light or variable heavy domain from an antibody listed in Table 4. In still another aspect, the antigen binding protein comprises two or more of the same variable heavy domains or two or more of the same variable light domains from those listed in Table 4. Such domain antibodies can be fused together or joined via a linker as described in greater detail below. The domain antibodies can also be fused or linked to one or more molecules to extend the half-life (e.g., PEG or albumin).

In another aspect, the antigen binding protein comprises a full length light chain and a full length heavy chain as listed in one of the rows for one of the antibodies listed in Table 4. Some antigen binding proteins that are provided comprise a full length light chain and a full length heavy chain as listed in one of the rows for one of the antibodies listed in Table 4, except that one or both of the chains differs from the sequence specified in the table at only 1, 2, 3, 4, 5, 6, 7, 8, 9, 10, 11, 12, 13, 14 or 15 amino acid residues, wherein each such sequence difference is independently either a single amino acid deletion, insertion or substitution, with the deletions, insertions and/or substitutions resulting in no more than 1, 2, 3, 4, 5, 6, 7, 8, 9, 10, 11, 12, 13, 14 or 15 amino acid changes relative to the full length sequences specified in Table 4. Other antigen binding proteins also comprise a full length light chain and a full length heavy chain as listed in one of the rows for one of the antibodies listed in Table 4, except that one or both of the chains differs from the sequence specified in the table in that the light chain and/or heavy chain comprises or consists of a sequence of amino acids that has at least 70%, 75%, 80%, 85%, 90%, 95%, 96%, 97%, 98%, or 99% sequence identity to the amino acid sequences of the light chain or heavy chain sequences as specified in Table 4.

In another embodiment, the antigen binding protein consists of a just a light or a heavy chain polypeptide as set forth in Table 4.

In still another aspect, antigen-binding proteins containing the CDRs, variable domains and/or full length sequences listed in Table 4 is a monoclonal antibody, a chimeric antibody, a humanized antibody, a human antibody, a multispecific antibody, or an antibody fragment of the foregoing. In another embodiment, the antibody fragment of the isolated antigen-binding proteins provided herein is a Fab fragment, a Fab' fragment, an F(ab')$_2$ fragment, an Fv fragment, a diabody, or a single chain antibody molecule based upon an antibody with the sequences as listed in Table 4.

In a further embodiment, the isolated antigen binding protein provided herein is a human antibody with the sequences as set forth in Table 4 and is of the IgG1-, IgG2- IgG3- or IgG4-type.

In yet another aspect, the isolated antigen-binding protein provided in Table 4 can be coupled to a labeling group and can compete for binding to SFRP5 with an antigen binding protein of one of the isolated antigen-binding proteins provided herein.

Competing Antigen Binding Proteins

In another embodiment, antigen binding proteins are provided that compete with one of the exemplified antibodies or functional fragments for described above for specific binding to a human SFRP5 (e.g., SEQ ID NO:1 or 3). Such antigen binding proteins may bind to the same epitope as one of the antigen binding proteins described herein, or to an overlapping epitope. Antigen binding proteins and fragments that compete with the exemplified antigen binding proteins are expected to show similar functional properties. The exemplified antigen binding proteins and fragments include those described above, including those with the heavy and light chains, variable region domains and CDRs included in Tables 1, 2, 3, and 4. Thus, as a specific example, the antigen binding proteins that are provided include those that compete with an antibody having:

(a) all 6 of the CDRs listed for any antibody listed in Table 4;

(b) a $V_H$ and a $V_L$ listed for any antibody listed in Table 4; or (c) two light chains and two heavy chains as specified for any antibody listed in Table 4.

Monoclonal Antibodies

The antigen binding proteins that are provided include monoclonal antibodies that bind to SFRP5. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e.g., a transgenic animal having human immunoglobulin sequences) with a SFRP5 immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds a SFRP5 polypeptide. Such hybridoma cell lines, and anti-SFRP5 monoclonal antibodies produced by them, are aspects of the present application.

Monoclonal antibodies secreted by a hybridoma cell line can be purified using any technique known in the art. Hybridomas or mAbs may be further screened to identify mAbs with particular properties, such as the ability to increase SFRP5 activity.

Chimeric and Humanized Antibodies

Chimeric and humanized antibodies based upon the foregoing sequences are also provided. Monoclonal antibodies for use as therapeutic agents may be modified in various ways prior to use. One example is a chimeric antibody, which is an antibody composed of protein segments from different antibodies that are covalently joined to produce functional immunoglobulin light or heavy chains or immunologically functional portions thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567; and Morrison et al., 1985, *Proc. Natl. Acad. Sci. USA* 81:6851-6855, which are hereby incorporated by reference. CDR grafting is described, for example, in U.S. Pat. No. 6,180,370, U.S. Pat. No. 5,693,762, U.S. Pat. No. 5,693,761, U.S. Pat. No. 5,585,089, and U.S. Pat. No. 5,530,101.

Generally, the goal of making a chimeric antibody is to create a chimera in which the number of amino acids from the intended patient species is maximized. One example is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the variable region or selected CDRs from a rodent antibody often are grafted into a human antibody, replacing the naturally-occurring variable regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. No. 5,585,089, and U.S. Pat. No. 5,693,762; Jones et al., 1986, *Nature* 321:522-525; Riechmann et al., 1988, *Nature* 332:323-27; Verhoeyen et al., 1988, *Science* 239:1534-1536).

In one aspect, the CDRs of the light and heavy chain variable regions of the antibodies provided herein are grafted to framework regions (FRs) from antibodies from the same, or a different, phylogenetic species. For example, the CDRs of the heavy and light chain variable regions $V_H1$, $V_L2$, $V_L1$, and/or $V_L2$ can be grafted to consensus human FRs. To create consensus human FRs, FRs from several human heavy chain or light chain amino acid sequences may be aligned to identify a consensus amino acid sequence. In other embodiments, the FRs of a heavy chain or light chain disclosed herein are replaced with the FRs from a different heavy chain or light chain. In one aspect, rare amino acids in the FRs of the heavy and light chains of SFRP5 antibodies are not replaced, while the rest of the FR amino acids are replaced. A "rare amino acid" is a specific amino acid that is in a position in which this particular amino acid is not usually found in an FR. Alternatively, the grafted variable regions from the one heavy or light chain may be used with a constant region that is different from the constant region of that particular heavy or light chain as disclosed herein. In other embodiments, the grafted variable regions are part of a single chain Fv antibody.

In certain embodiments, constant regions from species other than human can be used along with the human variable region(s) to produce hybrid antibodies.

Fully Human Antibodies

Fully human SFRP5 antibodies are also provided. Methods are available for making fully human antibodies specific for a given antigen without exposing human beings to the antigen ("fully human antibodies"). One specific means provided for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (mAbs) in mouse, an animal that can be immunized with any desirable antigen. Using fully human antibodies can minimize the immunogenic and allergic responses that can sometimes be caused by administering mouse or mouse-derived mAbs to humans as therapeutic agents.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, e.g., Jakobovits et al., 1993, *Proc. Natl. Acad. Sci. USA* 9:2551-2555; Jakobovits et al., 1993, *Nature* 362:255-258; and Bruggermann et al., 1993, *Year in Immunol.* 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WO96/33735 and WO94/02602. Additional methods relating to transgenic mice for making human antibodies are described in U.S. Pat. No. 5,545,807; U.S. Pat. No. 6,713,610; U.S. Pat. No. 6,673,986; U.S. Pat. No. 6,162,963; U.S. Pat. No. 5,545,807; U.S. Pat. No. 6,300,129; U.S. Pat. No. 6,255,458; U.S. Pat. No. 5,877,397; U.S. Pat. No. 5,874,299 and U.S. Pat. No. 5,545,806; in PCT publications WO91/10741, WO90/04036, and in EP 546073B1 and EP 546073A1.

The transgenic mice described above, referred to herein as "HuMab" mice, contain a human immunoglobulin gene minilocus that encodes unrearranged human heavy ([mu] and [gamma]) and [kappa] light chain immunoglobulin sequences, together with targeted mutations that inactivate the endogenous [mu] and [kappa] chain loci (Lonberg et al., 1994, *Nature* 368:856-859). Accordingly, the mice exhibit reduced expression of mouse IgM or [kappa] and in response to immunization, and the introduced human heavy and light chain transgenes undergo class switching and somatic mutation to generate high affinity human IgG [kappa] monoclonal antibodies (Lonberg et al., supra.; Lonberg and Huszar, 1995, *Intern. Rev. Immunol.* 13: 65-93; Harding and Lonberg, 1995, *Ann. N.Y Acad. Sci.* 764:536-

546). The preparation of HuMab mice is described in detail in Taylor et al., 1992, *Nucleic Acids Research* 20:6287-6295; Chen et al., 1993, *International Immunology* 5:647-656; Tuaillon et al., 1994, *J. Immnunol.* 152:2912-2920; Lonberg et al., 1994, *Nature* 368:856-859; Lonberg, 1994, *Handbook of Exp. Pharmacology* 113:49-101; Taylor et al., 1994, *International Immunology* 6:579-591; Lonberg and Huszar, 1995, *Intern. Rev. Immnunol.* 13:65-93; Harding and Lonberg, 1995, *Ann. N.Y Acad. Sci.* 764:536-546; Fishwild et al., 1996, *Nature Biotechnology* 14:845-851; the foregoing references are hereby incorporated by reference in their entirety for all purposes. See, further U.S. Pat. No. 5,545,806; U.S. Pat. No. 5,569,825; U.S. Pat. No. 5,625,126; U.S. Pat. No. 5,633,425; U.S. Pat. No. 5,789,650; U.S. Pat. No. 5,877,397; U.S. Pat. No. 5,661,016; U.S. Pat. No. 5,814,318; U.S. Pat. No. 5,874,299; and U.S. Pat. No. 5,770,429; as well as U.S. Pat. No. 5,545,807; International Publication Nos. WO 93/1227; WO 92/22646; and WO 92/03918, the disclosures of all of which are hereby incorporated by reference in their entirety for all purposes. Technologies utilized for producing human antibodies in these transgenic mice are disclosed also in WO 98/24893, and Mendez et al., 1997, *Nature Genetics* 15:146-156, which are hereby incorporated by reference. For example, the HCo7 and HCo12 transgenic mice strains can be used to generate anti-c-SFRP5 antibodies. Further details regarding the production of human antibodies using transgenic mice are provided below.

Using hybridoma technology, antigen-specific human mAbs with the desired specificity can be produced and selected from the transgenic mice such as those described above. Such antibodies may be cloned and expressed using a suitable vector and host cell, or the antibodies can be harvested from cultured hybridoma cells.

Fully human antibodies can also be derived from phage-display libraries (as disclosed in Hoogenboom et al., 1991, *J. Mol. Biol.* 227:381; and Marks et al., 1991, *J. Mol. Biol.* 222:581). Phage display techniques mimic immune selection through the display of antibody repertoires on the surface of filamentous bacteriophage, and subsequent selection of phage by their binding to an antigen of choice. One such technique is described in PCT Publication No. WO 99/10494 (hereby incorporated by reference).

Bispecific or Bifunctional Antigen Binding Proteins

The antigen binding proteins that are provided also include bispecific and bifunctional antibodies that include one or more CDRs or one or more variable regions as described above. A bispecific or bifunctional antibody in some instances is an artificial hybrid antibody having two different heavy/light chain pairs and two different binding sites. Bispecific antibodies may be produced by a variety of methods including, but not limited to, fusion of hybridomas or linking of Fab' fragments. See, e.g., Songsivilai and Lachmann, 1990, *Clin. Exp. Immunol.* 79:315-321; Kostelny et al., 1992, *J. Immunol.* 148:1547-1553.

Various Other Forms

The SFRP5 binding protein can also be a variant, mimetic, derivative or oligomer based upon the structure of SFRP5 antigen binding proteins have the CDRs, variable regions and/or full length chains as described above in Tables 1-4.

Variants

In one embodiment, for instance, an antigen binding protein is a variant form of the antigen binding proteins disclosed above. For instance, some of the antigen binding proteins have one or more conservative amino acid substitutions in one or more of the heavy or light chains, variable regions or CDRs in Tables 1-4.

Naturally-occurring amino acids may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of the above classes for a member from another class. Such substituted residues may be introduced into regions of the antibody that are homologous with human antibodies, or into the non-homologous regions of the molecule.

In making such changes, according to certain embodiments, the hydropathic index of amino acids may be considered. The hydropathic profile of a protein is calculated by assigning each amino acid a numerical value ("hydropathy index") and then repetitively averaging these values along the peptide chain. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic profile in conferring interactive biological function on a protein is understood in the art (see, e.g., Kyte et al., 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In some aspects, those which are within ±1 are included, and in other aspects, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen-binding or immunogenicity, that is, with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in other embodiments, those which are within ±1 are included, and in still other embodiments, those within ±0.5 are included. In some instances, one may also identify epitopes from primary amino acid sequences on the basis of hydrophilicity. These regions are also referred to as "epitopic core regions."

Exemplary conservative amino acid substitutions are set forth in Table 5.

TABLE 5

Conservative Amino Acid Substitutions

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

A skilled artisan will be able to determine suitable variants of polypeptides as set forth herein using well-known techniques. One skilled in the art may identify suitable areas of the molecule that may be changed without destroying activity by targeting regions not believed to be important for activity. The skilled artisan also will be able to identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the 3-dimensional structure and amino acid sequence in relation to that structure in similar polypeptides. In view of such information, one skilled in the art may predict the alignment of amino acid residues of an antibody with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using assays for SFRP5 activity, thus yielding information regarding which amino acids can be changed and which must not be changed. In other words, based on information gathered from such routine experiments, one skilled in the art can readily determine the amino acid positions where further substitutions should be avoided either alone or in combination with other mutations.

A number of scientific publications have been devoted to the prediction of secondary structure. See, Moult, 1996, *Curr. Op. in Biotech.* 7:422-427; Chou et al., 1974, *Biochem.* 13:222-245; Chou et al., 1974, *Biochemistry* 113:211-222; Chou et al., 1978, *Adv. Enzymol. Relat. Areas Mol. Biol.* 47:45-148; Chou et al., 1979, *Ann. Rev. Biochem.* 47:251-276; and Chou et al., 1979, *Biophys. J.* 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% can have similar structural topologies. The recent growth of the protein structural database (PDB) has provided enhanced predictability of secondary structure, including the potential number of folds within a polypeptide's or protein's structure. See, Holm et al., 1999, *Nucl. Acid. Res.* 27:244-247. It has been suggested (Brenner et al., 1997, *Curr. Op. Struct. Biol.* 7:369-376) that there are a limited number of folds in a given polypeptide or protein and that once a critical number of structures have been resolved, structural prediction will become dramatically more accurate.

Additional methods of predicting secondary structure include "threading" (Jones, 1997, *Curr. Opin. Struct. Biol.* 7:377-387; Sippl et al., 1996, *Structure* 4:15-19), "profile analysis" (Bowie et al., 1991, *Science* 253:164-170; Gribskov et al., 1990, *Meth. Enzym.* 183:146-159; Gribskov et al., 1987, *Proc. Nat. Acad. Sci.* 84:4355-4358), and "evolutionary linkage" (See, Holm, 1999, supra; and Brenner, 1997, supra).

In some embodiments, amino acid substitutions are made that: (1) reduce susceptibility to proteolysis, (2) reduce susceptibility to oxidation, (3) alter binding affinity for forming protein complexes, (4) alter ligand or antigen binding affinities, and/or (4) confer or modify other physicochemical or functional properties on such polypeptides. For example, single or multiple amino acid substitutions (in certain embodiments, conservative amino acid substitutions) may be made in the naturally-occurring sequence. Substitutions can be made in that portion of the antibody that lies outside the domain(s) forming intermolecular contacts). In such embodiments, conservative amino acid substitutions can be used that do not substantially change the structural characteristics of the parent sequence (e.g., one or more replacement amino acids that do not disrupt the secondary structure that characterizes the parent or native antigen binding protein). Examples of art-recognized polypeptide secondary and tertiary structures are described in Proteins, Structures and Molecular Principles (Creighton, Ed.), 1984, W. H. New York: Freeman and Company; Introduction to Protein Structure (Branden and Tooze, eds.), 1991, New York: Garland Publishing; and Thornton et al., 1991, *Nature* 354:105, which are each incorporated herein by reference.

Additional preferred antibody variants include cysteine variants wherein one or more cysteine residues in the parent or native amino acid sequence are deleted from or substituted with another amino acid (e.g., serine). Cysteine variants are useful, inter alia when antibodies must be refolded into a biologically active conformation. Cysteine variants may have fewer cysteine residues than the native antibody, and typically have an even number to minimize interactions resulting from unpaired cysteines.

The heavy and light chains, variable regions domains and CDRs that are disclosed can be used to prepare polypeptides that contain an antigen binding region that can specifically bind to SFRP5. For example, one or more of the CDRs can be incorporated into a molecule (e.g., a polypeptide) covalently or noncovalently to make an immunoadhesion. An immunoadhesion may incorporate the CDR(s) as part of a larger polypeptide chain, may covalently link the CDR(s) to another polypeptide chain, or may incorporate the CDR(s) noncovalently. The CDR(s) enable the immunoadhesion to bind specifically to a particular antigen of interest (e.g., an SFRP5 polypeptide or epitope thereof).

Mimetics

Mimetics (e.g., "peptide mimetics" or "peptidomimetics") based upon the variable region domains and CDRs that are described herein are also provided. These analogs can be peptides, non-peptides or combinations of peptide and non-peptide regions. Fauchere, 1986, *Adv. Drug Res.* 15:29; Veber and Freidinger, 1985, *TINS* p. 392; and Evans et al., 1987, *J. Med. Chem.* 30:1229, which are incorporated herein by reference for any purpose. Peptide mimetics that are structurally similar to therapeutically useful peptides may be used to produce a similar therapeutic or prophylactic effect. Such compounds are often developed with the aid of computerized molecular modeling. Generally, peptidomimetics are proteins that are structurally similar to an antibody displaying a desired biological activity, such as here the ability to specifically bind SFRP5, but have one or more peptide linkages optionally replaced by a linkage selected from: $—CH_2NH—$, $—CH_2S—$, $—CH_2—CH_2—$, —CH—CH-(cis and trans), $—COCH_2—$, $—CH(OH)CH_2—$, and $—CH_2SO—$, by methods well known in the art. Systematic substitution of one or more amino acids of a consensus sequence with a D-amino acid of the same type (e.g., D-lysine in place of L-lysine) may be used in certain embodiments to generate more stable proteins. In addition, constrained peptides comprising a consensus sequence or a substantially identical consensus sequence variation may be generated by methods known in the art (Rizo and Gierasch, 1992, *Ann. Rev. Biochem.* 61:387), incorporated herein by reference), for example, by adding internal cysteine residues capable of forming intramolecular disulfide bridges which cyclize the peptide.

Derivatives

Derivatives of the antigen binding proteins that are described herein are also provided. The derivatized antigen binding proteins can comprise any molecule or substance that imparts a desired property to the antibody or fragment, such as increased half-life in a particular use. The derivatized antigen binding protein can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the antigen binding protein for a particular use (e.g., administration to a subject, such as a human subject, or other in vivo or in vitro uses). Examples of molecules that can be used to derivatize an antigen binding protein include albumin (e.g., human serum albumin) and polyethylene glycol (PEG). Albumin-linked and PEGylated derivatives of antigen binding proteins can be prepared using techniques well known in the art. Certain antigen binding proteins include a pegylated single chain polypeptide as described herein. In one embodiment, the antigen binding protein is conjugated or otherwise linked to transthyretin (TTR) or a TTR variant. The TTR or TTR variant can be chemically modified with, for example, a chemical selected from the group consisting of dextran, poly(n-vinyl pyrrolidone), polyethylene glycols, propropylene glycol homopolymers, polypropylene oxide/ethylene oxide co-polymers, polyoxyethylated polyols and polyvinyl alcohols.

Other derivatives include covalent or aggregative conjugates of SFRP5 antigen binding proteins with other proteins or polypeptides, such as by expression of recombinant fusion proteins comprising heterologous polypeptides fused to the N-terminus or C-terminus of an SFRP5 antigen binding protein. For example, the conjugated peptide may be a heterologous signal (or leader) polypeptide, e.g., the yeast alpha-factor leader, or a peptide such as an epitope tag. SFRP5 antigen binding protein-containing fusion proteins can comprise peptides added to facilitate purification or identification of the SFRP5 antigen binding protein (e.g., poly-His). A SFRP5 antigen binding protein also can be linked to the FLAG peptide as described in Hopp et al., 1988, *Bio/Technology* 6:1204; and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

Oligomers

Oligomers that contain one or more SFRP5 antigen binding proteins may be employed as SFRP5 agonists. Oligomers may be in the form of covalently-linked or non-covalently-linked dimers, trimers, or higher oligomers. Oligomers comprising two or more SFRP5 antigen binding proteins are contemplated for use, with one example being a homodimer. Other oligomers include heterodimers, homotrimers, heterotrimers, homotetramers, heterotetramers, etc.

One embodiment is directed to oligomers comprising multiple SFRP5-binding polypeptides joined via covalent or non-covalent interactions between peptide moieties fused to the SFRP5 antigen binding proteins. Such peptides may be peptide linkers (spacers), or peptides that have the property of promoting oligomerization. Leucine zippers and certain polypeptides derived from antibodies are among the peptides that can promote oligomerization of SFRP5 antigen binding proteins attached thereto, as described in more detail below.

In particular embodiments, the oligomers comprise from two to four SFRP5 antigen binding proteins. The SFRP5 antigen binding protein moieties of the oligomer may be in any of the forms described above, e.g., variants or fragments. Preferably, the oligomers comprise SFRP5 antigen binding proteins that have agonist activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, *Proc. Natl. Acad. Sci. USA* 88:10535; Byrn et al., 1990, *Nature* 344:677; and Hollenbaugh et al., 1992 "Construction of Immunoglobulin Fusion Proteins", in Current Protocols in Immunology, Suppl. 4, pages 10.19.1-10.19.11.

One embodiment is directed to a dimer comprising two fusion proteins created by fusing a SFRP5 antigen binding protein to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 and U.S. Pat. No. 5,426,048 and U.S. Pat. No. 5,262,522, is a single chain polypeptide extending from the N-terminal hinge region to the native C-terminus of the Fc region of a human IgG1 antibody. Another useful Fc polypeptide is the Fc mutein described in U.S. Pat. No. 5,457,035, and in Baum et al., 1994, *EMBO J.* 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

Alternatively, the oligomer is a fusion protein comprising multiple SFRP5 antigen binding proteins, with or without peptide linkers (spacer peptides). Among the suitable peptide linkers are those described in U.S. Pat. No. 4,751,180 and U.S. Pat. No. 4,935,233.

Another method for preparing oligomeric SFRP5 antigen binding protein derivatives involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994. *FEBS Letters* 344:191, hereby incorporated by reference. The use of a modified leucine zipper that allows for stable trimerization of a heterologous protein fused thereto is described in Fanslow et al., 1994, *Semin. Immunol.* 6:267-278. In one approach, recombinant fusion proteins comprising an SFRP5 antigen binding protein fragment or derivative fused to a leucine zipper peptide are expressed in suitable host cells, and the soluble oligomeric SFRP5 antigen binding protein fragments or derivatives that form are recovered from the culture supernatant.

Glycosylation State of SFRP5 Antigen Binding Proteins

The antigen-binding protein may have a glycosylation pattern that is different or altered from that found in the native species. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antigen binding protein is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antigen binding protein amino acid sequence may be altered through changes at the DNA level, particularly by mutating the DNA encoding the target polypeptide at preselected bases such that codons are generated that will translate into the desired amino acids.

Another means of increasing the number of carbohydrate moieties on the antigen binding protein is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, *CRC Crit. Rev, Biochem.*, pp. 259-306.

Removal of carbohydrate moieties present on the starting antigen binding protein may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118:131. Enzymatic cleavage of carbohydrate moieties on polypeptides can be achieved by the use of a variety of endo- and exo-glycosidases as described by Thotakura et al., 1987, *Meth. Enzymol.* 138:350. Glycosylation at potential glycosylation sites may be prevented by the use of the compound tunicamycin as described by Duskin et al., 1982, *J. Biol. Chem.* 257:3105. Tunicamycin blocks the formation of protein-N-glycoside linkages.

Hence, aspects include glycosylation variants of the antigen binding proteins wherein the number and/or type of glycosylation site(s) has been altered compared to the amino acid sequences of the parent polypeptide. In certain embodiments, antibody protein variants comprise a greater or a lesser number of N-linked glycosylation sites than the native antibody. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate or alter this sequence will prevent addition of an N-linked carbohydrate chain present in the native polypeptide. For example, the glycosylation can be reduced by the deletion of an Asn or by substituting the Asn with a different amino acid. In other embodiments, one or more new N-linked sites are created. Antibodies typically have a N-linked glycosylation site in the Fc region.

Antigen Binding Proteins with Labels and Effector Groups

In some embodiments, the antigen-binding protein comprises one or more labels. The term "labeling group" or "label" means any detectable label. Examples of suitable labeling groups include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antigen binding protein via spacer arms of various lengths to reduce potential steric hindrance. Various methods for labeling proteins are known in the art and may be used as is seen fit.

The term "effector group" means any group coupled to an antigen binding protein that acts as a cytotoxic agent. Examples for suitable effector groups are radioisotopes or radionuclides (e.g., $^3$H, $^{14}$C, $^{15}$N, $^{35}$S, $^{90}$Y, $^{99}$Tc, $^{111}$In, $^{125}$I, $^{131}$I). Other suitable groups include toxins, therapeutic groups, or chemotherapeutic groups. Examples of suitable groups include calicheamicin, auristatins, geldanamycin and maytansine. In some embodiments, the effector group is coupled to the antigen binding protein via spacer arms of various lengths to reduce potential steric hindrance.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antigen binding protein via spacer arms of various lengths to reduce potential steric hindrance. Various methods for labeling proteins are known in the art.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, hereby expressly incorporated by reference.

Suitable proteinaceous fluorescent labels also include, but are not limited to, green fluorescent protein, including a *Renilla, Ptilosarcus*, or *Aequorea* species of GFP (Chalfie et al., 1994, *Science* 263:802-805), EGFP (Clontech Labs., Inc., Genbank Accession Number U55762), blue fluorescent protein (BFP, Quantum Biotechnologies, Inc., Quebec, Canada; Stauber, 1998, *Biotechniques* 24:462-471; Heim et al., 1996, *Curr. Biol.* 6:178-182), enhanced yellow fluorescent protein (EYFP, Clontech Labs., Inc.), luciferase (Ichiki et al., 1993, *J. Immnunol.* 150:5408-5417), β galactosidase (Nolan et al., 1988, *Proc. Natl. Acad. Sci. U.S.A.* 8:2603-2607) and *Renilla* (WO92/15673, WO95/07463, WO98/14605, WO98/26277, WO99/49019, U.S. Pat. No. 5,292,658, U.S. Pat. No. 5,418,155, U.S. Pat. No. 5,683,888, U.S. Pat. No. 5,741,668, U.S. Pat. No. 5,777,079, U.S. Pat. No. 5,804,387, U.S. Pat. No. 5,874,304, U.S. Pat. No. 5,876,995, U.S. Pat. No. 5,925,558).

Nucleic Acids Encoding SFRP5 Antigen Binding Proteins

Nucleic acids that encode for the antigen binding proteins described herein, or portions thereof, are also provided, including nucleic acids encoding one or both chains of an antibody, or a fragment, derivative, mutein, or variant thereof, polynucleotides encoding heavy chain variable regions or only CDRs, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids). Table 6 shows exemplary nucleic acid sequences encoding an IgG2 heavy chain constant region and IgG2 lambda and kappa light chain constant regions. Any variable region provided herein may be attached to these constant regions to form complete heavy and light chain sequences. However, it should be understood that these constant regions sequences are provided as specific examples only. In some embodiments, the variable region sequences are joined to other constant region sequences that are known in the art. Exemplary nucleic acid sequences encoding heavy and light chain variable regions are provided in Table 7.

TABLE 6

Exemplary Nucleic Acid Sequences Encoding
Heavy and Light Chain Constant Regions

| Chain Type | SEQ ID NO: | Nucleic Acid Sequence |
|---|---|---|
| IgG2 heavy chain constant region | 12 | gctagcaccaagggcccatcggtcttccccctggcgccct gctccaggagcacctccgagagcacagcggccctgggctg cctggtcaaggactacttccccgaaccggtgacggtgtcg tggaactcaggcgctctgaccagcggcgtgcacaccttcc cagctgtcctacagtcctcaggactctactccctcagcag cgtggtgaccgtgccctccagcaacttcggcacccagacc tacacctgcaacgtagatcacaagcccagcaacaccaagg tggacaagacagttgagcgcaaatgttgtgtcgagtgccc accgtgcccagcaccacctgtggcaggaccgtcagtcttc ctcttccccccaaaacccaaggacaccctcatgatctccc ggacccctgaggtcacgtgcgtggtggtggacgtgagcca cgaagaccccgaggtccagttcaactggtacgtggacggc gtggaggtgcataatgccaagacaaagccacgggaggagc agttcaacagcacgttccgtgtggtcagcgtcctcaccgt tgtgcaccaggactggctgaacggcaaggagtacaagtgc aaggtctccaacaaaggcctcccagccccccatcgagaaaa ccatctccaaaaccaaagggcagccccgagaaccacaggt gtacaccctgcccccatcccgggaggagatgaccaagaac caggtcagcctgacctgcctggtcaaaggcttctacccca gcgacatcgccgtggagtgggagagcaatgggcagccgga gaacaactacaagaccacacctcccatgctggactccgac ggctccttcttcctctacagcaagctcaccgtggacaaga gcaggtggcagcaggggaacgtcttctcatgctccgtgat gcatgaggctctgcacaaccactacacgcagaagagcctc tccctgtctccgggtaaatga |
| IgG2 lambda light chain constant region | 13 | ggtcagcccaaggctgccccctcggtcactctgttcccgc cctcctctgaggagcttcaagccaacaaggccacactggt gtgtctcataagtgacttctacccgggagccgtgacagtg gcctggaaggcagatagcagccccgtcaaggcgggagtgg agaccaccacaccctccaaacaaagcaacaacaagtacgc ggccagcagctatctgagcctgacgcctgagcagtggaag tcccacagaagctacagctgccaggtcacgcatgaaggga gcaccgtggagaagacagtggcccctacagaatgttca |
| IgG2 kappa light chain constant region | 14 | cgtacggtggctgcaccatctgtcttcatcttcccgccat ctgatgagcagttgaaatctggaactgcctctgttgtgtg cctgctgaataacttctatcccagagaggccaaagtacag tggaaggtggataacgccctccaatcgggtaactcccagg agagtgtcacagagcaggacagcaaggacagcacctacag cctcagcagcaccctgacgctgagcaaagcagactacgag aaacacaaagtctacgcctgcgaagtcacccatcagggcc tgagctcgcccgtcacaaagagcttcaacaggggagagtg ttag |

Table 7 shows exemplary nucleic acid sequences encoding heavy chain and light chain variable regions, in which the various CDRH1, CDRH2, CDRH3, CDRL1, CDRL2 and CDRL3 sequences are embedded.

TABLE 7

Exemplary Nucleic Acid Sequences Encoding
Heavy and Light Chain Variable Regions

| Designation | SEQ ID NO: | Nucleic Acid Encoding Sequence |
|---|---|---|
| $V_H1$ | 29 | caggtgcagctggtgcagagcggcgcggaagtgaaaaaac cgggcgcgagcgtgaaagtgagctgcaaagcgagcggcta taccttaccgattattatattaactgggtgcgccaggcg accggcagggcctggaatggatgggccgcatttatccgg gcagcggcaacacctattataacgaaaaatttaaaggccg cgtgaccatgacccgcgataccagcattagcaccgcgtat atggaactgagcagcctgcgcagcgaagataccgcggtgt attattgcgcgcgctatagcgcgagcgcgatggattattg gggccagggcaccctggtgaccgtgagcagc |
| $V_H2$ | 30 | caggtgcagctggtgcagagcggcgcggaagtgaaaaaac cgggcgcgagcgtgaaagtgagctgcaaagcgagcggcta taccttaccgattattatattaactgggtgcgccaggcg accggcagggcctggaatggatgggccgcatttatccgg gcagcggcaacacctattataacgaaaaatttaaaggccg cgtgaccctgaccgcgaaaaaagcagcagcaccgcgtat atggaactgagcagcctgcgcagcgaagataccgcggtgt |

TABLE 7-continued

Exemplary Nucleic Acid Sequences Encoding
Heavy and Light Chain Variable Regions

| Designation | SEQ ID NO: | Nucleic Acid Encoding Sequence |
|---|---|---|
| | | attttttgcgcggcgtatagcgcgagcgcgatggattattg ggccagggcaccctggtgaccgtgagcagc |
| $V_L1$ | 31 | gatattgtgatgacccagagcccggatagcctggcggtga gcctgggcgaacgcgcgaccattaactgccgcgcgagcga aagcgtggatagctatggcaaaagctttatgtattggtat cagcagaaaccgggccagccgccgaaactgctgatttatc tggcgaacaacctggaaagcggcgtgccggatcgctttag cggcagcggcagcggcaccgattttaccctgaccattagc agcctgcaggcggaagatgtggcggtgtattattgccagc agaacaacgaagatccgtggacctttggcggcggcaccaa agtggaaattaaacgc |
| $V_L2$ | 32 | gatgtggtgctgacccagagcccggatagcctggcggtga gcctgggcgaacgcgcgaccattaactgccgcgcgagcga aagcgtggatagctatggcaaaagctttatgtattggtat cagcagaaaccgggccagccgccgaaactgctgatttatc tggcgaacaacctggaaagcggcgtgccggatcgctttag cggcagcggcagccgcaccgattttaccctgaccattagc agcctgcaggcggaagatgtggcggtgtattattgccagc agaacaacgaagatccgtggacctttggcggcggcaccaa agtggaaattaaacgc |

Nucleic acids encoding certain antigen binding proteins, or portions thereof (e.g., full length antibody, heavy or light chain, variable domain, or CDRH1, CDRH2, CDRH3, CDRL1, CDRL2, or CDRL3) may be isolated from B-cells of mice that have been immunized with SFRP5 or an immunogenic fragment thereof. The nucleic acid may be isolated by conventional procedures such as polymerase chain reaction (PCR). Phage display is another example of a known technique whereby derivatives of antibodies and other antigen binding proteins may be prepared. In one approach, polypeptides that are components of an antigen binding protein of interest are expressed in any suitable recombinant expression system, and the expressed polypeptides are allowed to assemble to form antigen binding proteins.

The nucleic acids provided in Tables 6 and 7 are exemplary only. Due to the degeneracy of the genetic code, each of the polypeptide sequences listed in Tables 1-4 or otherwise depicted herein are also encoded by a large number of other nucleic acid sequences besides those provided. One of ordinary skill in the art will appreciate that the present application thus provides adequate written description and enablement for each degenerate nucleotide sequence encoding each antigen binding protein.

An aspect further provides nucleic acids that hybridize to other nucleic acids (e.g., nucleic acids comprising a nucleotide sequence listed in Tables 6 or 7) under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65%, 70%, 75%, 80%, 85%, 90%, 95%, 98% or 99% identical to each other typically remain hybridized to each other.

The basic parameters affecting the choice of hybridization conditions and guidance for devising suitable conditions are set forth by, for example, Sambrook, Fritsch, and Maniatis (2001, Molecular Cloning: A Laboratory Manual, Cold Spring Harbor Laboratory Press, Cold Spring Harbor, N.Y., supra; and Current Protocols in Molecular Biology, 1995, Ausubel et al., eds., John Wiley & Sons, Inc., sections 2.10 and 6.3-6.4), and can be readily determined by those having ordinary skill in the art based on, e.g., the length and/or base composition of the nucleic acid.

Changes can be introduced by mutation into a nucleic acid, thereby leading to changes in the amino acid sequence of a polypeptide (e.g., an antibody or antibody derivative) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at nonessential amino acid residues. Alternatively, one or more mutations can be introduced into a nucleic acid that selectively changes the biological activity of a polypeptide that it encodes. For example, the mutation can quantitatively or qualitatively change the biological activity. Examples of quantitative changes include increasing, reducing or eliminating the activity. Examples of qualitative changes include changing the antigen specificity of an antibody. In one embodiment, a nucleic acid encoding any antigen binding protein described herein can be mutated to alter the amino acid sequence using molecular biology techniques that are well-established in the art.

Another aspect provides nucleic acid molecules that are suitable for use as primers or hybridization probes for the detection of nucleic acid sequences. A nucleic acid molecule can comprise only a portion of a nucleic acid sequence encoding a full-length polypeptide, for example, a fragment that can be used as a probe or primer or a fragment encoding an active portion (e.g., SFRP5 binding portion) of a polypeptide.

Probes based on the sequence of a nucleic acid can be used to detect the nucleic acid or similar nucleic acids, for example, transcripts encoding a polypeptide. The probe can comprise a label group, e.g., a radioisotope, a fluorescent compound, an enzyme, or an enzyme co-factor. Such probes can be used to identify a cell that expresses the polypeptide.

Another aspect provides vectors comprising a nucleic acid encoding a polypeptide or a portion thereof (e.g., a fragment containing one or more CDRs or one or more variable region domains). Examples of vectors include, but are not limited to, plasmids, viral vectors, non-episomal mammalian vectors and expression vectors, for example, recombinant expression vectors. The recombinant expression vectors can comprise a nucleic acid in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see, Voss et al., 1986, *Trends Biochem. Sci.* 11:287, Maniatis et al., 1987, *Science* 236:1237, incorporated by reference herein in their entireties), and those that direct inducible expression of a nucleotide sequence in response to particular treatment or condition (e.g., the metallothionine promoter in mammalian cells and the tet-responsive and/or streptomycin responsive promoter in both prokaryotic and eukaryotic systems (see, id.). It will be appreciated by those skilled in the art that the design of the expression vector can depend on such factors as the choice of the host cell to be transformed, the level of expression of protein desired, etc. The expression vectors can be introduced into host cells to thereby produce proteins or peptides, including fusion proteins or peptides, encoded by nucleic acids as described herein.

Another aspect provides host cells into which a recombinant expression vector has been introduced. A host cell can be any prokaryotic cell (for example, *E. coli*) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

Preparing SFRP5 Antigen Binding Proteins

Non-human antibodies that are provided can be, for example, derived from any antibody-producing animal, such as mouse, rat, rabbit, goat, donkey, or non-human primate (such as monkey (e.g., cynomolgus or rhesus monkey) or ape (e.g., chimpanzee)). Non-human antibodies can be used, for instance, in in vitro cell culture and cell-culture based applications, or any other application where an immune response to the antibody does not occur or is insignificant, can be prevented, is not a concern, or is desired. In certain embodiments, the antibodies may be produced by immunizing with full-length SFRP5 or a fragment thereof. Alternatively, the certain non-human antibodies may be raised by immunizing with amino acids which are segments of SFRP5 that form part of the epitope to which certain antibodies provided herein bind (see infra). The antibodies may be polyclonal, monoclonal, or may be synthesized in host cells by expressing recombinant DNA.

Fully human antibodies may be prepared as described above by immunizing transgenic animals containing human immunoglobulin loci or by selecting a phage display library that is expressing a repertoire of human antibodies.

The monoclonal antibodies (mAbs) can be produced by a variety of techniques, including conventional monoclonal antibody methodology, e.g., the standard somatic cell hybridization technique of Kohler and Milstein, 1975, *Nature* 256:495. Alternatively, other techniques for producing monoclonal antibodies can be employed, for example, the viral or oncogenic transformation of B-lymphocytes. One suitable animal system for preparing hybridomas is the murine system, which is a very well established procedure. Immunization protocols and techniques for isolation of immunized splenocytes for fusion are known in the art. For such procedures, B cells from immunized mice are fused with a suitable immortalized fusion partner, such as a murine myeloma cell line. If desired, rats or other mammals besides can be immunized instead of mice and B cells from such animals can be fused with the murine myeloma cell line to form hybridomas. Alternatively, a myeloma cell line from a source other than mouse may be used. Fusion procedures for making hybridomas also are well known.

In one aspect, methods for generating agonist SFRP5 antigen binding proteins such as agonist monoclonal antibodies are provided in which an antibody-producing animal (e.g., mouse, rat, rabbit, goat, donkey, non-human primate and transgenic animals (e.g., mice) containing human immunological loci) are immunized with an activated form of a SFRP5 protein.

The single chain antibodies that are provided may be formed by linking heavy and light chain variable domain (Fv region) fragments via an amino acid bridge (short peptide linker), resulting in a single polypeptide chain. Such single-chain Fvs (scFvs) may be prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. U.S.A.* 85:5879; Ward et al., 1989, *Nature* 334:544, de Graaf et al., 2002, *Methods Mol Biol.* 178:379-387. Single chain antibodies derived from antibodies provided herein include, but are not limited to scFvs comprising the variable domain combinations of the heavy and light chain variable regions, or combinations of light and heavy chain variable domains which include CDRs.

Antibodies provided herein that are of one subclass can be changed to antibodies from a different subclass using subclass switching methods. Thus, IgG antibodies may be derived from an IgM antibody, for example, and vice versa. Such techniques allow the preparation of new antibodies that possess the antigen binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See, e.g., Lantto et al., 2002, *Methods Mol. Biol.* 178:303-316.

Accordingly, the antibodies that are provided include those comprising, for example, the variable domain combinations described, supra., having a desired isotype (for example, IgA, IgG1, IgG2. IgG3, IgG4, IgE, and IgD) as well as Fab or F(ab')$_2$ fragments thereof. Moreover, if an IgG4 is desired, it may also be desired to introduce a point mutation (CPSCP->CPPCP) in the hinge region as described in Bloom et al., 1997, *Protein Science* 6:407, incorporated by reference herein) to alleviate a tendency to form intra-H chain disulfide bonds that can lead to heterogeneity in the IgG4 antibodies.

Moreover, techniques for deriving antibodies having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., 1992, *BioTechnology* 10:779.

Conservative modifications may be made to the heavy and light chain variable regions described in Table 2, or the CDRs described in Tables 3A and 3B (and corresponding modifications to the encoding nucleic acids) to produce an SFRP5 antigen binding protein having functional and biochemical characteristics. Methods for achieving such modifications are described above.

SFRP5 antigen binding proteins may be further modified in various ways. For example, if they are to be used for therapeutic purposes, they may be conjugated with polyethylene glycol (pegylated) to prolong the serum half-life or to enhance protein delivery. Alternatively, the V region of the subject antibodies or fragments thereof may be fused with the Fc region of a different antibody molecule. The Fc region used for this purpose may be modified so that it does not bind complement, thus reducing the likelihood of inducing cell lysis in the patient when the fusion protein is used as a therapeutic agent. In addition, the subject antibodies or functional fragments thereof may be conjugated with human serum albumin to enhance the serum half-life of the antibody or fragment thereof. Another useful fusion partner for the antigen binding proteins or fragments thereof is transthyretin (TTR). TTR has the capacity to form a tetramer, thus an antibody-TTR fusion protein can form a multivalent antibody which may increase its binding avidity.

Alternatively, substantial modifications in the functional and/or biochemical characteristics of the antigen binding proteins described herein may be achieved by creating substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulkiness of the side chain. A "conservative amino acid substitution" may involve a substitution of a native amino acid residue with a nonnative residue that has little or no effect on the polarity or charge of the amino acid residue at that position. See, Table 5, supra. Furthermore, any native residue in the polypeptide may also be substituted with alanine, as has been previously described for alanine scanning mutagenesis.

Amino acid substitutions (whether conservative or non-conservative) of the subject antibodies can be implemented by those skilled in the art by applying routine techniques. Amino acid substitutions can be used to identify important residues of the antibodies provided herein, or to increase or decrease the affinity of these antibodies for SFRP5.

Methods of Expressing Antigen Binding Proteins

Expression systems and constructs in the form of plasmids, expression vectors, transcription or expression cassettes that comprise at least one polynucleotide as described above are also provided herein, as well host cells comprising such expression systems or constructs.

The antigen binding proteins provided herein may be prepared by any of a number of conventional techniques. For example, SFRP5 antigen binding proteins may be produced by recombinant expression systems, using any technique known in the art. See, e.g., Monoclonal Antibodies, Hybridomas: A New Dimension in Biological Analyses, Kennet et al. (eds.) Plenum Press, New York (1980); and Antibodies: A Laboratory Manual, Harlow and Lane (eds.), Cold Spring Harbor Laboratory Press, Cold Spring Harbor, N.Y. (1988).

Antigen binding proteins can be expressed in hybridoma cell lines (e.g., in particular antibodies may be expressed in hybridomas) or in cell lines other than hybridomas. Expression constructs encoding the antibodies can be used to transform a mammalian, insect or microbial host cell. Transformation can be performed using any known method for introducing polynucleotides into a host cell, including, for example packaging the polynucleotide in a virus or bacteriophage and transducing a host cell with the construct by transfection procedures known in the art, as exemplified by U.S. Pat. No. 4,399,216; U.S. Pat. No. 4,912,040; U.S. Pat. No. 4,740,461; U.S. Pat. No. 4,959,455. The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into nuclei.

Recombinant expression constructs typically comprise a nucleic acid molecule encoding a polypeptide comprising one or more of the following: one or more CDRs provided herein; a light chain constant region; a light chain variable region; a heavy chain constant region (e.g., $C_H1$, $C_H2$ and/or $C_H3$); and/or another scaffold portion of a SFRP5 antigen binding protein. These nucleic acid sequences are inserted into an appropriate expression vector using standard ligation techniques. In one embodiment, the heavy or light chain constant region is appended to the C-terminus of the anti-SFRP5 specific heavy or light chain variable region and is ligated into an expression vector. The vector is typically selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase (see, for example, U.S. Pat. No. 6,270,964, which is hereby incorporated by reference). Suitable expression vectors can be purchased, for example, from Invitrogen Life Technologies or BD Biosciences (formerly "Clontech"). Other useful vectors for cloning and expressing the antibodies and fragments include those described in Bianchi and McGrew, 2003, *Biotech. Biotechnol. Bioeng.* 84:439-44, which is hereby incorporated by reference. Additional suitable expression vectors are discussed, for example, in *Methods Enzynmol.*, vol. 185 (D. V. Goeddel, ed.), 1990, New York: Academic Press.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the SFRP5 antigen binding protein coding sequence; the oligonucleotide sequence encodes polyHis (such as hexaHis), or another "tag" such as FLAG®, HA (hemaglutinin influenza virus), or myc, for which commercially available antibodies exist. This tag is typically fused to the polypeptide upon expression of the polypeptide, and can serve as a means for affinity purification or detection of the SFRP5 antigen binding protein from the host cell. Affinity purification can be accomplished, for example, by column chromatography using antibodies against the tag as an affinity matrix. Optionally, the tag can subsequently be removed from the purified SFRP5 antigen binding protein by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thyrnidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antigen binding protein that binds SFRP5 polypeptide. As a result, increased quantities of a polypeptide such as an antigen binding protein are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or pro-sequences to improve glycosylation or yield. For example, one may alter the peptidase cleavage site of a particular signal peptide, or add prosequences, which also may affect glycosylation. The final protein product may have, in the −1 position (relative to the first amino acid of the mature protein), one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning will typically contain a promoter that is recognized by the host organism and operably linked to the molecule encoding the SFRP5 antigen binding protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe a gene to which they are operably linked, that is, with little or no control over gene expression. A large number of promoters, recognized by a variety of potential host cells, are well known. A suitable promoter is operably linked to the DNA encoding heavy chain or light chain comprising a SFRP5 antigen binding protein by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus, and Simian Virus 40 (SV40). Other suitable mammalian promoters include heterologous mammalian promoters, for example, heat-shock promoters and the actin promoter.

An enhancer sequence may be inserted into the vector to increase transcription of DNA encoding light chain or heavy chain comprising a SFRP5 antigen binding protein by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, Nature 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

The expression vectors that are provided may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain, a heavy chain, or a light chain and a heavy chain comprising a SFRP5 antigen binding sequence has been inserted into the proper site of the vector, the completed vector may be inserted into a suitable host cell for amplification and/or polypeptide expression. The transformation of an expression vector for an antigen-binding protein into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes an antigen binding protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and constitutively produce antigen binding proteins with SFRP5 binding properties. In another embodiment, a cell line from the B cell lineage that does not make its own antibody but has a capacity to make and secrete a heterologous antibody can be selected.

Use of SFRP5 Antigen Binding Proteins in Therapy

Antigen binding proteins that specifically bind to SFRP5 can also be used to treat a metabolic condition or disorder in a patient in need thereof. In one embodiment, the metabolic disorder to be treated is diabetes, e.g., type 2 diabetes. In another embodiment, the metabolic condition or disorder is obesity. In other embodiments the metabolic condition or disorder is dyslipidemia, elevated glucose levels, elevated insulin levels or diabetic nephropathy. For example, a metabolic condition or disorder that can be treated or ameliorated using a SFRP5 binding peptide includes a state in which a human subject has a fasting blood glucose level of 125 mg/dL or greater, for example 130, 135, 140, 145, 150, 155, 160, 165, 170, 175, 180, 185, 190, 195, 200 or greater than 200 mg/dL. Blood glucose levels can be determined in the fed or fasted state, or at random. The metabolic condition or disorder can also comprise a condition in which a subject is at increased risk of developing a metabolic condition. For a human subject, such conditions include a fasting blood glucose level of 100 mg/dL. Conditions that can be treated using a pharmaceutical composition comprising a SFRP5 binding protein can also be found in the American Diabetes Association Standards of Medical Care in Diabetes Care-2011, American Diabetes Association, Diabetes Care Vol. 34, No. Supplement 1, S11-S61, 2010.

In application, a metabolic disorder or condition, such as Type 2 diabetes, elevated glucose levels, elevated insulin levels, dyslipidemia, obesity or diabetic nephropathy, can be treated by administering a therapeutically effective dose of a SFRP5 binding protein to a patient in need thereof. The administration can be performed as described herein, such as by i.v. injection, intraperitoneal (i.p.) injection, subcutaneous injection, intramuscular injection, or orally in the form of a tablet or liquid formation. In some situations, a therapeutically effective or preferred dose of a SFRP5 binding protein can be determined by a clinician. A therapeutically effective dose of SFRP5 binding protein will depend, inter alia, upon the administration schedule, the unit dose of agent administered, whether the SFRP5 binding protein is administered in combination with other therapeutic agents, the immune status and the health of the recipient. The term "therapeutically effective dose," as used herein, means an amount of SFRP5 binding protein that elicits a biological or medicinal response in a tissue system, animal, or human being sought by a researcher, medical doctor, or other clinician, which includes alleviation or amelioration of the symptoms of the disease or disorder being treated, i.e., an amount of a SFRP5 binding protein that supports an observable level of one or more desired biological or medicinal response, for example lowering blood glucose, insulin, triglyceride, or cholesterol levels; reducing body weight; or improving glucose tolerance, energy expenditure, or insulin sensitivity.

It is noted that a therapeutically effective dose of a SFRP5 binding protein can also vary with the desired result. Thus, for example, in situations in which a lower level of blood glucose is indicated a dose of SFRP5 binding protein will be correspondingly higher than a dose in which a comparatively lower level of blood glucose is desired. Conversely, in situations in which a higher level of blood glucose is indicated a dose of SFRP5 binding protein will be correspondingly lower than a dose in which a comparatively higher level of blood glucose is desired.

In various embodiments, a subject is a human having a blood glucose level of 100 mg/dL or greater can be treated with a SFRP5 binding protein.

In one embodiment, a method of the instant disclosure comprises first measuring a baseline level of one or more metabolically-relevant compounds such as glucose, insulin, cholesterol, lipid in a subject. A pharmaceutical composition comprising a SFRP5 binding protein is then administered to the subject. After a desired period of time, the level of the one or more metabolically-relevant compounds (e.g., blood glucose, insulin, cholesterol, lipid) in the subject is again measured. The two levels can then be compared in order to determine the relative change in the metabolically-relevant compound in the subject. Depending on the outcome of that comparison another dose of the pharmaceutical composition comprising a SFRP5 binding protein can be administered to achieve a desired level of one or more metabolically-relevant compound.

It is noted that a pharmaceutical composition comprising a SFRP5 binding protein can be co-administered with another compound. The identity and properties of compound co-administered with the SFRP5 binding protein will depend on the nature of the condition to be treated or ameliorated. A non-limiting list of examples of compounds that can be administered in combination with a pharmaceutical composition comprising a SFRP5 binding protein include rosiglitizone, pioglitizone, repaglinide, nateglinide, metformin, exenatide, stiagliptin, pramlintide, glipizide, glimepirideacarbose, and miglitol.

Pharmaceutical Formulations and Administration

Method of using the disclosed antigen binding proteins are also provided. In some methods, an antigen binding protein is provided to a patient that inhibits SFRP5 activity.

Pharmaceutical compositions that comprise a SFRP5 antigen binding protein are also provided and can be utilized in any of the preventive and therapeutic methods disclosed herein. In an embodiment, a therapeutically effective amount of one or a plurality of the antigen binding proteins and a pharmaceutically acceptable diluent, carrier, solubilizer, emulsifier, preservative, and/or adjuvant are also provided. Acceptable formulation materials are nontoxic to recipients at the dosages and concentrations employed.

Acceptable formulation materials are nontoxic to recipients at the dosages and concentrations employed. In specific embodiments, pharmaceutical compositions comprising a therapeutically effective amount of a SFRP5 antigen binding protein are provided.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-betacyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. REMINGTON'S PHARMACEUTICAL SCIENCES, 18" Edition, (A. R. Genrmo, ed.), 1990, Mack Publishing Company provides additional details and options for suitable agents that can be incorporated into the pharmaceutical compositions.

In certain embodiments, the optimal pharmaceutical composition will be determined by one skilled in the art depending upon, for example, the intended route of administration, delivery format and desired dosage. See, for example, *Remington's Pharmaceutical Sciences*, supra. In certain embodiments, such compositions may influence the physical state, stability, rate of in vivo release and rate of in vivo clearance of the antigen binding proteins disclosed. In certain embodiments, the primary vehicle or carrier in a pharmaceutical composition may be either aqueous or non-aqueous in nature. For example, a suitable vehicle or carrier may be water for injection or physiological saline solution. In certain embodiments, SFRP5 antigen binding protein compositions may be prepared for storage by mixing the selected composition having the desired degree of purity with optional formulation agents (*Remington's Pharmaceutical Sciences*, supra) in the form of a lyophilized cake or an aqueous solution. Further, in certain embodiments, the SFRP5 antigen binding protein may be formulated as a lyophilizate using appropriate excipients such as sucrose.

The pharmaceutical compositions can be selected for parenteral delivery. Alternatively, the compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions may be provided in the form of a pyrogen-free, parenterally acceptable aqueous solution comprising the desired human SFRP5 antigen binding protein in a pharmaceutically acceptable vehicle. A particularly suitable vehicle for parenteral injection is sterile distilled water in which the SFRP5 antigen binding protein is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antigen binding protein.

Certain pharmaceutical compositions are formulated for inhalation. In some embodiments, SFRP5 antigen binding proteins are formulated as a dry, inhalable powder. In specific embodiments, SFRP5 antigen binding protein inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins. Some formulations can be administered orally. SFRP5 antigen binding proteins that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and presystemic degradation is minimized. Additional agents can be included to facilitate absorption of the SFRP5 antigen binding protein. Diluents, flavorings, low melting point waxes, vegetable oils, lubricants, suspending agents, tablet disintegrating agents, and binders may also be employed.

Some pharmaceutical compositions comprise an effective quantity of one or a plurality of SFRP5 antigen binding proteins in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving SFRP5 binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, *Biopolymers* 2:547-556), poly (2-hydroxyethyl-inethacrylate) (Langer et al., 1981, *J. Biomed. Mater. Res.* 1: 167-277 and Langer, 1982, *Chem. Tech.* 12:98-105), ethylene vinyl acetate (Langer et al., 1981, supra) or poly-D(−)-3-hydroxybutyric acid (European Patent Application Publication No. EP 133,988). Sustained release compositions may also include liposomes that can be prepared by any of several methods known in the art. See, e.g., Eppstein et al., 1985, *Proc. Natl. Acad. Sci. U.S.A.*

82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

In certain formulations, an antigen binding protein has a concentration of at least 10 mg/ml, 20 mg/ml, 30 mg/ml, 40 mg/ml, 50 mg/ml, 60 mg/ml, 70 mg/ml, 80 mg/ml, 90 mg/ml, 100 mg/ml or 150 mg/ml. In one embodiment, a pharmaceutical composition comprises the antigen binding protein, a buffer and polysorbate. In other embodiments, the pharmaceutical composition comprises an antigen binding protein, a buffer, sucrose and polysorbate. An example of a pharmaceutical composition is one containing 50-100 mg/ml of antigen binding protein, 5-20 mM sodium acetate, 5-10% w/v sucrose, and 0.002-0.008% w/v polysorbate. Certain, compositions, for instance, contain 65-75 mg/ml of an antigen binding protein in 9-11 mM sodium acetate buffer, 8-10% w/v sucrose, and 0.005-0.006% w/v polysorbate. The pH of certain such formulations is in the range of 4.5-6. Other formulations have a pH of 5.0-5.5 (e.g., pH of 5.0, 5.2 or 5.4).

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. Kits for producing a single-dose administration unit are also provided. Certain kits contain a first container having a dried protein and a second container having an aqueous formulation. In certain embodiments, kits containing single and multi-chambered pre-filled syringes (e.g., liquid syringes and lyosyringes) are provided. The therapeutically effective amount of a SFRP5 antigen binding protein-containing pharmaceutical composition to be employed will depend, for example, upon the therapeutic context and objectives. One skilled in the art will appreciate that the appropriate dosage levels for treatment will vary depending, in part, upon the molecule delivered, the indication for which the SFRP5 antigen binding protein is being used, the route of administration, and the size (body weight, body surface or organ size) and/or condition (the age and general health) of the patient. In certain embodiments, the clinician may titer the dosage and modify the route of administration to obtain the optimal therapeutic effect.

A typical dosage can range from about 1 µg/kg to up to about 30 mg/kg or more, depending on the factors mentioned above. In specific embodiments, the dosage can range from 10 µg/kg up to about 35 mg/kg, optionally from 0.1 mg/kg up to about 35 mg/kg, alternatively from 0.3 mg/kg up to about 20 mg/kg. In some applications, the dosage is from 0.5 mg/kg to 20 mg/kg and in other applications the dosage is from 21-100 mg/kg. In some instances, an antigen binding protein is dosed at 0.3-20 mg/kg. The dosage schedule in some treatment regimens is at a dose of 0.3 mg/kg qW-20 mg/kg qW.

Dosing frequency will depend upon the pharmacokinetic parameters of the particular SFRP5 antigen binding protein in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Appropriate dosages may be ascertained through use of appropriate dose-response data. In certain embodiments, the antigen binding proteins can be administered to patients throughout an extended time period. In certain embodiments, the antigen binding protein is dosed every two weeks, every month, every two months, every three months, every four months, every five months, or every six months.

The route of administration of the pharmaceutical composition is in accord with known methods, e.g., orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

It also may be desirable to use SFRP5 antigen binding protein pharmaceutical compositions according to the disclosed ex vivo. In such instances, cells, tissues or organs that have been removed from the patient are exposed to SFRP5 antigen binding protein pharmaceutical compositions after which the cells, tissues and/or organs are subsequently implanted back into the patient.

In particular, antigen binding proteins that specifically bind to SFRP5 can be delivered by implanting certain cells that have been genetically engineered, using methods such as those described herein and known in the art, to express and secrete the polypeptide. In certain embodiments, such cells can be animal or human cells, and can be autologous, heterologous, or xenogeneic. In certain embodiments, the cells can be immortalized. In other embodiments, in order to decrease the chance of an immunological response, the cells can be encapsulated to avoid infiltration of surrounding tissues. In further embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

Combination Therapy

Also provided herein are compositions comprising a SFRP5 antigen binding protein and one or more additional therapeutic agents, as well as methods in which such agents are administered concurrently or sequentially with a SFRP5 antigen binding protein for use in the preventive and therapeutic methods disclosed herein. The one or more additional agents can be co-formulated with a SFRP5 antigen binding protein or can be co-administered with a SFRP5 antigen binding protein. In general, the therapeutic methods, compositions and compounds may also be employed in combination with other therapeutics in the treatment of various disease states, with the additional agents being administered concurrently.

For examples, the antigen binding proteins can be administered in combination with one or more of the type 2 diabetes or obesity treatments currently available. These treatments for diabetes include biguanide (metaformin), and sulfonylureas (such as glyburide, glipizide). Additional treatments directed at maintaining glucose homeostasis include PPAR gamma agonists (pioglitazone, rosiglitazone); glinides (meglitinide, repaglinide, and nateglinide); DPP-4 inhibitors (Januvia® and Onglyza®) and alpha glucosidase inhibitors (acarbose, voglibose). Additional combination treatments for diabetes include injectable treatments such as insulin and incretin mimetics (Byetta®, Exenatide®), other GLP-1 (glucagon-like peptide) analogs such as Victoza® (liraglutide), other GLP-1R agonists and Symlin® (pramlintide). Additional combination treatments directed at weight loss include Meridia® and Xenical®.

Kits

Also provided are kits for practicing the disclosed methods. Such kits can comprise a pharmaceutical composition such as those described herein, including nucleic acids encoding the peptides or proteins provided herein, vectors and cells comprising such nucleic acids, and pharmaceutical compositions comprising such nucleic acid-containing compounds, which can be provided in a sterile container. Optionally, instructions on how to employ the provided pharmaceutical composition in the treatment of a metabolic disorder can also be included or be made available to a patient or a medical service provider.

In one aspect, a kit comprises (a) a pharmaceutical composition comprising a therapeutically effective amount of a SFRP5 binding protein; and (b) one or more containers for the pharmaceutical composition. Such a kit can also comprise instructions for the use thereof; the instructions can be tailored to the precise metabolic disorder being treated. The instructions can describe the use and nature of the materials provided in the kit. In certain embodiments, kits include instructions for a patient to carry out administration to treat a metabolic disorder, such as elevated glucose levels, elevated insulin levels, obesity, type 2 diabetes, dyslipidemia or diabetic nephropathy.

Instructions can be printed on a substrate, such as paper or plastic, etc., and can be present in the kits as a package insert, in the labeling of the container of the kit or components thereof (e.g., associated with the packaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, such as over the internet, are provided. An example of this embodiment is a kit that includes a web address where the instructions can be viewed and/or from which the instructions can be downloaded.

Often it will be desirable that some or all components of a kit are packaged in suitable packaging to maintain sterility. The components of a kit can be packaged in a kit containment element to make a single, easily handled unit, where the kit containment element, e.g., box or analogous structure, may or may not be an airtight container, e.g., to further preserve the sterility of some or all of the components of the kit.

Use of SFRP5 Antigen Binding Proteins for Diagnostic Purposes

The SFRP5 binding proteins that are provided herein are useful for detecting SFRP5 in biological samples. For instance, the SFRP5 antigen binding proteins can be used in diagnostic assays, e.g., binding assays to detect and/or quantify SFRP5 expressed in serum.

The antigen binding proteins of the described can be used for diagnostic purposes to detect, diagnose, or monitor diseases and/or conditions associated with SFRP5. The disclosed antigen binding proteins provide a means for the detection of the presence of SFRP5 in a sample using classical immunohistological methods known to those of skill in the art (e.g., Tijssen, 1993, *Practice and Theory of Enzyme Immunoassays*, Vol 15 (Eds R. H. Burdon and P. H. van Knippenberg, Elsevier, Amsterdam); Zola, 1987, *Monoclonal Antibodies: A Manual of Techniques*, pp. 147-158 (CRC Press, Inc.); Jalkanen et al., 1985, *J. Cell. Biol.* 101:976-985; Jalkanen et al., 1987, *J. Cell Biol.* 105:3087-3096). The detection of SFRP5 can be performed in vivo or in vitro.

Diagnostic applications provided herein include use of the antigen binding proteins to detect expression of SFRP5. Examples of methods useful in the detection of the presence of SFRP5 include immunoassays, such as the enzyme linked immunosorbent assay (ELISA) and the radioimmunoassay (RIA).

For diagnostic applications, the antigen binding protein typically will be labeled with a detectable labeling group. Suitable labeling groups include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I) fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antigen binding protein via spacer arms of various lengths to reduce potential steric hindrance. Various methods for labeling proteins are known in the art and may be used.

In some embodiments, the SFRP5 antigen binding protein is isolated and measured using techniques known in the art. See, for example, Harlow and Lane, 1988, *Antibodies: A Laboratory Manual*, New York: Cold Spring Harbor (ed. 1991 and periodic supplements); John E. Coligan, ed., 1993, *Current Protocols In Immunology* New York: John Wiley & Sons.

Another aspect of the disclosed provides for detecting the presence of a test molecule that competes for binding to SFRP5 with the antigen binding proteins provided. An example of one such assay would involve detecting the amount of free antigen binding protein in a solution containing an amount of SFRP5 in the presence or absence of the test molecule. An increase in the amount of free antigen binding protein (i.e., the antigen binding protein not bound to SFRP5) would indicate that the test molecule is capable of competing for SFRP5 binding with the antigen binding protein. In one embodiment, the antigen binding protein is labeled with a labeling group. Alternatively, the test molecule is labeled and the amount of free test molecule is monitored in the presence and absence of an antigen binding protein.

EXAMPLES

The following examples, including the experiments conducted and the results achieved, are provided for illustrative purposes only and are not to be construed as limiting the scope of the appended claims.

Example 1

Preparation of Anti-SFRP5 Monoclonal Antibodies

Molecular cloning of mouse SFRP5:

Mouse SFRP5 cDNAs (GenBank Accession No NM_018780.3) encoding full-length SFRP5 were cloned into mammalian cell expression vectors. Commonly used tags (for example, His and huFc) were employed to facilitate secretion and subsequent detection/purification. For DNA immunization, additional T helper cell epitope was added to boost immune response.

Stable Expression of SFRP5 in CHO-S Cells:

CHO-S cells (Invitrogen) were transfected with SFRP5 plasmid DNA and Lipofectamine LTX (Invitrogen). Cells were grown in suspension in FreeStyle CHO expression medium (Invitrogen) and selected with puromycin (10 µg/ml) for a week to establish stable transfectant pools.

Generation of Soluble SFRP5-huFc Proteins:

Soluble mouse SFRP5 was generated from stably-transfected CHO-S cells as described above. Cells were grown in FreeStyle CHO expression medium supplemented with puromycin (10 µg/ml) for 7 days and conditioned media ("CM") were harvested for purification. Purifications were performed by passing CM over a MabSelect SuRe (GE Healthcare Life Sciences) affinity column. Bound antibodies were eluted and further purified with Superdex 200 gel filtration column.

Immunization:

C57BL/6 animals were immunized with recombinant soluble SFRP5-huFc proteins or DNA encoding full length mouse SFRP5 via gene gun (Bio-Rad). Sera were collected 4-6 weeks after the first immunization and specific titers were determined by ELISA.

Hybridoma Fusion and Culture:

Animals exhibiting satisfactory titers were identified, and lymphocytes were obtained from draining lymph nodes and spleens. Lymphocytes were dissociated from lymphoid tissues in a suitable medium (for example, Dulbecco's Modified Eagle Medium; DMEM; obtainable from Invitrogen, Carlsbad, Calif.) to release the cells from the tissues, and suspended in DMEM.

B cells were fused with suitable fusion partner, for example, nonsecretory myeloma P3X63Ag8.653 cells (American Type Culture Collection CRL 1580). Lymphocytes were mixed with fusion partner cells at a ratio of 1:1. Electrofusion was performed with BTX ECM2001 (Harvard Apparatus).

The fused cells were gently pelleted (300×g 10 minutes) and resuspended in selection media (for example, DMEM containing hypoxanthine-aminopterin-thymidine [HAT] and other supplemental materials as necessary). Cells were distributed into 384-well plates using standard techniques to maximize clonality of the resulting colonies. After several days of culture, the hybridoma supernatants were collected and subjected to screening assays as detailed in the Examples below, including confirmation of binding to muSFRP5. Positive cells were further selected and subjected to standard cloning and subcloning techniques. Clonal lines were expanded in vitro, and the secreted mouse antibodies obtained for analysis.

Selection of SFRP5 Specific Binding Antibodies by ELISA:

After 9 days of culture, hybridoma supernatants were screened for SFRP5-specific antibodies by ELISA. Briefly, 384-well Nunc maxisorp plates (Thermo Scientific) were coated with 0.5 µg/ml soluble SFRP5-huFc and blocked with 1% BSA. Then, 25 µL/well of hybridoma supernatant was added, followed by plate washing and addition of 25 µL/well of goat anti-mouse IgG(H+L)-HRP secondary antibody (Jackson Immunoresearch, West Grove, Pa.). Plates were washed and HRP substrates were added for color development and OD reading. The hybridoma supernatants displaying positive signals on first round ELISA screening were subject to counter screen of binding to huFc and muSFRP3 by ELISA. Hybridomas secreting specific anti-muSFRP5 IgGs were advanced for subcloning and in vitro functional assays.

Eighteen anti-SFRP5 antibody subclones were prepared. The equilibrium constant $K_D(M)$, association constant, $k_{on}$ (1/Ms), dissociation constant, $k_{off}$ (1/s), and epitope bin are summarized in Table 8.

TABLE 8

Anti-SFRP5 Antibody Subclones

| Subclone ID | $K_D$ (M) | $k_{on}$ (1/Ms) | $k_{off}$ (1/s) | epitope bin |
|---|---|---|---|---|
| 1G14.1 | 4.14E−10 | 1.26E+05 | 5.20E−05 | 1 |
| 1G14.2 | 4.93E−10 | 1.49E+05 | 7.35E−05 | 1 |
| 3N22.1 | 4.61E−10 | 1.07E+05 | 4.95E−05 | 2 |
| 3N22.2 | 5.30E−10 | 1.12E+05 | 5.91E−05 | 2 |
| 10H4.1 | 5.71E−10 | 1.08E+05 | 6.19E−05 | 2 |
| 10H4.2 | 5.79E−10 | 1.04E+05 | 6.00E−05 | 2 |
| 12E6.1 | 5.55E−10 | 1.04E+05 | 5.78E−05 | 2 |
| 12E6.2 | 6.40E−10 | 1.12E+05 | 7.16E−05 | 2 |
| 14J3.5 | 6.88E−10 | 1.51E+05 | 1.04E−04 | 1 |
| 14J3.6 | 6.67E−10 | 1.46E+05 | 9.73E−05 | 1 |
| 17O2.1 | 3.11E−09 | 1.48E+04 | 4.61E−05 | 3 |
| 17O2.2 | 2.23E−09 | 1.84E+04 | 4.11E−05 | 3 |
| 20I9.1 | 7.07E−10 | 1.45E+05 | 1.03E−04 | 1 |
| 20I9.2 | 6.96E−10 | 1.62E+05 | 1.13E−04 | 1 |
| 24C18.2 | 5.64E−10 | 1.17E+05 | 6.60E−05 | 2 |
| 24C18.3 | 6.58E−10 | 1.12E+05 | 7.36E−05 | 2 |
| 24P2.1 | 7.53E−10 | 1.48E+05 | 1.11E−04 | 1 |
| 24P2.2 | 6.89E−10 | 1.74E+05 | 1.20E−04 | 1 |

Example 2

Ex Vivo Activity of Selected Anti-SFRP5 Antibodies

The anti-SFRP5 monoclonal antibodies obtained as described in Table 8 were tested utilizing a TCF/lef-luciferase reporter cell line in which luciferase expression is under the control of the canonical Wnt pathway. When cells transfected with the TCF/lef-luciferase construct are exposed to biologically active Wnt, luciferase activity is induced. The Wnt induced luciferase activity can be suppressed by adding recombinant SFRP5 protein to the cells. The subsequent addition of an anti-mSFRP5 antibody is expected to restore Wnt activity by neutralizing SFRP5, thus resulting in increased luciferase expression. Antibodies were thus tested to determine whether they were capable of restoring luciferase expression in TCF/lef-luciferase cells treated with both recombinant Wnt3a and SFRP5. Luciferase activity was determined as described below.

On day zero, freshly trypsinized TCF/293 cells (BPS Biosciences) were seeded on 96 well plates at $7 \times 10^4$ cells per well. On day 1, cells were washed with PBS and recombinant proteins (mouse Wnt3a, mouse-SFRP5-hemi-Fc protein, and/or anti-SFRP5 monoclonal antibodies at optimized concentrations) were added to the cells in OPTI-MEM media (Gibco) with 0.1% human serum albumin.

After two days, the luciferase assay was performed according to the manufacturer's protocol using the Bright-Glo luciferase assay kit (Promega). Luminescence was measured using a luminometer.

Figure 2:
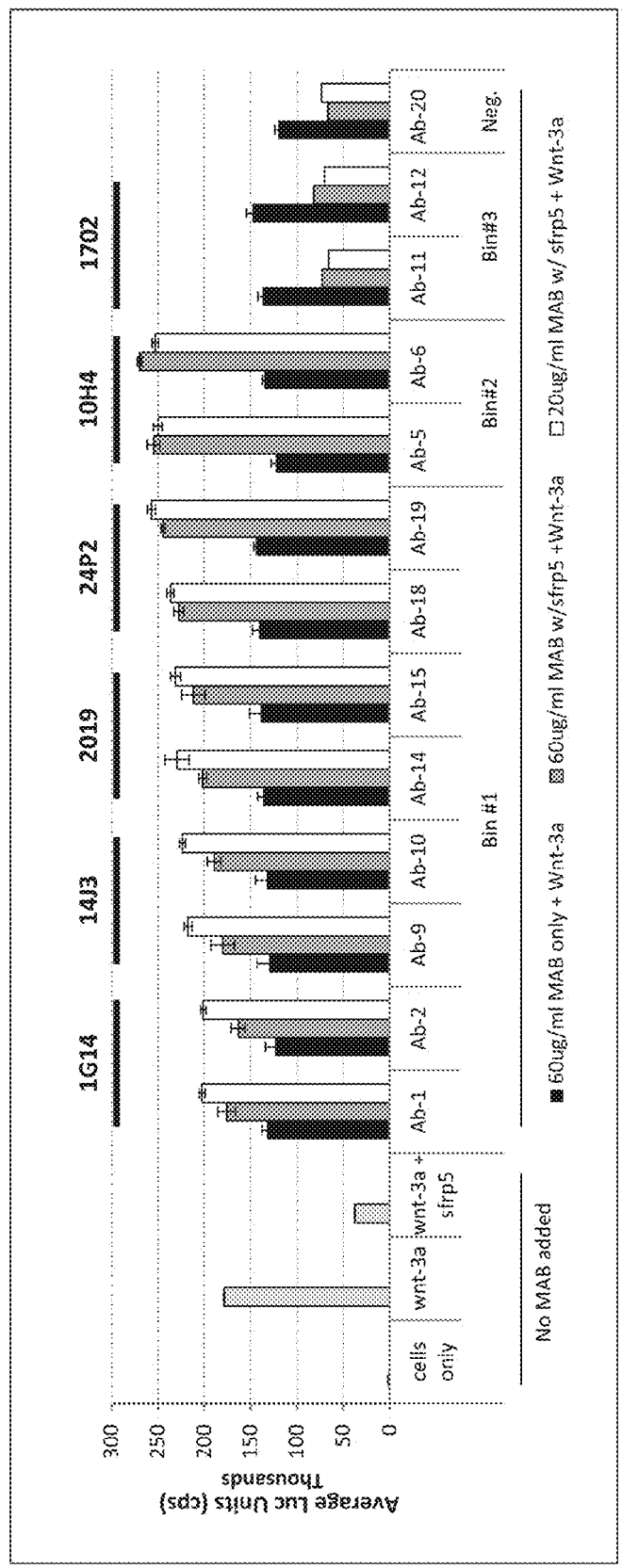
FIG. 2 is a bar graph showing the results of a 293/TCF luciferase cell assay demonstrating the effect of anti-SFRP5 monoclonal antibody subclones to neutralize the inhibitory effect of recombinant mouse SFRP5-hemiFc protein (1.66 µg/ml) on Wnt3a (0.1 µg/ml). This bar graph shows the results of subclones 1G14, 14J3, 2019 and 24P2 (epitope bin 1), 10H4 (epitope bin 2), and 1702 (epitope bin 3). TCF/LEF Reporter (Luc)-HEK293 cell line from BPS Biosciences (San Diego, Calif.). Wnt3a from R&D Systems.

Luminescent signals were used to plot a dose-response curve to show the effect of recombinant SFRP5 (6 µg/ml) on increasing concentrations of recombinant mouse Wnt3a, a bar graph to show the dose-dependent effect of recombinant mouse-Sfrp5-hemi-Fc protein on a constant concentration of recombinant mouse Wnt3a (200 ng/ml), and a bar graph showing the effect of the anti-Sfrp5 monoclonal antibodies (60 ug/ml or 20 ug/ml) on cells treated with recombinant mouse Wnt3a (100 ng/ml) plus or minus recombinant mouse-Sfrp5-hemi-Fc protein. See FIGS. 1-2.

Example 3

In Vivo Pharmacokinetics (PK) of Selected Anti-SFRP5 Antibodies

Figure 3:
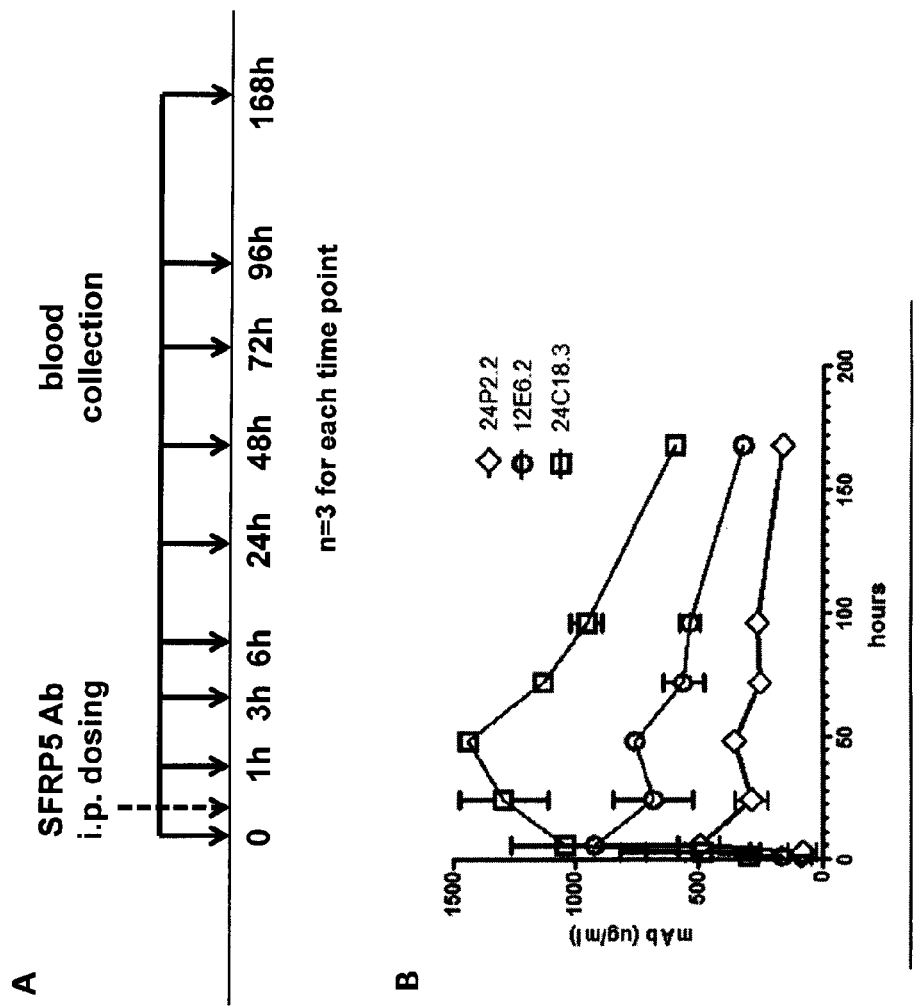
FIG. 3 is a timeline and plot for the in vivo study evaluating the pharmacokinetic properties of anti-SFRP5 monoclonal antibody subclones. B6.V-Lep$^{ob}$/J male mice (3 each for each time point) were injected i.p. with one of the anti-SFRP5 monoclonal antibody subclones. Blood was collected before injection (0) and 1, 3, 6, 24, 48, 72, 96 and 168 hours post injection. The plot shows the concentration of monoclonal antibody in the blood at each time point. Data for subclones 24P2.2 (epitope bin 1), 12E6.2 (epitope bin 2) and 24C18.3 (epitope bin 2) are shown.

Six-week old male B6.V-Lep$^{ob}$/J mice (Jackson Labs) were injected intraperitoneally (i.p.) with one of the anti-SFRP5 monoclonal antibody subclones, i.e., 24P2.2 (epitope bin 1), 12E6.2 (epitope bin 2) and 24C18.3 (epitope bin 2). Blood was collected before injection (0) and 1, 3, 6, 24, 48, 72, 96 and 168 hours post injection. See FIG. 3A. Serum protein levels of anti-SFRP5 antibodies were measured by an anti-SFRP5 ELISA assay. The concentration of monoclonal antibody in the blood (g/mL) at each time point is shown in FIG. 3B. This data demonstrates that the PK of the anti-SFRP5 antibodies is adequately robust and should be suitable for dosing 2-times per week.

Example 4

In Vivo Activity of Selected Anti-SFRP5 Antibodies

Six-week old male B6.V-Lep$^{ob}$/J mice (Jackson Labs) were randomized into 5 groups (n=12). The mice were injected intraperitoneally (i.p.), with 30 mgs/kg of one of the anti-SFRP5 monoclonal antibody subclones two times weekly over the four week study. Group 1 was injected with IgG control, Group 2 was injected with anti-SFRP5 subclone 24P2.2 (epitope bin 1), Group 3 was injected with anti-SFRP5 subclone 12E6.2 (epitope bin 2), Group 4 was injected with anti-SFRP5 subclone 24C18.3 (epitope bin 2), and Group 5 was injected with anti-SFRP subclone 17O2.1 (epitope bin 3).

Glucose Tolerance.

Figure 4:
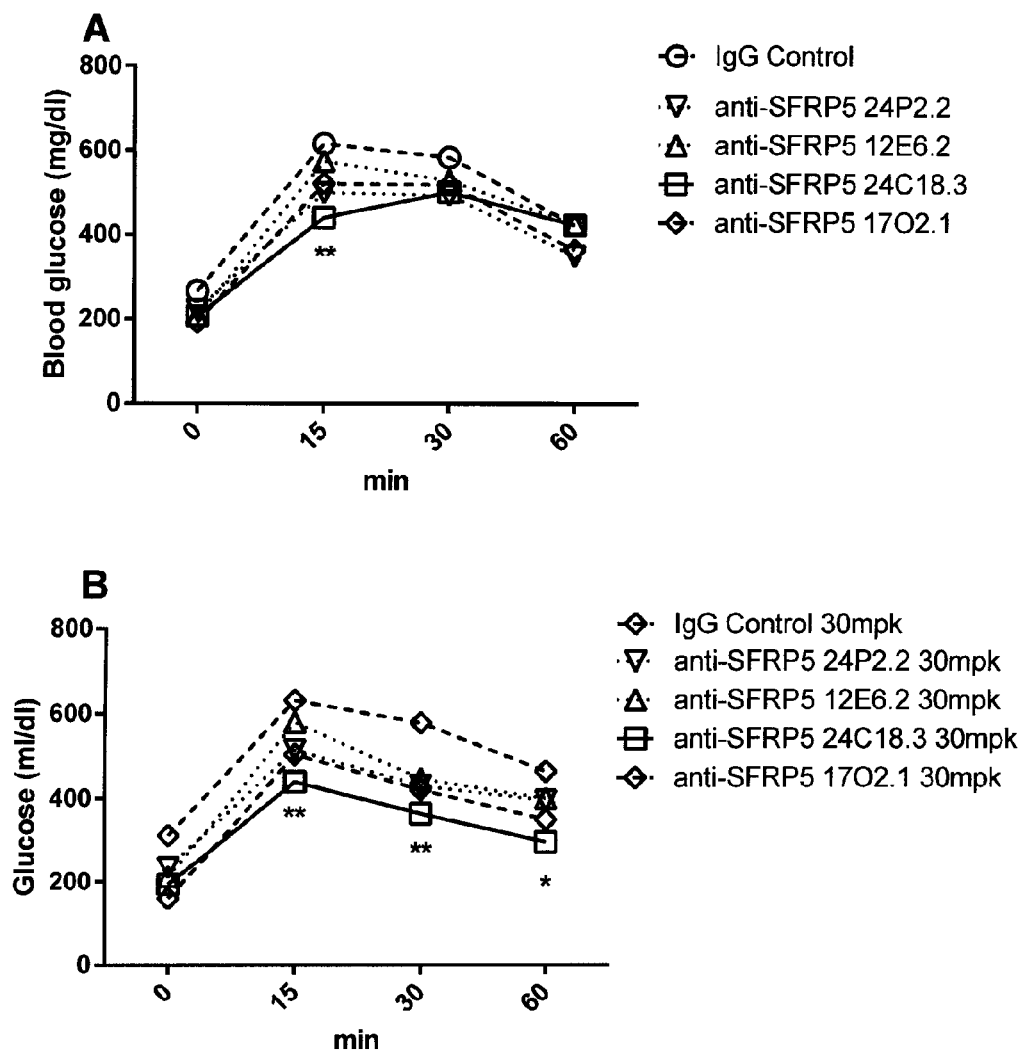
FIG. 4 is a series of two plots showing the results of glucose tolerance tests performed at week 2 (FIG. 4A) and week 4 (FIG. 4B) after injection into 6 week old B6.V-

Two oral glucose tolerance tests (OGTTs) were performed on 4 hr fasted mice at during the study. As shown in FIG. 4, the glucose tolerance of all groups of animals receiving an anti-SFRP5 antibody was better than that of the control group at both week 2 (FIG. 4A) and week 4 (FIG. 4B) of the study as demonstrated by glucose levels (mg/dL) and glucose AUC over the 60 minute period after p.o. glucose administration (1 g/kg). The glucose tolerance of the anti-SFRP5 subclone 24C18.3 group was better than the other groups at most time point, reaching statistical significance at 15 min in the GTT performed at week 2, and at the 15, 30 and 60 min in the GTT performed at week 4.

Glucose.

Fasting blood glucose levels were obtained at baseline, and at weeks 1, 2, 3 and 4 of the study. As shown in FIG. 5A, blood glucose levels at baseline for all five groups were comparable. The blood glucose levels of the control animals increased over the term of the study. At each time point, the animals receiving anti-SFRP5 antibodies had lower blood glucose levels compared to control. The difference reached statistical significance for the anti-SFRP5 subclone 24P2.2 group at week 1, for the anti-SFRP5 subclone 12E6.2 group at week 2, for the anti-SFRP5 subclone 24C18.3 group at weeks 3 and 4, and for the anti-SFRP5 subclone 17O2.1 group at weeks 2, 3 and 4.

Insulin.

Fasting insulin levels were obtained at baseline, and at weeks 1, 2, 3 and 4 of the study. As shown in FIG. 5B, insulin levels at baseline for all five groups were roughly comparable (with the insulin level of the anti-SFRP5 subclone 24P2.2 group being somewhat lower and the insulin level of the anti-SFRP5 subclone 24.C18.3 group being somewhat higher than the other groups). The insulin levels for all groups increased over the term of the study. Two anti-SFRP5 subclone groups (24C18.3 and 17O2.1) showed elevated serum insulin levels compared to other antibody-treated animals, suggesting possible differential epitope-dependent effects.

Body Weight.

Body weight for each group of animals was determined at baseline, and at weeks 1, 2, 3 and 4 of the study. As shown in FIG. 5C, body weight at baseline for all five groups was comparable. The body weight for all five groups increased over the term of the study but, overall, in this model, there appeared to be little impact on body weight.

Triglyceride.

Triglyceride levels for each group of animals were determined at baseline, and at weeks 1, 2, 3 and 4 of the study. As shown in FIG. 5D, triglyceride levels for the anti-SFRP5 subclone 24P2.2, 12E6.2, and 24C18.3 groups were markedly higher than for the anti-SFRP5 subclone 17O2.1 group and the control group at baseline. Over time, however, triglyceride levels decreased compared to control-treated mice, suggesting anti-SFRP5 antibody therapy may be beneficial for reducing serum triglyceride.

Fasting C-Peptide.

C-peptide levels for each group of animals were determined at week 4 of the study. As shown in FIG. 6, c-peptide levels for all of the anti-SFRP5 groups were higher than the control group, reaching statistical significance for the anti-SFRP5 subclone 24P2.2, 12E6.2, and 17O2.1 groups. Elevated serum c-peptide level may suggest that anti-SFRP5 antibody therapy could have a positive effect on pancreatic beta-cell function.

Conclusions.

These studies show that a binding protein that specifically bind to a SFRP5 can be leveraged for the treatment or amelioration of a metabolic disorder, such as type 2 diabetes, elevated glucose levels, elevated insulin levels, obesity or diabetic nephropathy, including by administering a therapeutically effective amount of an antagonist binding protein to a subject in need thereof. Note that further study confirmed that results with respect to the 17O2.1 clone were false positives.

Example 5

Sequences of Murine Anti-SFRP5 Antibodies

Monoclonal antibodies produced by the selected clones discussed above (e.g., mu24C18.3) were sequenced. The antibody was found to have an IgG2b heavy chain and a kappa light chain. The heavy chain variable regions ($V_H$) and the light chain variable regions ($V_L$) amino acid sequences of the murine antibody are provided in Table 9 (leader sequences in parentheses and CDR sequences underlined). The CDR sequences also are set forth in Tables 3A (CDRHs) and 3B (CDRLs), supra.

TABLE 9

Exemplary $V_H$ and $V_L$ Chains of Murine SFRP5 Antibodies

| Designation | SEQ ID NO: | Amino Acid Sequence |
|---|---|---|
| $V_H$_mu24C18.3 | 33 | (MGWSWIFFFLLSGTAGVHC)QVQLT QSGAELVRPGASVKLSCKASGYTFT<u>D YYINWVKQRPGQGLEWIAR</u>IYPGSGN TYYNEKFKGKATLTAEKSSSTAYMQL SSLTSEDSAVYFCAA<u>YSASAMDY</u>WGQ GTSVTVSS |
| $V_L$_mu24C18.3 | 34 | (METDTLLLWVLLLWVPGSTG)NVVL TQSPASLAVSLGQRATIS<u>CRASESVD SYGKSFMYW</u>YQQKPGQPPKLLIY<u>LAN NLES</u>GVPARFSGSGSRTDFTLTIDPV EADDAASYYC<u>QQNNEDPWT</u>FGGGTKL EIK |

The sequence information for specific muSFRP5 antibodies prepared and identified is summarized in Table 9, where the referenced antibody has the variable heavy ($V_H$) domain, variable light ($V_L$) domain, CDRH1, CDRH2, CDRH3, CDRL1, CDRL2 and CDRL3 sequences specified in the applicable row of the table.

TABLE 10

Exemplary mSFRP5 Antigen Binding Proteins

| Reference No. | Variable Heavy SEQ ID NO: | Variable Light SEQ ID NO: | CDRH1 SEQ ID NO: | CDRH2 SEQ ID NO: | CDRH3 SEQ ID NO: | CDRL1 SEQ ID NO: | CDRL2 SEQ ID NO: | CDRL3 SEQ ID NO: |
|---|---|---|---|---|---|---|---|---|
| mu24C18.3 | 33 | 34 | 23 | 24 | 25 | 26 | 27 | 28 |

Example 6

In Vivo Overexpression of SFRP5

The effects of SFRP5 overexpression in BDF-DIO BDF-lean mice were investigated. Glucose tolerance tests were performed at week 2 (FIG. 7A), week 4 (FIG. 7B) and week 6 (FIG. 7C) after AAV injection into 12 week old BDF-DIO males mice. Glucose levels (mg/dL) were measured over a 60 minute period after oral injection of glucose (2 g/kg) into 4 hour fasted AAV-SFRP5 mice (n=15) and AAV-empty vector mice (n=15). Metabolic parameters were measured over time, including body weight (FIG. 7D), fasting blood glucose (FIG. 7E), and fasting insulin (FIG. 7F). A glucose tolerance test was performed in BDF-lean mice 2 weeks after AAV injection (FIG. 7G). Glucose levels (mg/dL) were measured over a 60 minute period after oral injection of glucose (2 g/kg) into 4 hour fasted AAV-SFRP5 mice (n=11) and AAV-empty vector (control) mice (n=13). The area under the curve also was determined (FIG. 7H). AAV viral vectors were injected intravenously at $8\times10^{12}$ viral particles per mouse in saline (BDF-DIO mice) or at $1.6\times10^{12}$ viral particles per mouse in saline (BDF-lean mice). 2-way ANOVA statistical significance comparing AAV-SFRP5 mice to AAV-empty vector mice are indicated (asterisks) and the standard error of the mean is shown. BDF-DIO mice were fed a 60% high fat diet for at least 7 weeks prior AAV injections (FIG. 7).

The effects of SFRP5 over-expression in B6.V-Lep$^{ob}$/J male mice also were investigated. Glucose levels (mg/dL) over a 60 minute period after oral injection of glucose (1 g/kg) into 4 hour fasted AAV-SFRP5 mice (n=17) and AAV-empty vector mice (n=15), 2 weeks after AAV injection was determined (FIG. 8A). The area under the curve for the glucose tolerance test was determined (FIG. 8B). An insulin tolerance test was performed after 3 weeks post-AAV injection (FIG. 8C). Insulin (5 units/kg) was injected into mice fasted for 4 hours and blood glucose levels (mg/dL) were measured over a 60 minute period (FIG. 8(C). Metabolic parameters were measured over time, including body weight (FIG. 8D), fasting blood glucose (FIG. 8E), and fasting insulin (FIG. 8F). The serum insulin (FIG. 8G) and serum proinsulin (FIG. 8H) levels 2 weeks after AAV injection also were determined. AAV viral vectors were injected intravenously at $4\times10^{12}$ viral particles per mouse in saline. Mice were 6 weeks old at the time of AAV injection. 2-way ANOVA statistical significance (asterisks) comparing AAV-SFRP5 mice to AAV-empty vector mice (FIGS. 8A-F) and 2-tailed, unpaired t-test (asterisks) comparing AAV-SFRP5 mice to AAV-empty vector mice (FIGS. 8G-H). Standard error of the mean is shown.

The observed phenotypes from six independent studies performed in BDF-DIO, BDF-lean, and B6.V-Lep$^{ob}$/J male mice are summarized in Table 11. Phenotypes are those observed comparing AAV-SFRP5 injected mice to AAV-empty vector injected mice.

TABLE 11

Observed Phenotypes

| Observed Phenotypes with SFRP5 overexpression | Models |
|---|---|
| Significantly impaired glucose tolerance | BDF-DIO, BDF-lean & B6.V-Lep$^{ob}$/J |
| Significantly increased fasting glucose and insulin | BDF-DIO, BDF-lean & B6.V-Lep$^{ob}$/J |
| Elevated serum proinsulin | B6.V-Lep$^{ob}$/J |
| Decreased serum C-peptide | B6.V-Lep$^{ob}$/J |
| Indications of increased beta-cell apoptosis | B6.V-Lep$^{ob}$/J |
| Increased systemic triglyceride levels and reduced high density lipoprotein | BDF-DIO |
| Induced mild inflammation in liver, white adipose tissue and brown adipose tissue | B6.V-Lep$^{ob}$/J |
| No significant effect on body weight | BDF-DIO & B6.V-Lep$^{ob}$/J |
| No significant effect on lipid profile | B6.V-Lep$^{ob}$/J |

The characterization of the 6 anti-mouse SFRP5 antibody clones generated is summarized in Table 12. For each clone the identification (ID), equilibrium dissociation constant ($K_D$), K on ($k_{on}$ (1/Ms)), K off ($k_{off}$ (1/s)), and the epitope bin is provided. Binning based on SFRP5 binding and WNT3a competition data.

TABLE 12

Anti-SFRP5 Antibody Subclones

| Clone ID | IgG isotype | $K_D$ (M) | $k_{on}$ (1/Ms) | $k_{off}$ (1/s) | epitope bin |
|---|---|---|---|---|---|
| 12E6.1 | IgG2b | 5.55E−10 | 1.04E+05 | 5.78E−05 | 2 |
| 12E6.2 | IgG2b | 6.40E−10 | 1.12E+05 | 7.16E−05 | 2 |
| 24C18.2 | IgG2b | 5.64E−10 | 1.17E+05 | 6.60E−05 | 2 |
| 24C18.3 | IgG2b | 6.58E−10 | 1.12E+05 | 7.36E−05 | 2 |
| 24P2.1 | IgG2a | 7.53E−10 | 1.48E+05 | 1.11E−04 | 1 |
| 24P2.2 | IgG2a | 6.89E−10 | 1.74E+05 | 1.20E−04 | 1 |

Example 7

Inhibitory Effect of Anti-SFRP5 Monoclonal Antibody

The inhibitory effect of anti-SFRP5 monoclonal antibody on the inhibition of WNT3a-mediated signaling by SFRP5 recombinant protein was investigated using a 293/TCF luciferase cell assay. Relative luciferase units correlate with the addition of increasing recombinant human WNT3a added to 293/TCF cells (FIG. 9A). The addition of increasing amounts of recombinant SFRP5 added to WNT3a (180 ng/ml) inhibits WNT3a-mediated signaling (FIG. 9B). The addition of anti-SFRP5 (clone 24C18.3) to cells treated with both WNT3a (180 ng/ml) and recombinant SFRP5 (6 ug/ml) rescues the stimulatory effect of WNT3a on 293/TCF cells in a dose-dependent manner (FIG. 9C). Anti-SFRP5 monoclonal antibody clones, 24C18.3, 12E6.2 and 24P.2, were compared for their ability to inhibit SFRP5-mediated inhibition of WNT3a on 293 1TCF cells (FIG. 9D). Standard error of the mean is shown (FIG. 9). TCF/LEF Reporter (Luc)-HEK293 cell line from BPS Biosciences (San Diego, Calif.). Recombinant mouse WNT3a and SFRP5 from R&D Systems.

Example 8

In Vivo Pharmacokinetic Properties of Anti-SFRP5 Monoclonal Antibody

An in vivo study evaluating the pharmacokinetic properties of anti-SFRP5 monoclonal antibody clones 24C18.3, 12E6.2 and 24P2.2 was performed. B6.V-Lep$^{ob}$/J male mice (3 each for each time point) were injected intraperitoneally with one of the anti-SFRP5 monoclonal antibody clones. Blood was collected before injection (0) and 1, 3, 6, 24, 48, 72, 96 and 168 hours post injection. The concentration of monoclonal antibody in the blood at each time point is shown in FIG. 10. Concentrations were determined by ELISA using recombinant mouse SFRP5 to coat plates. Standard deviation is shown.

Example 9

Anti-SFRP5 Monoclonal Antibody Treatment

The effects of anti-SFRP5 monoclonal antibody treatment in B6.V-Lep$^{ob}$/J male mice was investigated. 6 week old B6.V-Lep$^{ob}$/J male mice were injected with an IgG control antibody or one of the 3 anti-SFRP5 monoclonal antibody clones; 24C18.3, 12E6.1 or 24P2.2. Glucose tolerance tests were performed at week 1 (FIG. 11A), week 2 (FIG. 11B) and week 4 (FIG. 11C). Each plot shows glucose levels (mg/dL) over a 60 minute period after oral injection of glucose (1 g/kg for week 1, 2 g/kg for weeks 2 and 4). Plots for body weight over time (FIG. 11D) and fasting blood glucose levels (FIG. 11E) are shown. The ratio of insulin to proinsulin (FIG. 11F) and C-peptide to proinsulin (FIG. 11G) present in the serum of 4 hour fasted mice upon harvest at week 5 were determined. Mice were treated with 30 mgs/kg of antibody, intraperitoneally, two-times per week over the course of the study. N=12 for each cohort. 2-way ANOVA statistical significance (asterisks) comparing mice treated with anti-SFRP5 monoclonal antibody to IgG control mice (FIG. 11). Standard error of the mean is shown.

Example 10

Anti-SFRP5 Monoclonal Antibody Treatment—Clone, 24C18.3

The effect of anti-SFRP5 monoclonal antibody clone, 24C18.3, on C57BL/6J male mice was investigated. 20 week old C57BL/6J male mice fed a 60% high fat diet for at least 8 weeks were injected with an IgG control antibody (30 mgs/kg) or anti-SFRP5 monoclonal antibody clone, 24C18.3 (30 mgs/kg or 3 mgs/kg). A glucose tolerance test was performed at week 2 on 4 hour fasted mice (FIG. 12A). The plot shows glucose levels (mg/dL) over a 60 minute period after oral injection of glucose (2 g/kg). The first bar graphs (FIG. 12B) shows the ratio of C-peptide to proinsulin in the serum of IgG-treated mice (30 mgs/kg) compared to 24C18.3-treated mice (30 mgs/kg). The second bar graphs (FIG. 12C) shows the ratio of C-peptide to proinsulin content in the pancreas of IgG-treated mice (30 mgs/kg) compared to 24C18.3-treated mice (30 mgs/kg). Hormone content was normalized to total protein content. Mice were treated with 30 mgs/kg or 3 mgs/kg (as indicated) of antibody, intraperitoneally, two-times per week over the course of the study. N=12 for each cohort. 2-way ANOVA statistical significance (asterisks) comparing mice treated with anti-SFRP5 monoclonal antibody to IgG control mice (FIG. 12). Standard error of the mean is shown.

All patents and other publications identified are expressly incorporated herein by reference for the purpose of describing and disclosing, for example, the methodologies described in such publications that might be used in connection with the described. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. An antigen binding protein that specifically binds SFRP5 (secreted frizzled-related protein5) and comprises:
   i. a CDRH1 of SEQ ID NO:23;
   ii. a CDRH2 of SEQ ID NO:24;
   iii. a CDRH3 of SEQ ID NO:25;
   i. a CDRL1 of SEQ ID NO:26;
   ii. a CDRL2 of SEQ ID NO:27; and
   iii. a CDRL3 of SEQ ID NO:28.

2. The antigen binding protein according to claim 1, wherein the antigen binding protein comprises a heavy chain variable region ($V_H$) and/or a light chain variable region ($V_L$), wherein
   a. the $V_H$ has at least 90% sequence identity with the amino acid sequence selected from the group consisting of SEQ ID NO: 19 and 20; and
   b. the $V_L$ has at least 90% sequence identity with the amino acid sequence selected from the group consisting of SEQ ID NO:21 and 22.

3. The antigen binding protein according to claim 2, wherein the antigen binding protein comprises a heavy chain variable region ($V_H$) and a light chain variable region ($V_L$), wherein
   a. the $V_H$ comprises the amino acid sequence of SEQ ID NO: 19 and the $V_L$ comprises the amino acid sequence of SEQ ID NO:21;
   b. the $V_H$ comprises the amino acid sequence of SEQ ID NO:20 and the $V_L$ comprises the amino acid sequence of SEQ ID NO:21;
   c. the $V_H$ comprises the amino acid sequence of SEQ ID NO: 19 and the $V_L$ comprises the amino acid sequence of SEQ ID NO:22; or
   d. the $V_H$ comprises the amino acid sequence of SEQ ID NO:20 and the $V_L$ comprises the amino acid sequence of SEQ ID NO:22.

4. The antigen binding protein according to claim 2, wherein the antigen binding protein comprises a heavy chain (HC) and/or a light chain (LC), wherein
   a. the HC has at least 90% sequence identity with the amino acid sequence selected from the group consisting of SEQ ID NO:15 and 16; and
   b. the LC has at least 90% sequence identity with the amino acid sequence selected from the group consisting of SEQ ID NO:17 and 18.

5. The antigen binding protein according to claim 4, wherein the antigen binding protein comprises a heavy chain (HC) and a light chain (LC), wherein
   a. the HC comprises the amino acid sequence of SEQ ID NO: 15 and the LC comprises the amino acid sequence of SEQ ID NO: 17;
   b. the HC comprises the amino acid sequence of SEQ ID NO: 16 and the LC comprises the amino acid sequence of SEQ ID NO: 17;

c. the HC comprises the amino acid sequence of SEQ ID NO: 15 and the LC comprises the amino acid sequence of SEQ ID NO: 18; or
d. the HC comprises the amino acid sequence of SEQ ID NO: 16 and the LC comprises the amino acid sequence of SEQ ID NO: 18.

6. A pharmaceutical composition comprising at least one antigen binding protein according to claim 1, and a pharmaceutically acceptable diluent, carrier, solubilizer, emulsifier, preservative, or adjuvant.

7. A nucleic acid molecule encoding the antigen binding protein of claim 1.

8. An isolated host cell comprising the nucleic acid of claim 7.

9. A vector comprising the nucleic acid of claim 7.

10. An isolated host cell comprising the vector of claim 9.

11. A method of making an antigen binding protein comprising culturing a host cell of claim 8 or 10 under conditions suitable for synthesizing the antigen binding protein and purifying the antigen binding protein from the host cell.

* * * * *

SEQUENCE LISTING

<160> NUMBER OF SEQ ID NOS: 34

<210> SEQ ID NO 1
<211> LENGTH: 317
<212> TYPE: PRT
<213> ORGANISM: Homo sapiens

<400> SEQUENCE: 1

Met Arg Ala Ala Ala Gly Gly Val Arg Thr Ala Ala Leu Ala
1               5                   10                  15

Leu Leu Leu Gly Ala Leu His Trp Ala Pro Ala Arg Cys Glu Glu Tyr
            20                  25                  30

Asp Tyr Tyr Gly Trp Gln Ala Glu Pro Leu His Gly Arg Ser Tyr Ser
        35                  40                  45

Lys Pro Pro Gln Cys Leu Asp Ile Pro Ala Asp Leu Pro Leu Cys His
    50                  55                  60

Thr Val Gly Tyr Lys Arg Met Arg Leu Pro Asn Leu Leu Glu His Glu
65                  70                  75                  80

Ser Leu Ala Glu Val Lys Gln Gln Ala Ser Ser Trp Leu Pro Leu Leu
                85                  90                  95

Ala Lys Arg Cys His Ser Asp Thr Gln Val Phe Leu Cys Ser Leu Phe
            100                 105                 110

Ala Pro Val Cys Leu Asp Arg Pro Ile Tyr Pro Cys Arg Ser Leu Cys
            115                 120                 125

Glu Ala Val Arg Ala Gly Cys Ala Pro Leu Met Glu Ala Tyr Gly Phe
        130                 135                 140

Pro Trp Pro Glu Met Leu His Cys His Lys Phe Pro Leu Asp Asn Asp
145                 150                 155                 160

Leu Cys Ile Ala Val Gln Phe Gly His Leu Pro Ala Thr Ala Pro Pro
                165                 170                 175

Val Thr Lys Ile Cys Ala Gln Cys Glu Met Glu His Ser Ala Asp Gly
            180                 185                 190

Leu Met Glu Gln Met Cys Ser Ser Asp Phe Val Val Lys Met Arg Ile
        195                 200                 205

Lys Glu Ile Lys Ile Glu Asn Gly Asp Arg Lys Leu Ile Gly Ala Gln
    210                 215                 220

Lys Lys Lys Lys Leu Leu Lys Pro Gly Pro Leu Lys Arg Lys Asp Thr
225                 230                 235                 240

Lys Arg Leu Val Leu His Met Lys Asn Gly Ala Gly Cys Pro Cys Pro
                245                 250                 255

Gln Leu Asp Ser Leu Ala Gly Ser Phe Leu Val Met Gly Arg Lys Val
            260                 265                 270

Asp Gly Gln Leu Leu Leu Met Ala Val Tyr Arg Trp Asp Lys Lys Asn
        275                 280                 285

Lys Glu Met Lys Phe Ala Val Lys Phe Met Phe Ser Tyr Pro Cys Ser
    290                 295                 300

Leu Tyr Tyr Pro Phe Phe Tyr Gly Ala Ala Glu Pro His
305                 310                 315

<210> SEQ ID NO 2
<211> LENGTH: 954
<212> TYPE: DNA
<213> ORGANISM: Homo sapiens

<400> SEQUENCE: 2
atgcgcgcgg cggcggcggg cggcggcgtg cgcaccgcgg cgctggcgct gctgctgggc    60

-continued

```
gcgctgcatt gggcgccggc gcgctgcgaa gaatatgatt attatggctg gcaggcggaa      120
ccgctgcatg gccgcagcta tagcaaaccg ccgcagtgcc tggatattcc ggcggatctg      180
ccgctgtgcc ataccgtggg ctataaacgc atgcgcctgc cgaacctgct ggaacatgaa      240
agcctggcgg aagtgaaaca gcaggcgagc agctggctgc cgctgctggc gaaacgctgc      300
catagcgata cccaggtgtt tctgtgcagc ctgtttgcgc cggtgtgcct ggatcgcccg      360
atttatccgt gccgcagcct gtgcgaagcg gtgcgcgcgg gctgcgcgcc gctgatggaa      420
gcgtatggct ttccgtggcc ggaaatgctg cattgccata aatttccgct ggataacgat      480
ctgtgcattg cggtgcagtt tggccatctg ccggcgaccg cgccgccggt gaccaaaatt      540
tgcgcgcagt gcgaaatgga acatagcgcg gatggcctga tggaacagat gtgcagcagc      600
gattttgtgg tgaaaatgcg cattaaagaa attaaaattg aaacggcga tcgcaaactg      660 attggcgcgc agaaaaaaaa aaaactgctg aaaccgggcc cgctgaaacg caaagatacc      720
aaacgcctgg tgctgcatat gaaaaacggc gcgggctgcc cgtgcccgca gctggatagc      780
ctggcgggca gctttctggt gatgggccgc aaagtggatg ccagctgct gctgatggcg      840 gtgtatcgct gggataaaaa aaacaaagaa atgaaatttg cggtgaaatt tatgtttagc      900
tatccgtgca gcctgtatta ccgttttttt tatggcgcgg cggaaccgca ttaa            954
```

```
<210> SEQ ID NO 3
<211> LENGTH: 288
<212> TYPE: PRT
<213> ORGANISM: Homo sapiens

<400> SEQUENCE: 3
```

```
Glu Glu Tyr Asp Tyr Tyr Gly Trp Gln Ala Glu Pro Leu His Gly Arg
1               5                   10                  15

Ser Tyr Ser Lys Pro Pro Gln Cys Leu Asp Ile Pro Ala Asp Leu Pro
            20                  25                  30

Leu Cys His Thr Val Gly Tyr Lys Arg Met Arg Leu Pro Asn Leu Leu
        35                  40                  45

Glu His Glu Ser Leu Ala Glu Val Lys Gln Gln Ala Ser Ser Trp Leu
    50                  55                  60

Pro Leu Leu Ala Lys Arg Cys His Ser Asp Thr Gln Val Phe Leu Cys
65                  70                  75                  80

Ser Leu Phe Ala Pro Val Cys Leu Asp Arg Pro Ile Tyr Pro Cys Arg
                85                  90                  95

Ser Leu Cys Glu Ala Val Arg Ala Gly Cys Ala Pro Leu Met Glu Ala
            100                 105                 110

Tyr Gly Phe Pro Trp Pro Glu Met Leu His Cys His Lys Phe Pro Leu
        115                 120                 125

Asp Asn Asp Leu Cys Ile Ala Val Gln Phe Gly His Leu Pro Ala Thr
    130                 135                 140

Ala Pro Pro Val Thr Lys Ile Cys Ala Gln Cys Glu Met Glu His Ser
145                 150                 155                 160

Ala Asp Gly Leu Met Glu Gln Met Cys Ser Ser Asp Phe Val Val Lys
                165                 170                 175

Met Arg Ile Lys Glu Ile Lys Ile Glu Asn Gly Asp Arg Lys Leu Ile
            180                 185                 190

Gly Ala Gln Lys Lys Lys Lys Leu Leu Lys Pro Gly Pro Leu Lys Arg
        195                 200                 205

Lys Asp Thr Lys Arg Leu Val Leu His Met Lys Asn Gly Ala Gly Cys
```

Pro Cys Pro Gln Leu Asp Ser Leu Ala Gly Ser Phe Leu Val Met Gly
225                 230                 235                 240

Arg Lys Val Asp Gly Gln Leu Leu Met Ala Val Tyr Arg Trp Asp
            245                 250                 255

Lys Lys Asn Lys Glu Met Lys Phe Ala Val Lys Phe Met Phe Ser Tyr
                260                 265                 270

Pro Cys Ser Leu Tyr Tyr Pro Phe Phe Tyr Gly Ala Ala Glu Pro His
            275                 280                 285

<210> SEQ ID NO 4
<211> LENGTH: 867
<212> TYPE: DNA
<213> ORGANISM: Homo sapiens

<400> SEQUENCE: 4
gaagaatatg attattatgg ctggcaggcg aaccgctgc atggccgcag ctatagcaaa      60
ccgccgcagt gcctggatat tccggcggat ctgccgctgt gccataccgt gggctataaa    120
cgcatgcgcc tgccgaacct gctggaacat gaaagcctgg cggaagtgaa acagcaggcg    180
agcagctggc tgccgctgct ggcgaaacgc tgccatagcg ataccaggt gtttctgtgc     240 agcctgtttg cgccggtgtg cctggatcgc ccgatttatc cgtgccgcag cctgtgcgaa    300
gcggtgcgcg cgggctgcgc gccgctgatg gaagcgtatg ctttccgtg gccggaaatg    360 ctgcattgcc ataaatttcc gctggataac gatctgtgca ttgcggtgca gtttggccat    420
ctgccggcga ccgcgccgcc ggtgaccaaa atttgcgcgc agtgcgaaat ggaacatagc    480
gcggatggcc tgatggaaca gatgtgcagc agcgattttg tggtgaaaat gcgcattaaa    540
gaaattaaaa ttgaaaacgg cgatcgcaaa ctgattggcg cgcagaaaaa aaaaaactg    600 ctgaaaccgg gcccgctgaa acgcaaagat accaaacgcc tggtgctgca tatgaaaaac    660
ggcgcgggct gcccgtgccc gcagctggat agcctggcgg gcagctttct ggtgatgggc    720
cgcaaagtgg atggccagct gctgctgatg gcggtgtatc gctgggataa aaaaaacaaa    780
gaaatgaaat ttgcggtgaa atttatgttt agctatccgt gcagcctgta ttatccgttt    840
ttttatggcg cggcggaacc gcattaa                                         867

<210> SEQ ID NO 5
<211> LENGTH: 314
<212> TYPE: PRT
<213> ORGANISM: Mus musculus

<400> SEQUENCE: 5

Met Trp Val Ala Trp Ser Ala Arg Thr Ala Ala Leu Ala Leu Leu Leu
1               5                   10                  15

Gly Ala Leu His Gly Ala Pro Thr Arg Gly Gln Glu Tyr Asp Tyr Tyr
            20                  25                  30

Gly Trp Gln Ala Glu Pro Leu His Gly Arg Ser Tyr Ser Lys Pro Pro
        35                  40                  45

Gln Cys Leu Asp Ile Pro Ala Asp Leu Pro Leu Cys His Thr Val Gly
    50                  55                  60

Tyr Lys Arg Met Arg Leu Pro Asn Leu Leu Glu His Glu Ser Leu Ala
65                  70                  75                  80

Glu Val Lys Gln Gln Ala Ser Ser Trp Leu Pro Leu Leu Ala Lys Arg
                85                  90                  95

Cys His Ser Asp Thr Gln Val Phe Leu Cys Ser Leu Phe Ala Pro Val

```
                    100                 105                 110
Cys Leu Asp Arg Pro Ile Tyr Pro Cys Arg Ser Leu Cys Glu Ala Val
            115                 120                 125
Arg Ala Gly Cys Ala Pro Leu Met Glu Ala Tyr Gly Phe Pro Trp Pro
        130                 135                 140
Glu Met Leu His Cys His Lys Phe Pro Leu Asp Asn Asp Leu Cys Ile
145                 150                 155                 160
Ala Val Gln Phe Gly His Leu Pro Ala Thr Ala Pro Pro Val Thr Lys
                165                 170                 175
Ile Cys Ala Gln Cys Glu Met Glu His Ser Ala Asp Gly Leu Met Glu
            180                 185                 190
Gln Met Cys Ser Ser Asp Phe Val Val Lys Met Arg Ile Lys Glu Ile
        195                 200                 205
Lys Ile Asp Asn Gly Asp Arg Lys Leu Ile Gly Ala Gln Lys Lys Lys
    210                 215                 220
Lys Leu Leu Lys Ala Gly Pro Leu Lys Arg Lys Asp Thr Lys Lys Leu
225                 230                 235                 240
Val Leu His Met Lys Asn Gly Ala Ser Cys Pro Cys Pro Gln Leu Asp
                245                 250                 255
Asn Leu Thr Gly Ser Phe Leu Val Met Gly Arg Lys Val Glu Gly Gln
            260                 265                 270
Leu Leu Leu Thr Ala Val Tyr Arg Trp Asp Lys Lys Asn Lys Glu Met
        275                 280                 285
Lys Phe Ala Val Lys Phe Met Phe Ser Tyr Pro Cys Ser Leu Tyr Tyr
    290                 295                 300
Pro Phe Phe Tyr Gly Ala Ala Glu Pro His
305                 310
```

<210> SEQ ID NO 6
<211> LENGTH: 945
<212> TYPE: DNA
<213> ORGANISM: Mus musculus

<400> SEQUENCE: 6

```
atgtgggtgg cgtggagcgc gcgcaccgcg gcgctggcgc tgctgctggg cgcgctgcat      60
ggcgcgccga cccgcggcca ggaatatgat tattatggct ggcaggcgga accgctgcat     120
ggccgcagct atagcaaacc gccgcagtgc ctggatattc cggcggatct gccgctgtgc     180
cataccgtgg gctataaacg catgcgcctg ccgaacctgc tggaacatga agcctggcg      240
gaagtgaaac agcaggcgag cagctggctg ccgctgctgg cgaaacgctg ccatagcgat     300
acccaggtgt ttctgtgcag cctgtttgcg ccggtgtgcc tggatcgccc gatttatccg     360
tgccgcagcc tgtgcgaagc ggtgcgcgcg ggctgcgcgc cgctgatgga agcgtatggc     420
tttccgtggc cggaaatgct gcattgccat aaatttccgc tggataacga tctgtgcatt     480
gcggtgcagt ttggccatct gccggcgacc gcgccgccgg tgaccaaaat ttgcgcgcag     540
tgcgaaatgg aacatagcgc ggatggcctg atggaacaga tgtgcagcag cgattttgtg     600
gtgaaaatgc gcattaaaga aattaaaatt gataacggcg atcgcaaact gattggcgcg     660
cagaaaaaaa aaaaactgct gaaagcgggc ccgctgaaac gcaaagatac caaaaaactg     720
gtgctgcata tgaaaaacgg cgcgagctgc ccgtgcccgc agctggataa cctgaccggc     780
agctttctgg tgatgggccg caaagtggaa ggcagctgc tgctgaccgc ggtgtatcgc     840
tgggataaaa aaaacaaaga aatgaaattt gcggtgaaat ttatgtttag ctatccgtgc     900
```
agcctgtatt atccgttttt ttatggcgcg gcggaaccgc attaa     945

<210> SEQ ID NO 7
<211> LENGTH: 293
<212> TYPE: PRT
<213> ORGANISM: Mus musculus

<400> SEQUENCE: 7

```
Ala Pro Thr Arg Gly Gln Glu Tyr Asp Tyr Tyr Gly Trp Gln Ala Glu
1               5                   10                  15

Pro Leu His Gly Arg Ser Tyr Ser Lys Pro Pro Gln Cys Leu Asp Ile
            20                  25                  30

Pro Ala Asp Leu Pro Leu Cys His Thr Val Gly Tyr Lys Arg Met Arg
        35                  40                  45

Leu Pro Asn Leu Leu Glu His Glu Ser Leu Ala Glu Val Lys Gln Gln
    50                  55                  60

Ala Ser Ser Trp Leu Pro Leu Leu Ala Lys Arg Cys His Ser Asp Thr
65                  70                  75                  80

Gln Val Phe Leu Cys Ser Leu Phe Ala Pro Val Cys Leu Asp Arg Pro
                85                  90                  95

Ile Tyr Pro Cys Arg Ser Leu Cys Glu Ala Val Arg Ala Gly Cys Ala
            100                 105                 110

Pro Leu Met Glu Ala Tyr Gly Phe Pro Trp Pro Glu Met Leu His Cys
        115                 120                 125

His Lys Phe Pro Leu Asp Asn Asp Leu Cys Ile Ala Val Gln Phe Gly
    130                 135                 140

His Leu Pro Ala Thr Ala Pro Pro Val Thr Lys Ile Cys Ala Gln Cys
145                 150                 155                 160

Glu Met Glu His Ser Ala Asp Gly Leu Met Glu Gln Met Cys Ser Ser
                165                 170                 175

Asp Phe Val Val Lys Met Arg Ile Lys Glu Ile Lys Ile Asp Asn Gly
            180                 185                 190

Asp Arg Lys Leu Ile Gly Ala Gln Lys Lys Lys Leu Leu Lys Ala
        195                 200                 205

Gly Pro Leu Lys Arg Lys Asp Thr Lys Lys Leu Val Leu His Met Lys
    210                 215                 220

Asn Gly Ala Ser Cys Pro Cys Pro Gln Leu Asp Asn Leu Thr Gly Ser
225                 230                 235                 240

Phe Leu Val Met Gly Arg Lys Val Glu Gly Gln Leu Leu Leu Thr Ala
                245                 250                 255

Val Tyr Arg Trp Asp Lys Lys Asn Lys Glu Met Lys Phe Ala Val Lys
            260                 265                 270

Phe Met Phe Ser Tyr Pro Cys Ser Leu Tyr Tyr Pro Phe Phe Tyr Gly
        275                 280                 285

Ala Ala Glu Pro His
    290
```

<210> SEQ ID NO 8
<211> LENGTH: 882
<212> TYPE: DNA
<213> ORGANISM: Mus musculus

<400> SEQUENCE: 8
gcgccgaccc gcggccagga atatgattat tatggctggc aggcggaacc gctgcatggc     60
cgcagctata gcaaaccgcc gcagtgcctg gatattccgg cggatctgcc gctgtgccat    120

```
accgtgggct ataaacgcat gcgcctgccg aacctgctgg aacatgaaag cctggcggaa    180
gtgaaacagc aggcgagcag ctggctgccg ctgctggcga aacgctgcca tagcgatacc    240
caggtgtttc tgtgcagcct gtttgcgccg gtgtgcctgg atcgcccgat ttatccgtgc    300
cgcagcctgt gcgaagcggt gcgcgcgggc tgcgcgccgc tgatggaagc gtatggcttt    360
ccgtggccgg aaatgctgca ttgccataaa tttccgctgg ataacgatct gtgcattgcg    420
gtgcagtttg ccatctgcc ggcgaccgcg ccgccggtga ccaaaatttg cgcgcagtgc     480
gaaatggaac atagcgcgga tggcctgatg aacagatgt gcagcagcga ttttgtggtg     540
aaaatgcgca ttaaagaaat taaaattgat aacggcgatc gcaaactgat tggcgcgcag    600
aaaaaaaaaa aactgctgaa agcgggcccg ctgaaacgca agataccaa aaaactggtg     660 ctgcatatga aaacggcgc gagctgcccg tgcccgcagc tggataacct gaccggcagc     720
tttctggtga tgggccgcaa agtggaaggc cagctgctgc tgaccgcggt gtatcgctgg    780
gataaaaaaa acaaagaaat gaaatttgcg gtgaaattta tgtttagcta tccgtgcagc    840
ctgtattatc cgttttttta tggcgcggcg aaccgcatt aa                        882
```

```
<210> SEQ ID NO 9
<211> LENGTH: 326
<212> TYPE: PRT
<213> ORGANISM: Artificial Sequence
<220> FEATURE:
<223> OTHER INFORMATION: IgG2 heavy chain constant domain of an
      exemplary SFRP5 monoclonal antibody

<400> SEQUENCE: 9
```

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

```
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 10
<211> LENGTH: 105
<212> TYPE: PRT
<213> ORGANISM: Artificial Sequence
<220> FEATURE:
<223> OTHER INFORMATION: lambda light chain constant domain of an
      exemplary SFRP5 monoclonoal antibody

<400> SEQUENCE: 10

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
        50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 11
<211> LENGTH: 106
<212> TYPE: PRT
<213> ORGANISM: Artificial Sequence
<220> FEATURE:
<223> OTHER INFORMATION: kappa light chain constant domain of an
      exemplary SFRP5 monoclonal antibody

<400> SEQUENCE: 11

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80
```

His Lys Val Tyr Ala Cys Glu Val Thr His Gln Gly Leu Ser Ser Pro
            85                  90                  95

Val Thr Lys Ser Phe Asn Arg Gly Glu Cys
            100                 105

<210> SEQ ID NO 12
<211> LENGTH: 981
<212> TYPE: DNA
<213> ORGANISM: Artificial Sequence
<220> FEATURE:
<223> OTHER INFORMATION: IgG2 heavy chain constant region

<400> SEQUENCE: 12

```
gctagcacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggacccctga ggtcacgtgc     420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt tgtgcaccag gactggctga acggcaagga gtacaagtgc     600
aaggtctcca acaaaggcct cccagccccc atcgagaaaa ccatctccaa aaccaaaggg     660
cagccccgag aaccacaggt gtacaccctg cccccatccc gggaggagat gaccaagaac     720
caggtcagcc tgacctgcct ggtcaaaggc ttctacccca gcgacatcgc cgtggagtgg     780
gagagcaatg ggcagccgga gaacaactac aagaccacac ctcccatgct ggactccgac     840
ggctccttct tcctctacag caagctcacc gtggacaaga gcaggtggca gcaggggaac     900
gtcttctcat gctccgtgat gcatgaggct ctgcacaacc actacacgca gaagagcctc     960
tccctgtctc cgggtaaatg a                                               981
```

<210> SEQ ID NO 13
<211> LENGTH: 318
<212> TYPE: DNA
<213> ORGANISM: Artificial Sequence
<220> FEATURE:
<223> OTHER INFORMATION: IgG2 lambda light chain constant region

<400> SEQUENCE: 13

```
ggtcagccca aggctgcccc ctcggtcact ctgttcccgc cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca acaagtacgc ggccagcagc tatctgagcc tgacgcctga gcagtggaag     240
tcccacagaa gctacagctg ccaggtcacg catgaaggga gcaccgtgga agacagtg      300
gcccctacag aatgttca                                                   318
```

<210> SEQ ID NO 14
<211> LENGTH: 324
<212> TYPE: DNA
<213> ORGANISM: Artificial Sequence
<220> FEATURE:
<223> OTHER INFORMATION: IgG2 kappa light chain constant region

<400> SEQUENCE: 14

```
cgtacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg ttag                                         324
```

<210> SEQ ID NO 15
<211> LENGTH: 443
<212> TYPE: PRT
<213> ORGANISM: Artificial Sequence
<220> FEATURE:
<223> OTHER INFORMATION: Exemplary Heavy Chain

<400> SEQUENCE: 15

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Tyr
             20                  25                  30

Tyr Ile Asn Trp Val Arg Gln Ala Thr Gly Gln Gly Leu Glu Trp Met
         35                  40                  45

Gly Arg Ile Tyr Pro Gly Ser Gly Asn Thr Tyr Tyr Asn Glu Lys Phe
     50                  55                  60

Lys Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Ser Ala Ser Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285
```

```
Glu Glu Gln Phe Asn Ser Thr Phe Arg Val Val Ser Val Leu Thr Val
290                 295                 300
Val His Gln Asp Trp Leu Asn Gly Lys Glu Tyr Lys Cys Lys Val Ser
305                 310                 315                 320
Asn Lys Gly Leu Pro Ala Pro Ile Glu Lys Thr Ile Ser Lys Thr Lys
                325                 330                 335
Gly Gln Pro Arg Glu Pro Gln Val Tyr Thr Leu Pro Pro Ser Arg Glu
                340                 345                 350
Glu Met Thr Lys Asn Gln Val Ser Leu Thr Cys Leu Val Lys Gly Phe
            355                 360                 365
Tyr Pro Ser Asp Ile Ala Val Glu Trp Glu Ser Asn Gly Gln Pro Glu
370                 375                 380
Asn Asn Tyr Lys Thr Thr Pro Pro Met Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
                420                 425                 430
Thr Gln Lys Ser Leu Ser Leu Ser Pro Gly Lys
            435                 440

<210> SEQ ID NO 16
<211> LENGTH: 443
<212> TYPE: PRT
<213> ORGANISM: Artificial Sequence
<220> FEATURE:
<223> OTHER INFORMATION: Exemplary Heavy Chain

<400> SEQUENCE: 16

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Tyr Ile Asn Trp Val Arg Gln Ala Thr Gly Gln Gly Leu Glu Trp Met
        35                  40                  45
Gly Arg Ile Tyr Pro Gly Ser Gly Asn Thr Tyr Tyr Asn Glu Lys Phe
    50                  55                  60
Lys Gly Arg Val Thr Leu Thr Ala Glu Lys Ser Ser Ser Thr Ala Tyr
65                  70                  75                  80
Met Glu Leu Ser Ser Leu Arg Ser Glu Asp Thr Ala Val Tyr Phe Cys
                85                  90                  95
Ala Ala Tyr Ser Ala Ser Ala Met Asp Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Cys Ser Arg Ser Thr Ser Glu Ser Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Asn
            180                 185                 190
Phe Gly Thr Gln Thr Tyr Thr Cys Asn Val Asp His Lys Pro Ser Asn
        195                 200                 205
```

Thr Lys Val Asp Lys Thr Val Glu Arg Lys Cys Cys Val Glu Cys Pro
        210                 215                 220

Pro Cys Pro Ala Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
                260                 265                 270

Trp Tyr Val Asp Gly Val Glu Val His Asn Ala Lys Thr Lys Pro Arg
                275                 280                 285

Glu Glu Gln Phe Asn Ser Thr Phe Arg Val Val Ser Val Leu Thr Val
            290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 17
<211> LENGTH: 218
<212> TYPE: PRT
<213> ORGANISM: Artificial Sequence
<220> FEATURE:
<223> OTHER INFORMATION: Exemplary Light Chain

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Ser Tyr
                20                  25                  30

Gly Lys Ser Phe Met Tyr Trp Tyr Gln Gln Lys Pro Gly Gln Pro Pro
            35                  40                  45

Lys Leu Leu Ile Tyr Leu Ala Asn Asn Leu Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

```
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
    210                 215

<210> SEQ ID NO 18
<211> LENGTH: 218
<212> TYPE: PRT
<213> ORGANISM: Artificial Sequence
<220> FEATURE:
<223> OTHER INFORMATION: Exemplary Light Chain

<400> SEQUENCE: 18

Asp Val Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Ser Tyr
                20                  25                  30

Gly Lys Ser Phe Met Tyr Trp Tyr Gln Gln Lys Pro Gly Gln Pro Pro
            35                  40                  45

Lys Leu Leu Ile Tyr Leu Ala Asn Asn Leu Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
    210                 215

<210> SEQ ID NO 19
<211> LENGTH: 117
<212> TYPE: PRT
<213> ORGANISM: Artificial Sequence
<220> FEATURE:
<223> OTHER INFORMATION: Exemplary heavy chain variable region

<400> SEQUENCE: 19
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Thr Gly Gln Gly Leu Glu Trp Met
        35                  40                  45

Gly Arg Ile Tyr Pro Gly Ser Gly Asn Thr Tyr Tyr Asn Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Ser Ala Ser Ala Met Asp Tyr Trp Gly Gln Gly Thr Leu
            100                 105                 110

Val Thr Val Ser Ser
        115

<210> SEQ ID NO 20
<211> LENGTH: 117
<212> TYPE: PRT
<213> ORGANISM: Artificial Sequence
<220> FEATURE:
<223> OTHER INFORMATION: Exemplary heavy chain variable region

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Thr Gly Gln Gly Leu Glu Trp Met
        35                  40                  45

Gly Arg Ile Tyr Pro Gly Ser Gly Asn Thr Tyr Tyr Asn Glu Lys Phe
    50                  55                  60

Lys Gly Arg Val Thr Leu Thr Ala Glu Lys Ser Ser Thr Thr Ala Tyr
65                  70                  75                  80

Met Glu Leu Ser Ser Leu Arg Ser Glu Asp Thr Ala Val Tyr Phe Cys
                85                  90                  95

Ala Ala Tyr Ser Ala Ser Ala Met Asp Tyr Trp Gly Gln Gly Thr Leu
            100                 105                 110

Val Thr Val Ser Ser
        115

<210> SEQ ID NO 21
<211> LENGTH: 112
<212> TYPE: PRT
<213> ORGANISM: Artificial Sequence
<220> FEATURE:
<223> OTHER INFORMATION: Exemplary light chain variable region

<400> SEQUENCE: 21

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Ser Tyr
            20                  25                  30

Gly Lys Ser Phe Met Tyr Trp Tyr Gln Gln Lys Pro Gly Gln Pro Pro
        35                  40                  45

Lys Leu Leu Ile Tyr Leu Ala Asn Asn Leu Glu Ser Gly Val Pro Asp
```

```
                   50                  55                  60
Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Asn Asn
                 85                  90                  95

Glu Asp Pro Trp Thr Phe Gly Gly Gly Thr Lys Val Glu Ile Lys Arg
                100                 105                 110
```

<210> SEQ ID NO 22
<211> LENGTH: 112
<212> TYPE: PRT
<213> ORGANISM: Artificial Sequence
<220> FEATURE:
<223> OTHER INFORMATION: Exemplary light chain variable region

<400> SEQUENCE: 22

```
Asp Val Val Leu Thr Gln Ser Pro Asp Ser Leu Ala Val Ser Leu Gly
 1               5                  10                  15

Glu Arg Ala Thr Ile Asn Cys Arg Ala Ser Glu Ser Val Asp Ser Tyr
                 20                  25                  30

Gly Lys Ser Phe Met Tyr Trp Tyr Gln Gln Lys Pro Gly Gln Pro Pro
             35                  40                  45

Lys Leu Leu Ile Tyr Leu Ala Asn Asn Leu Glu Ser Gly Val Pro Asp
 50                  55                  60

Arg Phe Ser Gly Ser Gly Ser Arg Thr Asp Phe Thr Leu Thr Ile Ser
 65                  70                  75                  80

Ser Leu Gln Ala Glu Asp Val Ala Val Tyr Tyr Cys Gln Gln Asn Asn
                 85                  90                  95

Glu Asp Pro Trp Thr Phe Gly Gly Gly Thr Lys Val Glu Ile Lys Arg
                100                 105                 110
```

<210> SEQ ID NO 23
<211> LENGTH: 5
<212> TYPE: PRT
<213> ORGANISM: Artificial Sequence
<220> FEATURE:
<223> OTHER INFORMATION: Exemplary CDRH Sequence - CDRH1

<400> SEQUENCE: 23

```
Asp Tyr Tyr Ile Asn
 1               5
```

<210> SEQ ID NO 24
<211> LENGTH: 17
<212> TYPE: PRT
<213> ORGANISM: Artificial Sequence
<220> FEATURE:
<223> OTHER INFORMATION: Exemplary CDRH Sequence - CDRH2

<400> SEQUENCE: 24

```
Arg Ile Tyr Pro Gly Ser Gly Asn Thr Tyr Tyr Asn Glu Lys Phe Lys
 1               5                  10                  15

Gly
```

<210> SEQ ID NO 25
<211> LENGTH: 8
<212> TYPE: PRT
<213> ORGANISM: Artificial Sequence
<220> FEATURE:
<223> OTHER INFORMATION: Exemplary CDRH Sequence - CDRH3

<400> SEQUENCE: 25

```
Tyr Ser Ala Ser Ala Met Asp Tyr
1               5

<210> SEQ ID NO 26
<211> LENGTH: 15
<212> TYPE: PRT
<213> ORGANISM: Artificial Sequence
<220> FEATURE:
<223> OTHER INFORMATION: Exemplary CDRL Sequence - CDRL 1

<400> SEQUENCE: 26

Arg Ala Ser Glu Ser Val Asp Ser Tyr Gly Lys Ser Phe Met Tyr
1               5                   10                  15

<210> SEQ ID NO 27
<211> LENGTH: 7
<212> TYPE: PRT
<213> ORGANISM: Artificial Sequence
<220> FEATURE:
<223> OTHER INFORMATION: Exemplary CDRL Sequence - CDRL 2

<400> SEQUENCE: 27

Leu Ala Asn Asn Leu Glu Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Exemplary CDRL Sequence - CDRL 3

<400> SEQUENCE: 28

Gln Gln Asn Asn Glu Asp Pro Trp Thr
1               5

<210> SEQ ID NO 29
<211> LENGTH: 351
<212> TYPE: DNA
<213> ORGANISM: Artificial Sequence
<220> FEATURE:
<223> OTHER INFORMATION: Exemplary nucleic acid encoding heavy chain
      variable

<400> SEQUENCE: 29
caggtgcagc tggtgcagag cggcgcggaa gtgaaaaaac cgggcgcgag cgtgaaagtg      60
agctgcaaag cgagcggcta cctttacc gattattata ttaactgggt gcgccaggcg      120
accggccagg gcctggaatg gatgggccgc atttatccgg gcagcggcaa cacctattat      180
aacgaaaaat ttaaggccg cgtgaccatg acccgcgata ccagcattag caccgcgtat      240
atggaactga gcagcctgcg cagcgaagat accgcggtgt attattgcgc gcgctatagc      300
gcgagcgcga tggattattg gggccagggc accctggtga ccgtgagcag c              351

<210> SEQ ID NO 30
<211> LENGTH: 351
<212> TYPE: DNA
<213> ORGANISM: Artificial Sequence
<220> FEATURE:
<223> OTHER INFORMATION: Exemplary nucleic acid encoding heavy chain
      variable

<400> SEQUENCE: 30
caggtgcagc tggtgcagag cggcgcggaa gtgaaaaaac cgggcgcgag cgtgaaagtg      60
```

```
agctgcaaag cgagcggcta taccttacc gattattata ttaactgggt gcgccaggcg    120
accggccagg gcctggaatg gatgggccgc atttatccgg gcagcggcaa cacctattat    180
aacgaaaaat ttaaaggccg cgtgaccctg accgcggaaa aaagcagcag caccgcgtat    240
atggaactga gcagcctgcg cagcaagat accgcggtgt attttgcgc ggcgtatagc     300 gcgagcgcga tggattattg gggccagggc accctggtga ccgtgagcag c            351
```

```
<210> SEQ ID NO 31
<211> LENGTH: 336
<212> TYPE: DNA
<213> ORGANISM: Artificial Sequence
<220> FEATURE:
<223> OTHER INFORMATION: Exemplary nucleic acid encoding light chain
      variable

<400> SEQUENCE: 31
gatattgtga tgacccagag cccggatagc ctggcggtga gcctgggcga acgcgcgacc    60
attaactgcc gcgcgagcga aagcgtggat agctatggca aagctttat gtattggtat    120 cagcagaaac cgggccagcc gccgaaactg ctgatttatc tggcgaacaa cctggaaagc    180
ggcgtgccgg atcgctttag cggcagcggc agcggcaccg attttaccct gaccattagc    240
agcctgcagg cggaagatgt ggcggtgtat tattgccagc agaacaacga agatccgtgg    300
acctttggcg gcggcaccaa agtggaaatt aaacgc                              336
```

```
<210> SEQ ID NO 32
<211> LENGTH: 336
<212> TYPE: DNA
<213> ORGANISM: Artificial Sequence
<220> FEATURE:
<223> OTHER INFORMATION: Exemplary nucleic acid encoding light chain
      variable

<400> SEQUENCE: 32
gatgtggtgc tgacccagag cccggatagc ctggcggtga gcctgggcga acgcgcgacc    60
attaactgcc gcgcgagcga aagcgtggat agctatggca aagctttat gtattggtat    120 cagcagaaac cgggccagcc gccgaaactg ctgatttatc tggcgaacaa cctggaaagc    180
ggcgtgccgg atcgctttag cggcagcggc agccgcaccg attttaccct gaccattagc    240
agcctgcagg cggaagatgt ggcggtgtat tattgccagc agaacaacga agatccgtgg    300
acctttggcg gcggcaccaa agtggaaatt aaacgc                              336
```

```
<210> SEQ ID NO 33
<211> LENGTH: 136
<212> TYPE: PRT
<213> ORGANISM: Mus musculus

<400> SEQUENCE: 33

Met Gly Trp Ser Trp Ile Phe Phe Leu Leu Ser Gly Thr Ala Gly
1               5                   10                  15

Val His Cys Gln Val Gln Leu Thr Gln Ser Gly Ala Glu Leu Val Arg
                20                  25                  30

Pro Gly Ala Ser Val Lys Leu Ser Cys Lys Ala Ser Gly Tyr Thr Phe
            35                  40                  45

Thr Asp Tyr Tyr Ile Asn Trp Val Lys Gln Arg Pro Gly Gln Gly Leu
        50                  55                  60

Glu Trp Ile Ala Arg Ile Tyr Pro Gly Ser Gly Asn Thr Tyr Tyr Asn
65                  70                  75                  80
```

-continued

```
Glu Lys Phe Lys Gly Lys Ala Thr Leu Thr Ala Glu Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Ala Tyr Ser Ala Ser Ala Met Asp Tyr Trp Gly Gln
        115                 120                 125

Gly Thr Ser Val Thr Val Ser Ser
    130             135

<210> SEQ ID NO 34
<211> LENGTH: 131
<212> TYPE: PRT
<213> ORGANISM: Mus musculus

<400> SEQUENCE: 34

Met Glu Thr Asp Thr Leu Leu Leu Trp Val Leu Leu Leu Trp Val Pro
1               5                   10                  15

Gly Ser Thr Gly Asn Val Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Ser Tyr Gly Lys Ser Phe Met Tyr Trp Tyr Gln Gln Lys Pro
    50                  55                  60

Gly Gln Pro Pro Lys Leu Leu Ile Tyr Leu Ala Asn Asn Leu Glu Ser
65                  70                  75                  80

Gly Val Pro Ala Arg Phe Ser Gly Ser Gly Ser Arg Thr Asp Phe Thr
                85                  90                  95

Leu Thr Ile Asp Pro Val Glu Ala Asp Asp Ala Ala Ser Tyr Tyr Cys
            100                 105                 110

Gln Gln Asn Asn Glu Asp Pro Trp Thr Phe Gly Gly Gly Thr Lys Leu
        115                 120                 125

Glu Ile Lys
    130
```